US012778582B2

(12) United States Patent
Nishihara

(10) Patent No.: US 12,778,582 B2
(45) Date of Patent: Nov. 3, 2026

(54) SURGICAL INSTRUMENT HOLDING DEVICE AND SURGERY ASSISTING DEVICE

(71) Applicant: RIVERFIELD INC., Tokyo (JP)

(72) Inventor: Teruyuki Nishihara, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 976 days.

(21) Appl. No.: 17/890,497

(22) Filed: Aug. 18, 2022

(65) Prior Publication Data

US 2022/0387028 A1 Dec. 8, 2022

Related U.S. Application Data

(63) Continuation of application No. PCT/JP2020/006885, filed on Feb. 20, 2020.

(51) Int. Cl.
*A61B 17/072* (2006.01)
*A61B 17/00* (2006.01)

(52) U.S. Cl.
CPC .. *A61B 17/072* (2013.01); *A61B 2017/00398* (2013.01)

(58) Field of Classification Search
CPC .................... A61B 17/072; A61B 2017/00398
See application file for complete search history.

(56) References Cited

U.S. PATENT DOCUMENTS

| | | | |
|---|---|---|---|
| 5,441,042 | A | 8/1995 | Putman |
| 5,509,192 | A | 4/1996 | Ota et al. |
| 8,474,771 | B2 | 7/2013 | Ross |
| 2005/0070757 | A1 | 3/2005 | Niwa et al. |

(Continued)

FOREIGN PATENT DOCUMENTS

| | | | |
|---|---|---|---|
| CN | 1602794 | A | 4/2005 |
| CN | 101583459 | A | 11/2009 |

(Continued)

OTHER PUBLICATIONS

Extended European Search Report issued Jan. 9, 2023 in European Application No. 20920427.0.

(Continued)

*Primary Examiner* — Carl H Layno
*Assistant Examiner* — Jennifer L Ghand
(74) *Attorney, Agent, or Firm* — Sughrue Mion, PLLC

(57) ABSTRACT

A surgical instrument holding device includes a holding body, an adapter, a separator, and a driving body. The holding body holds a surgical instrument. The adapter receives the surgical instrument and is disposed between the surgical instrument and the holding body. The separator is provided between the adapter and the holding body and receives the adapter. The driving body supplies a driving force to the holding body to drive the surgical instrument. The adapter includes a tubular portion through which the surgical instrument is received, and an arc shaped protrusion. The separator is arc shaped with a circumference extending from a first circumferential edge to a second circumferential edge. When the adapter is received in separator, the arc shaped protrusion engages the first circumferential edge and the second circumferential edge of the separator to restrict rotation of the adapter with respect to the separator.

8 Claims, 35 Drawing Sheets

(56) References Cited

U.S. PATENT DOCUMENTS

| | | | | |
|---|---|---|---|---|
| 2008/0262654 | A1 | 10/2008 | Omori et al. | |
| 2009/0076327 | A1 | 3/2009 | Ohki | |
| 2010/0018038 | A1 | 1/2010 | Ukai et al. | |
| 2010/0022825 | A1 | 1/2010 | Yoshie | |
| 2010/0176584 | A1 | 7/2010 | Ito et al. | |
| 2012/0296159 | A1 | 11/2012 | Kanazawa et al. | |
| 2013/0193295 | A1 | 8/2013 | Lui et al. | |
| 2015/0297305 | A1 | 10/2015 | Wyslucha et al. | |
| 2016/0151115 | A1 | 6/2016 | Karguth et al. | |
| 2016/0361127 | A1 | 12/2016 | Dachs, II et al. | |
| 2017/0045730 | A1 | 2/2017 | Kato | |
| 2017/0086930 | A1 | 3/2017 | Thompson et al. | |
| 2017/0296040 | A1 | 10/2017 | Haraguchi et al. | |
| 2017/0348063 | A1 | 12/2017 | Braun et al. | |
| 2018/0184995 | A1 | 7/2018 | Liu et al. | |
| 2019/0159853 | A1 | 5/2019 | Haraguchi et al. | |
| 2019/0328418 | A1 | 10/2019 | Ahn | |
| 2020/0081585 | A1 | 3/2020 | Petre et al. | |
| 2020/0121416 | A1 | 4/2020 | Sasai et al. | |
| 2020/0305991 | A1 | 10/2020 | Ago et al. | |
| 2020/0305997 | A1* | 10/2020 | Ago | A61B 17/00 |
| 2020/0405279 | A1 | 12/2020 | Xu et al. | |
| 2021/0007811 | A1 | 1/2021 | Troxell et al. | |
| 2021/0196982 | A1 | 7/2021 | Guo et al. | |
| 2022/0387021 | A1* | 12/2022 | Nishihara | A61B 17/068 |
| 2022/0401181 | A1* | 12/2022 | Nishihara | A61B 90/50 |

FOREIGN PATENT DOCUMENTS

| | | | |
|---|---|---|---|
| CN | 101677905 | A | 3/2010 |
| CN | 102858225 | A | 1/2013 |
| CN | 109640866 | A | 4/2019 |
| JP | 6-063003 | A | 3/1994 |
| JP | 2003-284726 | A | 10/2003 |
| JP | 2006-61272 | A | 3/2006 |
| JP | 2006-189592 | A | 7/2006 |
| JP | 2015-228922 | A | 12/2015 |
| JP | 2017-513552 | A | 6/2017 |
| JP | 2019-37658 | A | 3/2019 |
| JP | 2020-005784 | A | 1/2020 |
| WO | 2015/142814 | A1 | 9/2015 |
| WO | 2016/051494 | A1 | 4/2016 |
| WO | 2020/009155 | A1 | 1/2020 |

OTHER PUBLICATIONS

Extended European Search Report issued Jan. 9, 2023 in European Application No. 20920344.7.

Extended European Search Report issued Jan. 9, 2023 in European Application No. 20920428.8.

Extended European Search Report issued Mar. 9, 2023 in European Application No. 20919748.2.

Office Action issued Mar. 10, 2025 in U.S. Appl. No. 17/890,829.

International Search Report for PCT/JP2020/006885 dated May 19, 2020.

International Search Report for PCT/JP2020/006884 dated May 19, 2020.

International Search Report for PCT/JP2020/006886 dated May 19, 2020.

International Search Report for PCT/JP2020/006887 dated May 19, 2020.

Written Opinion for PCT/JP2020/006885 dated May 19, 2020.

Office Action dated Oct. 10, 2025 issued in U.S. Appl. No. 17/890,505.

Notice of Allowance dated Jul. 8, 2025, which issued during the prosecution of U.S. Appl. No. 17/890,829.

Office Action dated Aug. 25, 2025 issued in U.S. Appl. No. 17/890,842.

Office Action issued Mar. 18, 2026 in U.S. Appl. No. 17/890,842.

Communication dated Jun. 1, 2026, issued in U.S. Appl. No. 17/890,842.

Communication dated Jul. 1, 2026, issued in U.S. Appl. No. 17/890,842.

Communication dated Jun. 30, 2026, issued in U.S. Appl. No. 17/890,505.

* cited by examiner

SURGICAL INSTRUMENT HOLDING DEVICE AND SURGERY ASSISTING DEVICE

CROSS-REFERENCE TO RELATED APPLICATION

This U.S. Application is a continuation application of International Application No. PCT/JP2020/006885, filed Feb. 20, 2020, the contents of which being incorporated by reference herein in its entirety.

BACKGROUND

The present disclosure relates to a surgical instrument holding device that holds a surgical instrument and a surgery assisting device including the surgical instrument holding device.

In recent years, surgical operations using surgery assisting devices have come into widespread use. Some surgery assisting devices are provided with a surgical instrument that is inserted in the body cavity of the patient to perform various surgical operations. There are various ways in which the surgical instrument may be held by the surgery assisting device. However, when a position of each part in the surgical instrument is unexpectedly changed, the surgical operations may be compromised, decreasing accuracy and safety of the surgery.

SUMMARY

It is an aspect to provide a surgical instrument holding device and a surgery assisting device that increases accuracy and safety of surgery by preventing displacement of a surgical instrument with respect to a holding body.

According to an aspect of one or more embodiments, there is provided a surgical instrument holding device comprising an adapter from which a surgical instrument is detachable and that is provided with a restricted portion; a separator from which the adapter is detachable; a holding body from which the separator is detachable; and a driving body configured to support the holding body in a rotatable manner and apply a driving force to the holding body, wherein the adapter is provided with a tubular portion through which the surgical instrument penetrates, the separator is provided with an insertion portion into which the tubular portion is inserted, the surgical instrument is held by the holding body via the adapter and the separator, a restricting portion is formed in the separator, and the restricting portion engages with the restricted portion of the adapter to restrict rotation of the adapter in a circumferential direction of the tubular portion.

According to another aspect of one or more embodiments, there is provided a surgical instrument holding device comprising an adapter from which a surgical instrument is detachable and that is provided with a restricted portion; a separator from which the adapter is detachable; a holding body from which the separator is detachable; and a driving body configured to support the holding body in a rotatable manner and apply a driving force to the holding body, wherein the adapter comprises a tubular portion through which the surgical instrument penetrates, the separator comprises an insertion portion into which the tubular portion is received, and a restricting portion, the surgical instrument is held by the holding body via the adapter and the separator, and the restricting portion of the separator engages with the restricted portion of the adapter to restrict rotation of the adapter in a circumferential direction.

According to yet another aspect of one or more embodiments, there is provided a surgical instrument holding device comprising a holding body configured to hold a surgical instrument; an adapter which is configured to receive the surgical instrument, the adapter being disposed between the surgical instrument and the holding body; a separator that is provided between the adapter and the holding body and that is configured to receive the adapter; and a driving body configured to supply a driving force to the holding body to drive the surgical instrument, wherein the holding body, the adapter, and the separator are coaxial, the adapter comprises a tubular portion through which the surgical instrument is received, and an arc shaped protrusion, the separator is arc shaped with a circumference extending from a first circumferential edge to a second circumferential edge, and when the adapter is received in the separator, the arc shaped protrusion engages the first circumferential edge and the second circumferential edge of the separator to restrict rotation of the adapter with respect to the separator.

BRIEF DESCRIPTION OF DRAWINGS

The above and/or other aspects will become apparent and more readily appreciated from the following description of exemplary embodiments, taken in conjunction with the accompanying drawings in which.

DETAILED DESCRIPTION

Figure 1:
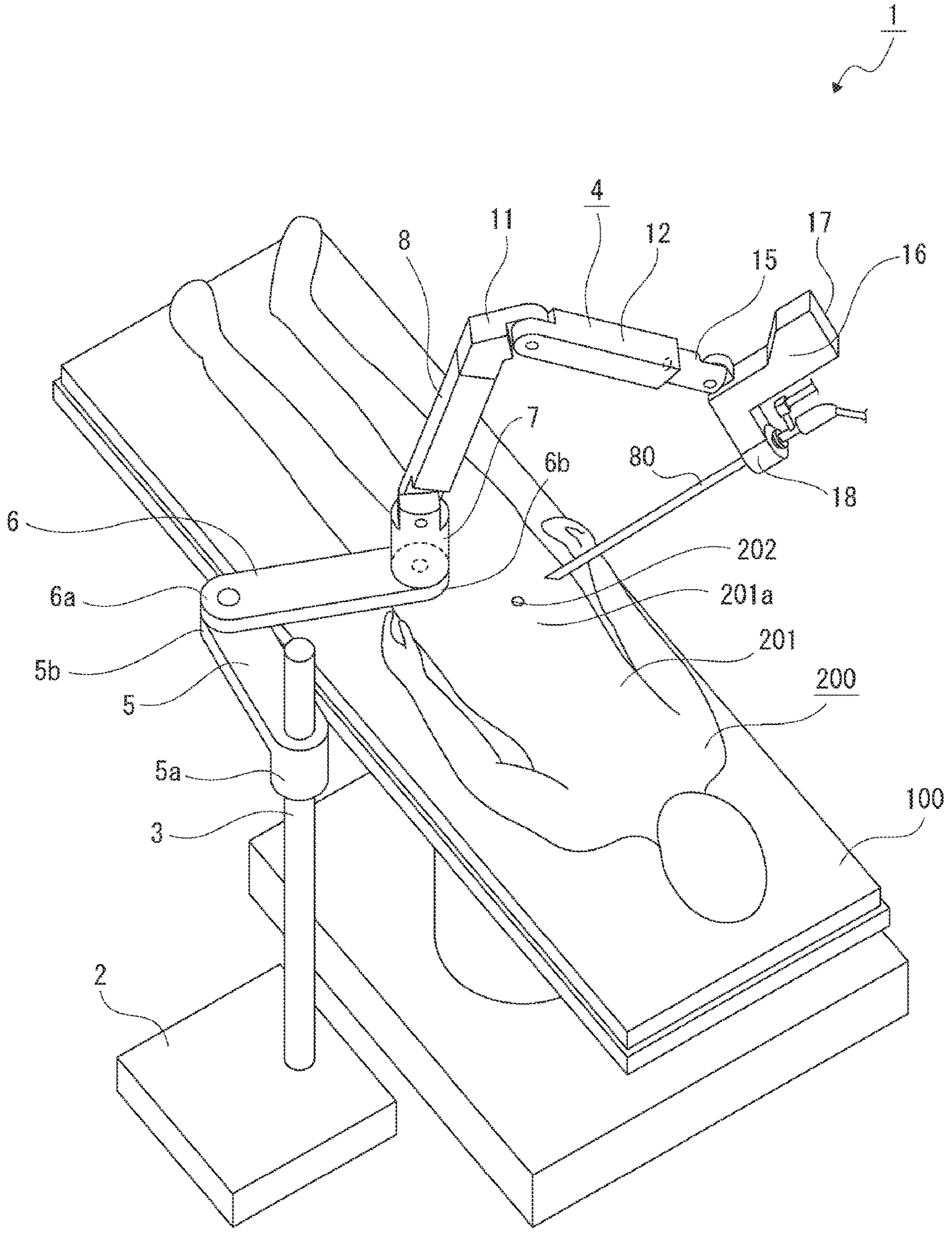
FIG. 1 depicts a schematic perspective view illustrating a surgery assisting device, according to some embodiments.

In recent years, surgical operations using surgery assisting devices have come into widespread use. Such a surgery assisting device includes a plurality of movable bodies that are connected rotatably to one another in order. The movable bodies are rotated by the driving forces of actuators. A movable body positioned at one end in a connecting direction is provided as a holding body. The plurality of movable bodies are provided as an arm section or a joint section. The holding body holds a surgical instrument that has a part (distal end portion) thereof to be inserted into the body cavity of a patient. An endoscope, forceps, and the like are used as the surgical instrument according to the kind of surgery and conditions.

When the plurality of movable bodies are each rotated in a predetermined direction in the surgery assisting device, the position and pose of the surgical instrument are changed in association with the rotational operation of the movable bodies. A surgical operation is performed with the distal end portion of the surgical instrument inserted in the body cavity of the patient.

The surgical operation using the surgery assisting device as described above is typically performed by an operator (e.g., a surgeon) who remotely operates the surgery assisting device installed in an operating room according to a master-slave system. When such a surgical operation is performed, a pivot point is set to serve as a reference point for the position and pose of the surgical instrument.

The pivot point is a position substantially coinciding with a port that is formed in the body cavity of the patient and through which the surgical instrument is inserted. In a case where a trocar is used, the pivot point substantially coincides with the position of the trocar. Hence, in a state in which the surgical instrument is inserted in the body cavity of the patient, the position and pose of the surgical instrument are controlled such that a part of the surgical instrument always passes through the pivot point. When a part of the surgical instrument passes through the pivot point, generation of a load on a tissue in the vicinity of the body surface of the patient is prevented, and thus safety is reserved.

Some surgery assisting devices as described above are provided with a surgical instrument holding device that holds the surgical instrument. There are various types of surgical instrument holding devices. Such a surgical instrument holding device is provided with the above-described holding body. A part or the whole of the holding body is a holding portion that holds the surgical instrument.

As described above, there are various types of surgical instrument holding devices. Some surgical instrument holding devices have an adapter for making the size and shape of the holding body correspond to those of the surgical instrument, and the surgical instrument is attached to and held by the holding body via the adapter. In addition, there is a type of a surgery assisting device in which a drape for separating a clean region and an unclean region from each other is attached to a separator and the separator is attached to the holding body. In a surgery assisting device of such a type, the adapter may be attached to the separator, and the surgical instrument may be held by the holding body via the separator and the adapter.

The surgical instrument is used in a state in which the distal end portion of the surgical instrument is inserted in the body cavity of the patient. For example, a state inside the body cavity is observed by an endoscope included in the surgical instrument, or a lesion site is cut off by forceps provided to the distal end portion of the surgical instrument.

However, as described above, when the position of each part in the surgical instrument is unexpectedly changed with respect to the holding body, the state inside the body cavity may not be accurately observed by the endoscope, or accurate cutoff of the lesion site by the forceps may be compromised, thereby decreasing accuracy and safety of the surgery.

In addition, as described above, the surgical operation using the surgery assisting device is often performed by an operator who remotely operates the surgery assisting device according to a master-slave system.

However, when the position of each part in the surgical instrument is accidentally changed with respect to the holding body, the position and posture of the surgical instrument which are recognized by the operator in reference to information input to an operating device as a master machine are different from the actual position and posture of the surgical instrument, and, again, accuracy and safety of the surgery may be decreased.

It is accordingly an object of a surgical instrument holding device and a surgery assisting device according to some embodiments to increase accuracy and safety of surgery by preventing displacement of a surgical instrument with respect to a holding body.

A surgical instrument holding device according to one or more embodiments may include an adapter from which a surgical instrument is detachable and that is provided with a restricted portion, a separator from which the adapter is detachable, a holding body from which the separator is detachable, and a driving body configured to support the holding body in a rotatable manner and apply a driving force to the holding body, in which the adapter is provided with a tubular portion through which the surgical instrument penetrates, the separator is provided with an insertion portion into which the tubular portion is inserted, the surgical instrument is held by the holding body via the adapter and the separator, and a restricting portion is formed in the separator, the restricting portion engaging with the restricted portion and restricting rotation of the adapter in a circumferential direction of the tubular portion.

Thus, in a state in which the adapter is attached to the separator and the separator is attached to the holding body, rotation of the adapter, to which the surgical instrument is attached, with respect to the separator is restricted.

In the surgical instrument holding device according to one or more embodiments, a rotation restricted portion may be provided in the separator, and a rotation restricting portion may be formed in the holding body, the rotation restricting portion engaging with the rotation restricted portion and restricting rotation of the separator in a circumferential direction of the insertion portion.

Thus, in a state in which the adapter is attached to the separator and the separator is attached to the holding body, rotation of the adapter with respect to the separator is restricted, and rotation of the separator with respect to the holding body is restricted.

In the surgical instrument holding device according to one or more embodiments, a first engagement receiving portion may be formed in the holding body, a second engagement receiving portion may be formed in the separator, the separator may be provided with a first engaging portion that is elastically deformed and engaged with the first engagement receiving portion at a time of attachment of the separator to the holding body, the adapter may be provided with a second engaging portion that is elastically deformed and engaged with the second engagement receiving portion at a time of attachment of the adapter to the separator, and the separator may be attached to the holding body by engagement of the first engaging portion with the first engagement receiving portion in a state in which the first engaging portion is elastically restored, and the adapter may be attached to the separator by engagement of the second engaging portion with the second engagement receiving portion in a state in which the second engaging portion is elastically restored.

Thus, the surgical instrument is held by the holding body via the separator and the adapter by engagement of the first engaging portion that has been elastically deformed with the first engagement receiving portion in a state in which the first engaging portion is elastically restored and engagement of the second engaging portion that has been elastically deformed with the second engagement receiving portion in a state in which the second engaging portion is elastically restored.

In the surgical instrument holding device according to one or more embodiments, the rotation restricted portion and the first engaging portion may be formed in a shape of protruding with respect to the insertion portion, and the rotation restricted portion and the first engaging portion may be provided in such a manner as to be continuous with each other.

Thus, the rotation restricted portion and the first engaging portion both in a shape of protruding with respect to the insertion portion are not provided at positions separated from each other in the separator.

In the surgical instrument holding device according to one or more embodiments, an insertion and extraction opening in a radial direction may be formed in the insertion portion, and the surgical instrument attached to the adapter may be inserted or extracted through the insertion and extraction opening.

Thus, the insertion and extraction of the surgical instrument can be performed in the radial direction of the insertion portion, and the surgical instrument does not need to be moved in an axial direction of the insertion portion to attach or detach the surgical instrument to or from the separator via the adapter.

A surgery assisting device according to one or more embodiments may be a surgery assisting device including a surgical instrument holding device configured to hold a surgical instrument. The surgical instrument holding device may include an adapter from which the surgical instrument is detachable and that is provided with a restricted portion, a separator from which the adapter is detachable, a holding body from which the separator is detachable, and a driving body configured to support the holding body in a rotatable manner and apply a driving force to the holding body. The adapter is provided with a tubular portion through which the surgical instrument penetrates, the separator is provided with an insertion portion into which the tubular portion is inserted, the surgical instrument is held by the holding body via the adapter and the separator, and a restricting portion is formed in the separator, the restricting portion engaging with the restricted portion and restricting rotation of the adapter in a circumferential direction of the tubular portion.

Thus, in the surgical instrument holding device according to one or more embodiments, in a state in which the adapter is attached to the separator and the separator is attached to the holding body, rotation of the adapter, to which the surgical instrument is attached, with respect to the separator is restricted.

According to various embodiments disclosed herein, in a state in which the adapter is attached to the separator and the separator is attached to the holding body, rotation of the adapter, to which the surgical instrument is attached, with respect to the separator is restricted. Thus, unintended rotation of the surgical instrument with respect to the holding body is prevented, and accuracy and safety of surgery can be reserved by preventing displacement of the surgical instrument with respect to the holding body.

A surgical instrument holding device and a surgery assisting device according to various example embodiments will hereinafter be described with reference to the accompanying drawings.

An embodiment illustrated in the following represents an example in which the surgery assisting device according to some embodiments is applied as a type used in a state of being installed on the floor of an operating room or the like. However, the scope of application of the surgery assisting device according to some embodiments is not limited to the type used in a state of being installed on the floor of an operating room or the like, and the surgery assisting device according to some embodiments can also be applied as a type used in a state of being attached to the ceiling or wall surface of an operating room.

It is to be noted that forward and rearward, upward and downward, and leftward and rightward directions illustrated in the following are directions for the convenience of description, and are not limited to these directions.

In addition, the surgery assisting device illustrated in the following has a configuration in which movable bodies are rotated. This "rotation" means operation in an axial rotation direction about a reference axis (central axis) including an optional point, and refers to operation including also "revolution."

<General Configuration of Surgery Assisting Device>

Figure 2:
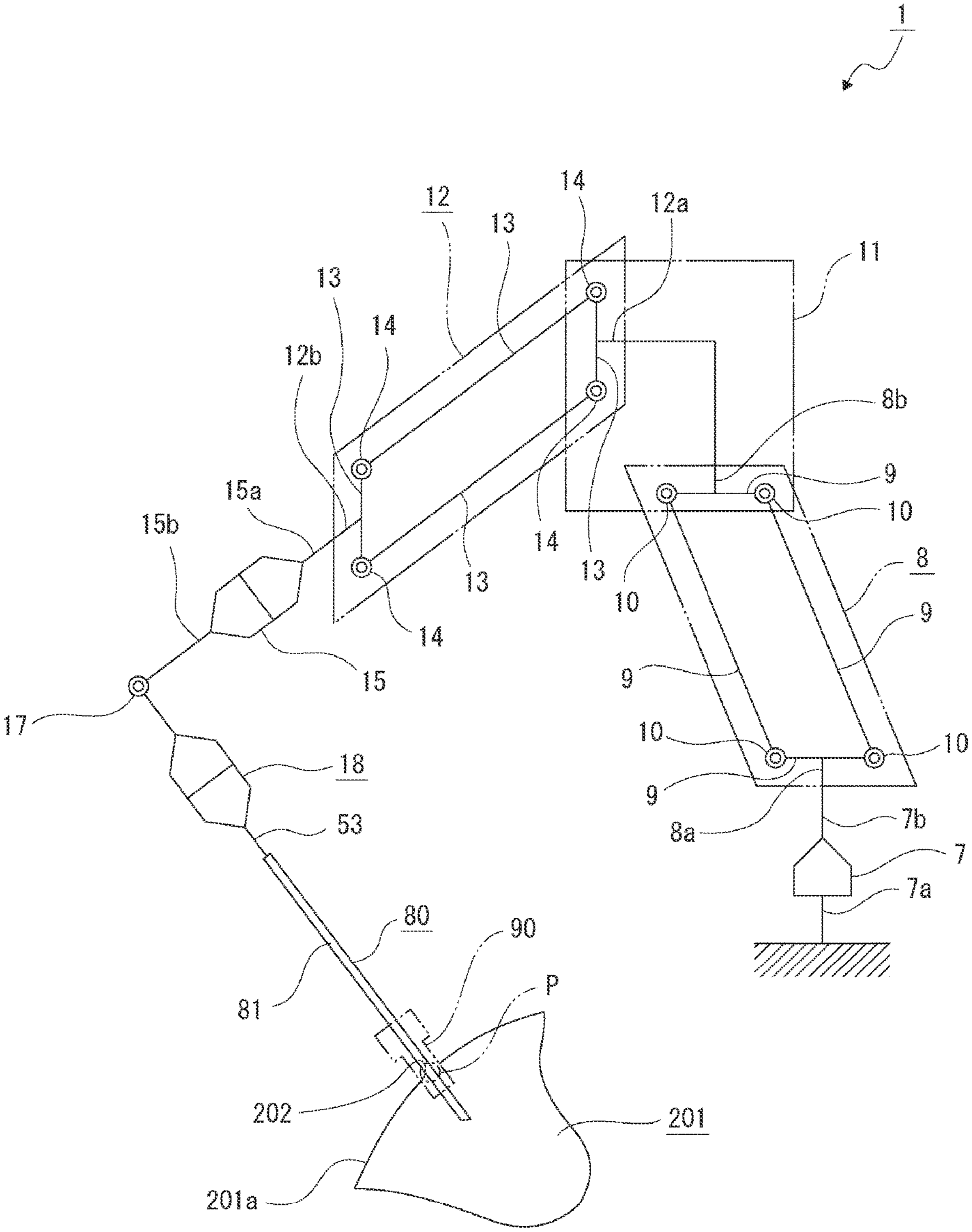
FIG. 2 is a conceptual diagram of the surgery assisting device of FIG. 1, according to some embodiments.

A general configuration of a surgery assisting device 1 and the like will first be described (see FIGS. 1 to 3).

An operating table 100 is installed in the operating room. A patient 200 is laid down on his or her back, for example, on the operating table 100 (see FIG. 1). A port 202 is formed in a body cavity 201, for example, an abdominal wall 201*a*, of the patient 200. A part (distal end portion) of a surgical instrument to be described later is inserted into the port 202 when a surgical operation is performed. The port 202 is a small hole into which a shaft-shaped surgical instrument is inserted.

The surgery assisting device 1 includes a base 2 placed on the floor of the operating room or the like, a pole 3 in a round shaft shape which is fixed to the base 2, and a main unit 4 supported by the pole 3. The base 2 is installed on the floor or the like on a side of the operating table 100. A lower end portion of the pole 3 is fixed to the base 2 in a state in which the pole 3 extends vertically.

The main unit 4 is supported by the pole 3 in such a manner as to be movable in an upward-downward direction. The main unit 4 has a configuration in which respective parts are connected to one another in a rotatable state. The main unit 4 can be fixed to the pole 3 at a desired position in the upward-downward direction.

The main unit 4 includes a first connecting arm 5 and a second connecting arm 6 rotatably connected to each other.

The first connecting arm 5 is formed in a shape extending in a horizontal direction. The first connecting arm 5 has a supported tubular portion 5*a* at one end portion thereof in a longitudinal direction and has a pivot portion 5*b* at the other end portion in the longitudinal direction thereof. The pole 3 is inserted through the supported tubular portion 5*a* of the first connecting arm 5. The first connecting arm 5 can manually or electrically be moved in the upward-downward direction with respect to the pole 3, and can be rotated in an axial rotation direction with respect to the pole 3 with the supported tubular portion 5*a* as a pivot.

The first connecting arm 5 can be fixed to the pole 3 at a desired position in the upward-downward direction and at a desired position in the axial rotation direction.

The second connecting arm 6 is formed in a shape extending in the horizontal direction. The second connecting arm 6 has a pivot portion 6*a* at one end portion thereof in a longitudinal direction and has a supporting shaft portion 6*b* at the other end portion thereof in the longitudinal direction. The pivot portion 6*a* of the second connecting arm 6 is vertically superposed on the pivot portion 5*b* of the first connecting arm 5. The pivot portion 6*a* of the second connecting arm 6 and the pivot portion 5*b* of the first connecting arm 5 are connected to each other in a rotatable state. The second connecting arm 6 can manually or electrically be rotated with respect to the first connecting arm 5 with the pivot portion 6*a* as a pivot.

The main unit 4 includes a first movable body 7 that functions as a joint section. The first movable body 7 is connected rotatably to the supporting shaft portion 6*b* of the second connecting arm 6 (see FIG. 1 and FIG. 2).

The first movable body 7 has a proximal end side connecting portion 7*a* at an end portion thereof on the second connecting arm 6 side and has a distal end side connecting portion 7*b* at an end portion thereof on a side opposite to the second connecting arm 6 side. The proximal end side connecting portion 7*a* of the first movable body 7 is connected rotatably to the supporting shaft portion 6*b* of the second connecting arm 6. The first movable body 7 is, for example, rotated with respect to the second connecting arm 6 in an axial rotation direction about a reference axis extending in the upward-downward direction. Hence, because the first movable body 7 is rotated with respect to the second connecting arm 6, the surgery assisting device 1 has one degree of freedom in an operating direction.

The main unit 4 includes a second movable body 8 that functions as an arm section. The second movable body 8 is connected rotatably to the distal end side connecting portion 7*b* of the first movable body 7.

The second movable body 8 has a proximal end side connecting portion 8*a* at one end portion thereof in a longitudinal direction and has a distal end side connecting portion 8*b* at the other end portion thereof in the longitudinal direction. The proximal end side connecting portion 8*a* of the second movable body 8 is connected rotatably to the distal end side connecting portion 7*b* of the first movable body 7. The second movable body 8 is, for example, rotated with respect to the first movable body 7 in an axial rotation direction about a reference axis extending in a direction orthogonal to the connecting direction in which the second movable body 8 and the first movable body 7 are connected to each other. Hence, because the second movable body 8 is rotated with respect to the first movable body 7, the surgery assisting device 1 has one degree of freedom in an operating direction.

The second movable body 8 is provided with a link mechanism, for example. The link mechanism includes two sets of parallel link portions 9 and coupling pins 10 that couple the link portions 9 to each other. The coupling pins 10 positioned on the first movable body 7 side in the second movable body 8 are connected in a rotatable state to the distal end side connecting portion 7*b* of the first movable body 7.

The main unit 4 includes a third movable body 12 that functions as an arm section. The third movable body 12 is connected to an intermediate connecting member 11. The third movable body 12 has a proximal end side connecting portion 12*a* at one end portion thereof in a longitudinal direction and has a distal end side connecting portion 12*b* at the other end portion thereof in the longitudinal direction. The proximal end side connecting portion 12*a* of the third movable body 12 is connected to the intermediate connecting member 11. The third movable body 12 is, for example, rotated with respect to the intermediate connecting member 11 in an axial rotation direction about a reference axis extending in a direction orthogonal to the connecting direction in which the third movable body 12 and the intermediate connecting member 11 are connected to each other. Hence, because the third movable body 12 is rotated with respect to the intermediate connecting member 11, the surgery assisting device 1 has one degree of freedom in an operating direction.

The third movable body 12 is provided with a link mechanism, for example. The link mechanism includes two sets of parallel link portions 13 and coupling pins 14 that couple the link portions 13 to each other. In the third movable body 12, the coupling pins 14 positioned on the intermediate connecting member 11 side are connected in a rotatable state to another end portion of the intermediate connecting member 11.

While the above description illustrates an example in which the second movable body 8 and the third movable body 12 are connected to each other via the intermediate connecting member 11, in some embodiment the surgery assisting device 1 may not be provided with the intermediate connecting member 11, and the second movable body 8 and the third movable body 12 may be connected to each other without the intervention of the intermediate connecting member 11.

The main unit 4 includes a fourth movable body 15 that functions as a joint section. The fourth movable body 15 is connected rotatably to the distal end side connecting portion 12*b* of the third movable body 12. The fourth movable body 15 has a proximal end side connecting portion 15*a* at an end portion thereof on the third movable body 12 side and has a distal end side connecting portion 15*b* at an end portion thereof on a side opposite from the third movable body 12. The proximal end side connecting portion 15*a* of the fourth movable body 15 is connected rotatably to the distal end side connecting portion 12*b* of the third movable body 12. The fourth movable body 15 is, for example, rotated with respect to the third movable body 12 in an axial rotation direction about a reference axis extending in the connecting direction in which the fourth movable body 15 and the third movable body 12 are connected to each other. Hence, because the fourth movable body 15 is rotated with respect to the third movable body 12, the surgery assisting device 1 has one degree of freedom in an operating direction.

The first movable body 7, the second movable body 8, the third movable body 12, and the fourth movable body 15 described above are rotated by the driving force of an unillustrated electric actuator, for example. In some embodiments, the first movable body 7, the second movable body 8, the third movable body 12, and the fourth movable body 15 may be rotated by the driving force of a pneumatic actuator.

The main unit 4 includes a surgical instrument holding device 16. The surgical instrument holding device 16 is connected rotatably to the distal end side connecting portion 15*b* of the fourth movable body 15.

Figure 3:
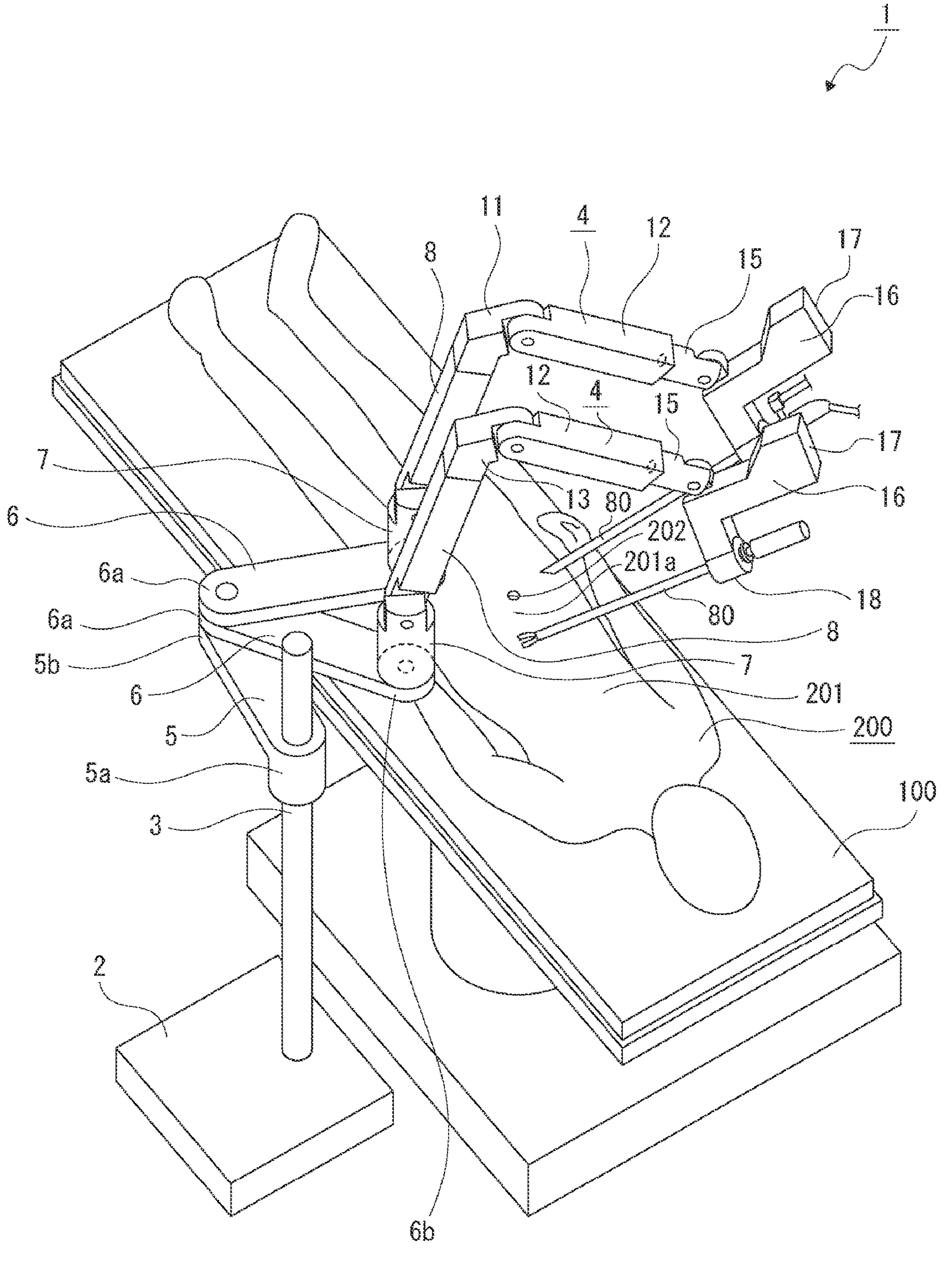
FIG. 3 is a schematic perspective view illustrating a surgery assisting device, according to some embodiments.

It is to be noted that, while the above description illustrates, as an example, the surgery assisting device 1 including one main unit 4 having a plurality of movable bodies, the number of main units 4 provided to the surgery assisting device 1 is not limited to one, and may be plural (see FIG. 3). In a case where two main units 4, for example, are provided in such a surgery assisting device 1, adoptable is a configuration in which two second connecting arms 6 each rotatable with respect to the first connecting arm 5 are provided and first movable bodies 7 are respectively connected to the second connecting arms 6.

Providing a plurality of main units 4 in such a manner enables a surgical operation to be performed with a plurality of surgical instruments and thus enables a shorter surgery time, and also enables an advanced surgical operation to be performed with use of a plurality of surgical instruments of different kinds.

<Configuration of Surgical Instrument Holding Device>

A configuration of the surgical instrument holding device 16 connected to the fourth movable body 15 will be described below (see FIGS. 4 to 19).

In some embodiments, the surgical instrument holding device 16 has a configuration in which a sixth movable body is supported in a rotatable manner by a fifth movable body. In the following description, in order to simplify the description, the forward and rearward, upward and downward, and leftward and rightward directions are indicated supposing that a direction in which the fifth movable body and the sixth movable body are present in a state in which the sixth movable body is supported on the lower side of the fifth movable body is an upward-downward direction, and supposing that the direction of a central axis as a reference of rotation of the sixth movable body is a forward-rearward direction. However, the forward and rearward, upward and downward, and leftward and rightward directions in the following are directions for the convenience of description, and are not limited to these directions.

Figure 4:
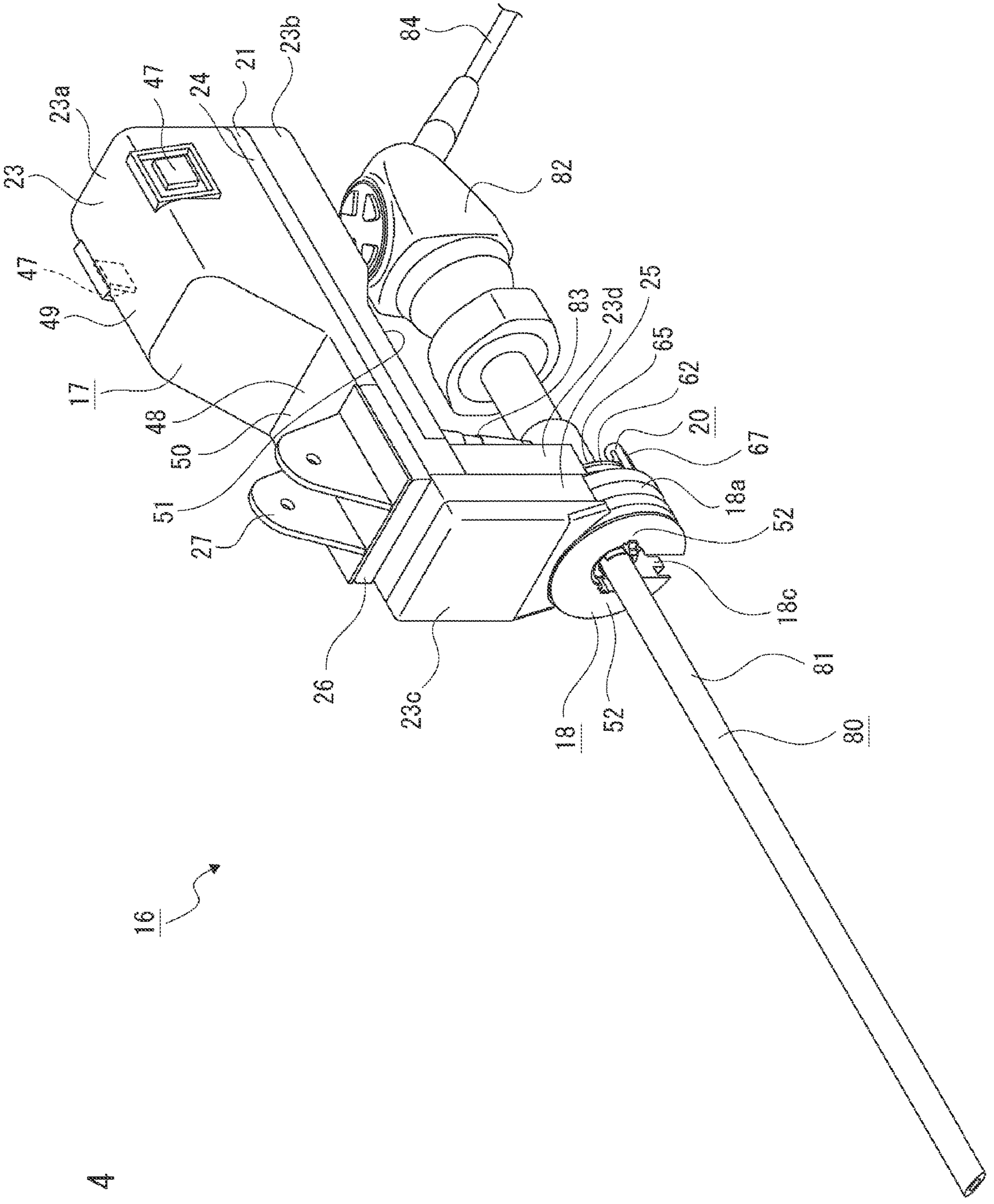
FIG. 4 is a perspective view of the surgical instrument holding device and a surgical instrument, according to some embodiments.
Figure 5:
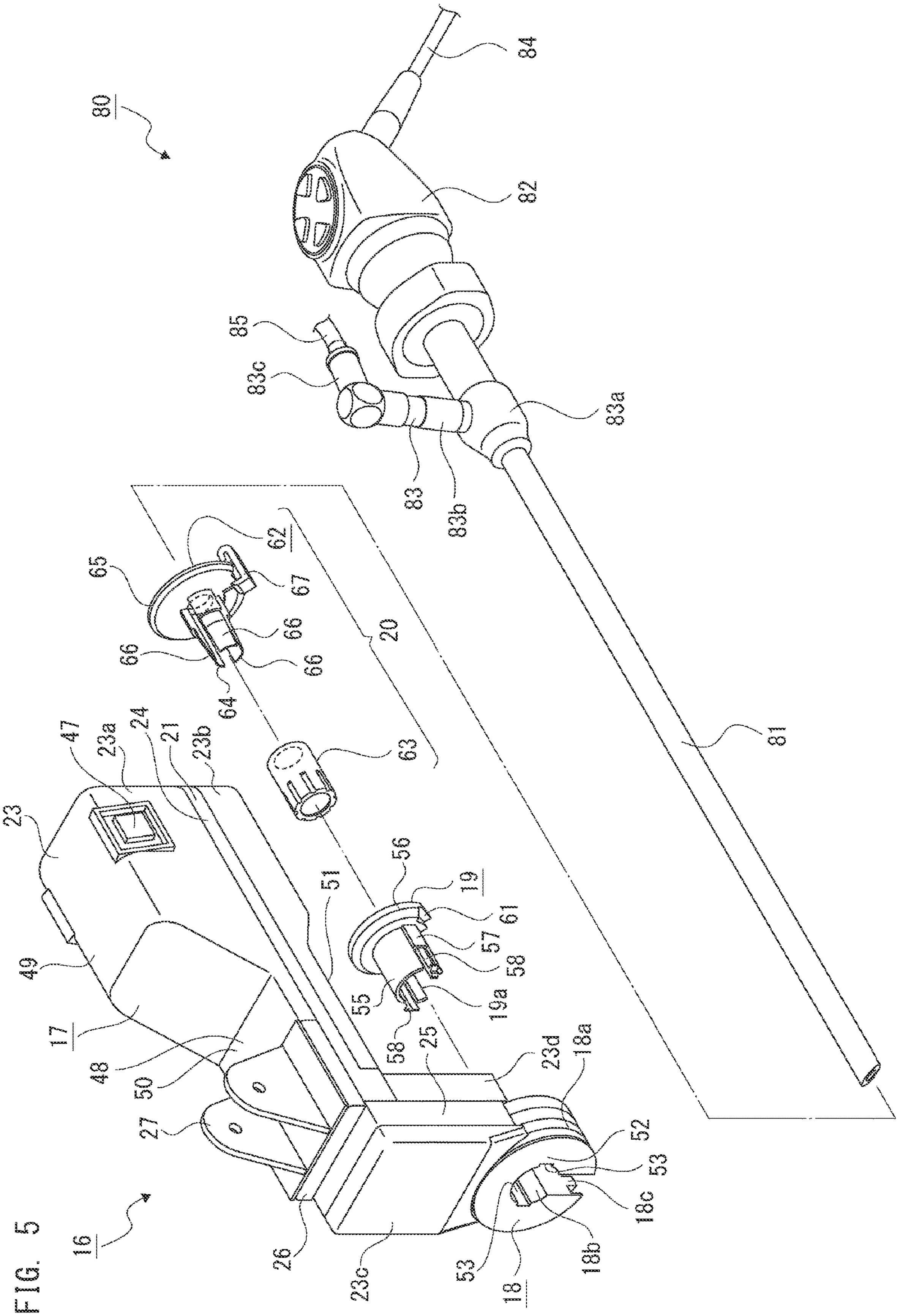
FIG. 5 is an exploded perspective view of the surgical instrument holding device and the surgical instrument, according to some embodiments.
Figure 6:
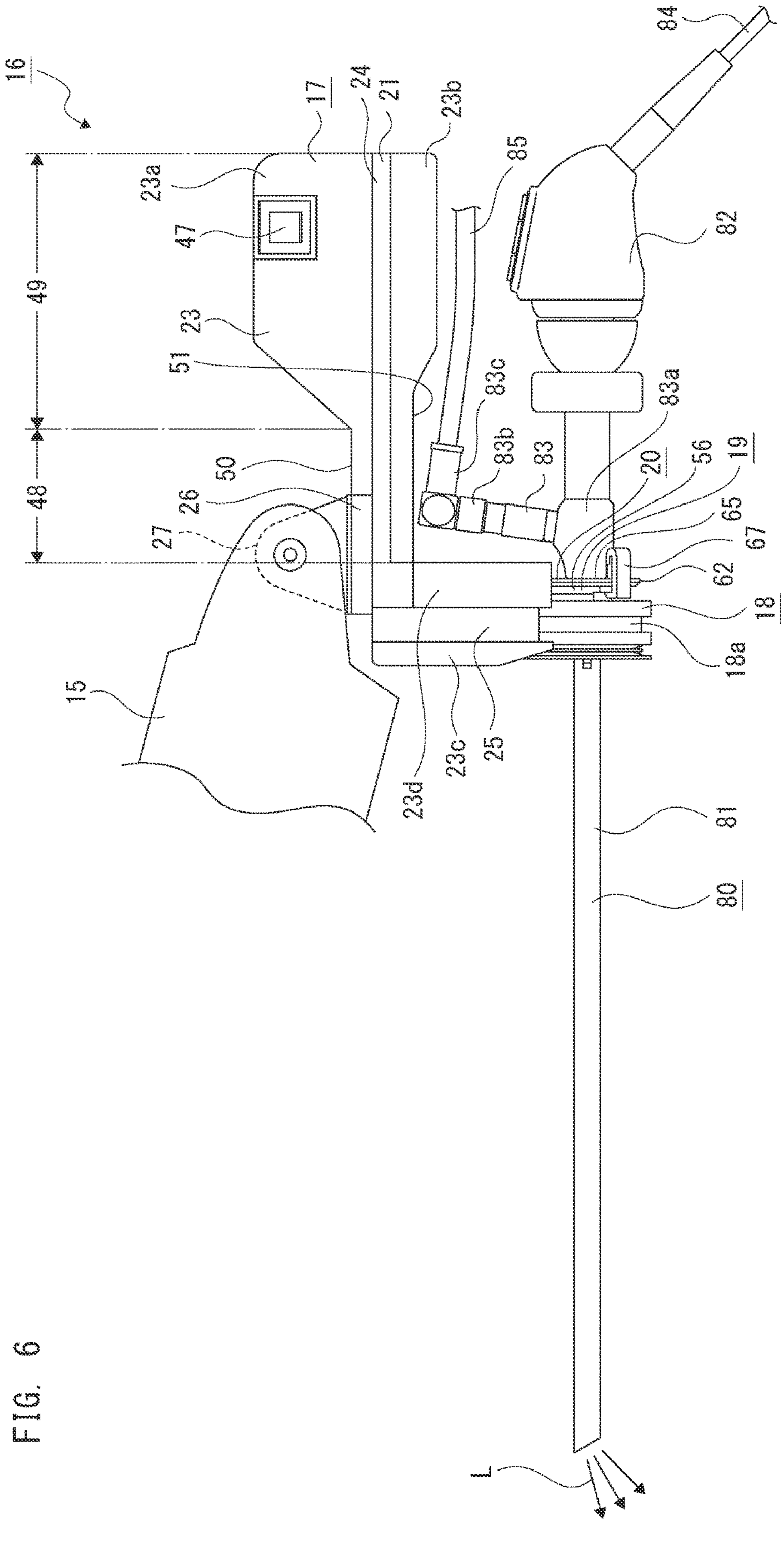
FIG. 6 is a side view of the surgical instrument holding device, according to some embodiments.

As described above, the surgical instrument holding device 16 is connected rotatably to the distal end side connecting portion 15*b* of the fourth movable body 15 (see FIGS. 4 to 6). The surgical instrument holding device 16 includes a driving body 17 that is connected rotatably to the fourth movable body 15 and that functions as the fifth movable body, a holding body 18 that is supported in a rotatable manner by the driving body 17 and that functions as the sixth movable body, a separator 19 detachable from the holding body 18, and an adapter 20 detachable from the separator 19.

(Configuration of Driving Body and Detecting Mechanism)

The driving body 17 includes a bracket 21, a driving force transmitting mechanism 22, and a housing case 23. The driving force transmitting mechanism 22 is supported by the bracket 21. The driving force transmitting mechanism 22 is housed in the housing case 23 (see FIGS. 6 to 8).

The bracket 21 includes a first supporting member 24 extending in the forward-rearward direction and a second supporting member 25 extending in the upward-downward direction. An upper end portion of the second supporting member 25 is attached to a front end portion of the first supporting member 24. A coupling member 26 is attached to the upper surface of the front end portion of the first supporting member 24. An unillustrated shaft insertion hole which penetrates the bracket 21 in the forward-rearward direction is formed in an upper end portion in a front end portion of the bracket 21.

The second supporting member 25 has a supporting portion 25*a* at a lower end portion thereof, which is formed in the shape of an upwardly projecting circular arc. The second supporting member 25 has guiding projecting portions 25*b* projecting downward from the inner peripheral surface of the supporting portion 25*a* in such a manner as to be separated from each other in a circumferential direction.

A connecting member 27 connected to the distal end side connecting portion 15*b* of the fourth movable body 15 is attached to the coupling member 26. Because the connecting member 27 is connected to the distal end side connecting portion 15*b*, the driving body 17 is, for example, rotated with respect to the fourth movable body 15 in an axial rotation direction about a reference axis extending in a direction orthogonal to the connecting direction in which the driving body 17 and the fourth movable body 15 are connected to each other. Hence, because the driving body 17 functioning as the fifth movable body is rotated with respect to the fourth movable body 15, the surgery assisting device 1 has one degree of freedom in an operating direction.

The driving body 17 functioning as the fifth movable body is rotated by the driving force of an unillustrated electric actuator or pneumatic actuator.

Figure 7:
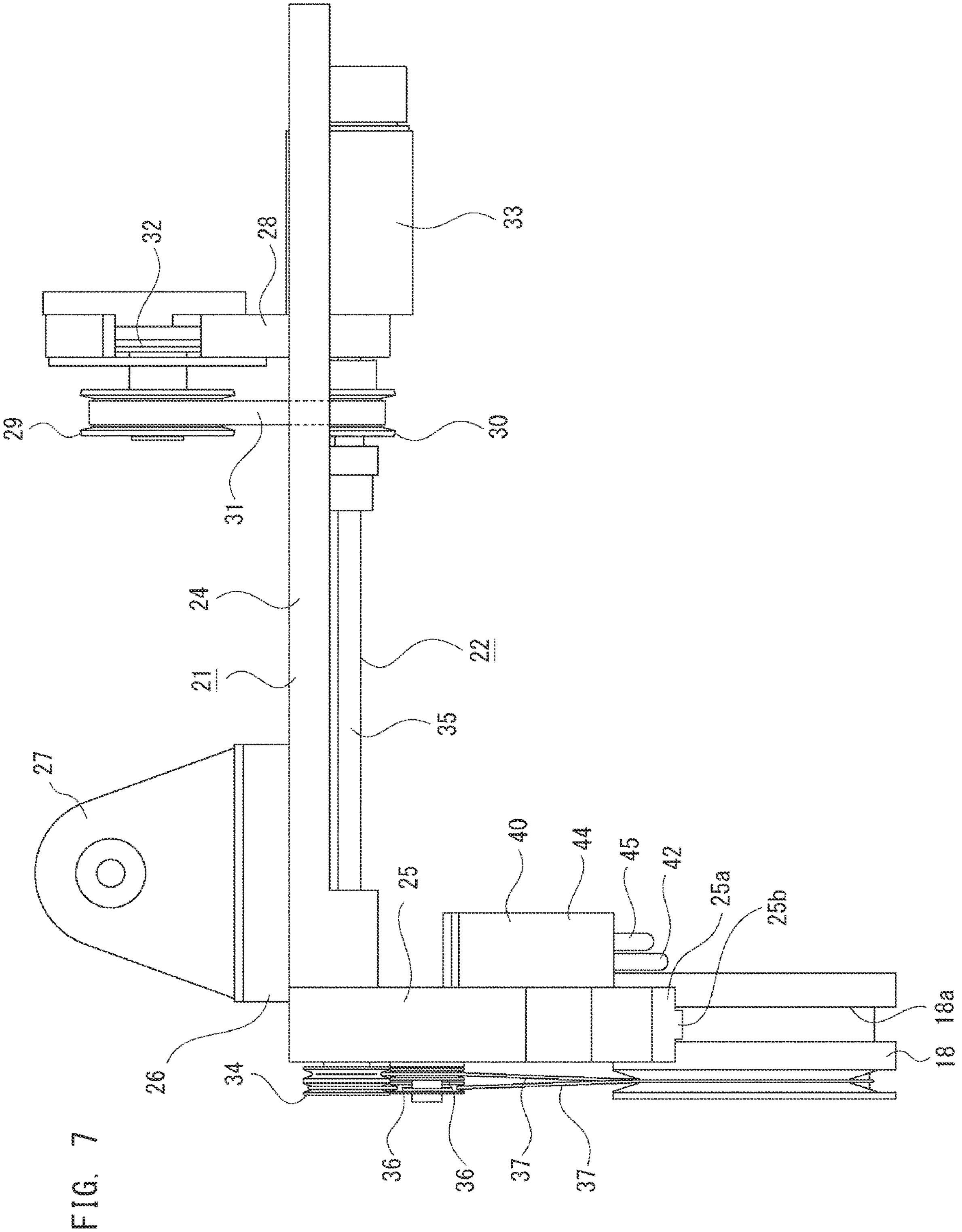
FIG. 7 is a side view illustrating an internal structure of a driving body, according to some embodiments.

A lower end portion of a third supporting member 28 is attached to a position close to a rear end of the first supporting member 24 (see FIG. 7). An unillustrated belt insertion hole which is made to penetrate the first supporting member 24 in the upward-downward direction is formed in the first supporting member 24 at a position immediately in front of the third supporting member 28.

The driving force transmitting mechanism 22 has belt pulleys 29 and 30. The belt pulleys 29 and 30 are supported on the front surface of the third supporting member 28 in such a manner as to be separated from each other in the upward-downward direction. A transmission belt 31 is wound between the belt pulleys 29 and 30 through the belt insertion hole of the first supporting member 24. An encoder 32 that detects the rotational angle of the belt pulley 29 on the upper side is disposed in the front surface of the third supporting member 28.

A driving motor 33 is attached to the lower surface of a rear end portion of the first supporting member 24. A motor shaft of the driving motor 33 is fixed to a central portion of the belt pulley 30 on the lower side. Hence, when the driving motor 33 is rotated, a driving force is transmitted to the belt pulley 29 on the upper side via the belt pulley 30 on the lower side and the transmission belt 31. When the belt pulley 29 is rotated, the rotational position of the belt pulley 29 is detected by the encoder 32.

The driving force transmitting mechanism 22 includes a pulley 34, a connecting shaft 35, and intermediate pulleys 36.

Figure 8:
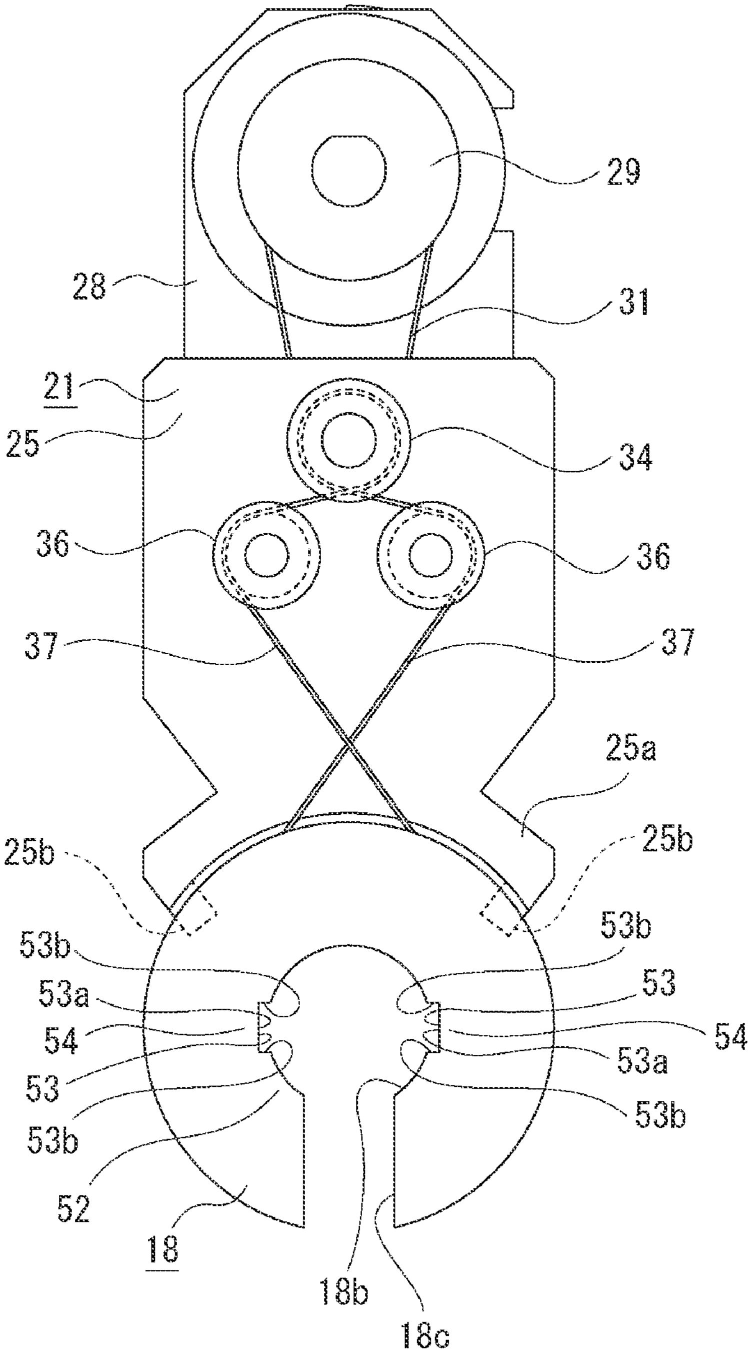
FIG. 8 is a front view of the driving body and a holding body, according to some embodiments.

The pulley 34 is supported by the front surface of the upper end portion of the second supporting member 25 (see FIG. 7 and FIG. 8). The pulley 34 is connected to the belt pulley 30 on the lower side by the connecting shaft 35. The connecting shaft 35 is inserted through the shaft insertion hole formed in the bracket 21, and is connected to the belt pulley 30 on the lower side. Hence, a rotational force of the belt pulley 30 is transmitted to the pulley 34 via the connecting shaft 35. The intermediate pulleys 36 are supported by the front surface of the second supporting member 25 in a state in which the intermediate pulleys 36 are separated from each other in a left-right direction. The intermediate pulleys 36 are positioned on the lower side of the pulley 34.

Driving wires 37 are wound around the pulley 34 and the intermediate pulleys 36. In a state in which one driving wire 37 is wound around one intermediate pulley 36, one end portion of the one driving wire 37 is fixed to the pulley 34, and the other end portion of the one driving wire 37 is fixed to the holding body 18. In a state in which the other driving wire 37 is wound around the other intermediate pulley 36, one end portion of the other driving wire 37 is fixed to the pulley 34, and the other end portion of the other driving wire 37 is fixed to the holding body 18. Hence, when the driving wires 37 are fed by rotation of the pulley 34, the holding body 18 is rotated in a direction corresponding to the feed direction of the driving wires 37.

Figure 9:
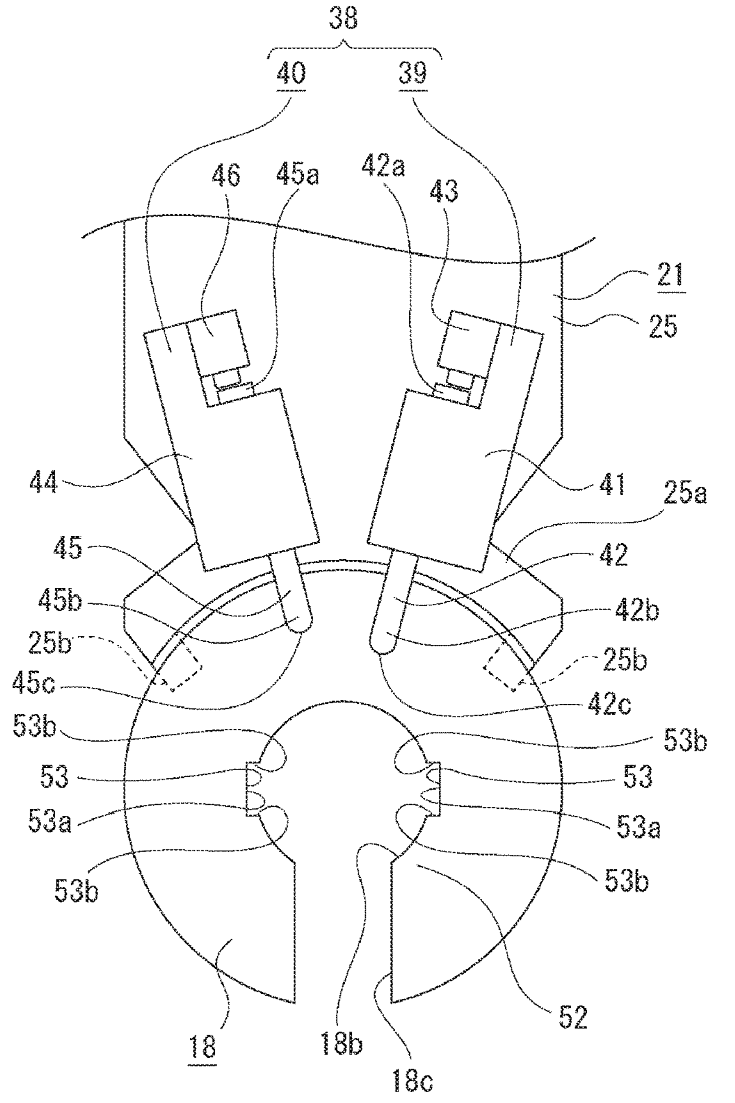
FIG. 9 is a rear view of a detecting mechanism and the holding body, according to some embodiments.
Figure 10:
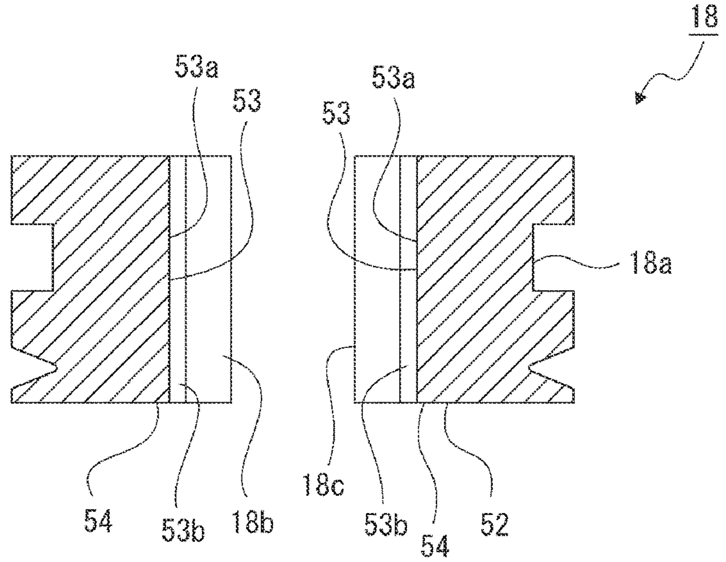
FIG. 10 is a sectional view of the holding body, according to some embodiments.

A detecting mechanism 38 is disposed on the rear surface of the second supporting member 25 (see FIG. 7 and FIG. 9). The detecting mechanism 38 includes a first detecting unit 39 and a second detecting unit 40. The first detecting unit 39 and the second detecting unit 40 are arranged on the second supporting member 25 in a state in which the first detecting unit 39 and the second detecting unit 40 are separated from each other in the rotational direction of the holding body 18.

The first detecting unit 39 has a function of detecting a state of attachment of the separator 19 to the holding body 18. The second detecting unit 40 has a function of detecting a state of attachment of the adapter 20 to the separator 19.

As described above, the first detecting unit 39 and the second detecting unit 40 are arranged on the bracket 21 in a state in which the first detecting unit 39 and the second detecting unit 40 are separated from each other in the rotational direction of the holding body 18. Thus, the first detecting unit 39 and the second detecting unit 40 are positioned in a state of being side by side on the same surface of the bracket 21. The surgery assisting device 1 can therefore be downsized by effective utilization of a space in the bracket 21.

The first detecting unit 39 includes a main body section 41 attached to the second supporting member 25, a detecting pin 42 moved with respect to the main body section 41, and a detecting switch 43 attached to the second supporting member 25.

The detecting pin 42 is disposed in a state of extending in the radial direction of the holding body 18, and is moved with respect to the main body section 41 in a direction of separating from or approaching the center of the holding body 18. Both an upper end portion and a lower end portion of the detecting pin 42 respectively project upward and downward from the main body section 41. The detecting pin 42 has an operating portion 42*a* at an upper end portion thereof and has an action target portion 42*b* at the lower end portion thereof. The action target portion 42*b* has a distal end portion formed in a hemispherical shape and has a distal end surface formed as a spherical surface portion 42*c* protruding to a distal end side.

The detecting pin 42 is biased by an unillustrated spring in a direction of moving downward with respect to the main body section 41. The action target portion 42*b* is positioned downward of a lower edge of the supporting portion 25*a* in the second supporting member 25.

The detecting switch 43 is positioned on the upper side of the operating portion 42*a* in the detecting pin 42. In a state in which no upward moving force is applied to the detecting pin 42, the detecting switch 43 is set in an off state with the detecting pin 42 positioned at a lower movement end and with the operating portion 42*a* distanced downward from the detecting switch 43, and the action target portion 42*b* is positioned downward of the lower edge of the supporting portion 25*a* in the second supporting member 25. When the detecting pin 42 is moved upward against a biasing force of the spring, the detecting switch 43 is operated and set in an on state by the operating portion 42*a*, and a detection signal is sent out to an unillustrated detecting circuit.

The second detecting unit 40 includes a main body section 44 attached to the second supporting member 25, a detecting pin 45 moved with respect to the main body section 44, and a detecting switch 46 attached to the second supporting member 25.

The detecting pin 45 is disposed in a state of extending in the radial direction of the holding body 18, and is moved with respect to the main body section 44 in a direction of separating from or approaching the center of the holding body 18. Both an upper end portion and a lower end portion of the detecting pin 45 respectively project upward and downward from the main body section 44. The detecting pin 45 has an operating portion 45*a* at an upper end portion thereof and has an action target portion 45*b* at lower end portion thereof. The action target portion 45*b* has a distal end portion formed in a hemispherical shape and has a distal end surface formed as a spherical surface portion 45*c* protruding to a distal end side.

The detecting pin 45 is biased by an unillustrated spring in a direction of moving downward with respect to the main body section 44. The action target portion 45*b* is positioned downward of the lower edge of the supporting portion 25*a* in the second supporting member 25. The detecting pin 45 of the second detecting unit 40 is positioned slightly rearward of the detecting pin 42 of the first detecting unit 39.

The detecting switch 46 is positioned on the upper side of the operating portion 45*a* in the detecting pin 45. In a state in which no upward moving force is applied to the detecting pin 45, the detecting switch 46 is set in an off state with the detecting pin 45 positioned at a lower movement end and with the operating portion 45*a* distanced downward from the detecting switch 46, and the action target portion 45*b* is positioned downward of the lower edge of the supporting portion 25*a* in the second supporting member 25. When the detecting pin 45 is moved upward against a biasing force of the spring, the detecting switch 46 is operated and set in an on state by the operating portion 45*a*, and a detection signal is sent out to the unillustrated detecting circuit.

The housing case 23 is, for example, divided into four parts, and includes a first case portion 23*a*, a second case portion 23*b*, a third case portion 23*c*, and a fourth case portion 23*d* (see FIGS. 4 to 6). The housing case 23 is, for example, formed by a resin material. When the housing case 23 is formed by a resin material, a reduction in weight of the driving body 17 can be achieved, a load on operation of the driving body 17 is consequently suppressed, and smooth rotational operation of the driving body 17 with respect to the fourth movable body 15 can therefore be performed.

The first case portion 23*a* is attached from an upper side to the first supporting member 24 on the rear side of the coupling member 26. The first case portion 23*a* covers the belt pulley 29, the third supporting member 28, and the like.

Manual switches 47 are respectively arranged on both side surfaces of the first case portion 23*a*. The driving body 17, for example, can be rotated with respect to the fourth movable body 15 by manual operation of the manual switches 47. The driving body 17 is rotated in one direction by operation of one manual switch 47. The driving body 17 is rotated in another direction by operation of the other manual switch 47. In some embodiments, a configuration may be adopted in which the driving motor 33 is rotated to rotate the holding body 18 with respect to the driving body 17 by manual operation of the manual switches 47. The manual switches 47 are, for example, operated by an operator or an assistant present in the operating room.

The second case portion 23*b* is attached to the first supporting member 24 from a lower side. The second case portion 23*b* covers the belt pulley 30, the connecting shaft 35, and the like.

The third case portion 23*c* is attached to the second supporting member 25 from the front. The third case portion 23*c* covers the pulley 34, the intermediate pulleys 36, and the like. An unillustrated part insertion hole which penetrates the third case portion 23*c* in the upward-downward direction is formed in a lower end portion of the third case portion 23*c*. The driving wires 37 are drawn out downward from the inside of the third case portion 23*c* through the part insertion hole, and are fixed to the holding body 18.

The fourth case portion 23*d* is attached to the second supporting member 25 from the rear. The fourth case portion 23*d* covers the detecting mechanism 38 and the like. An unillustrated part insertion hole which penetrates the fourth case portion 23*d* in the upward-downward direction is formed in a lower end portion of the fourth case portion 23*d*. The detecting pin 42 of the first detecting unit 39 and the detecting pin 45 of the second detecting unit 40 are drawn out downward from the inside of the fourth case portion 23*d* through the part insertion hole.

The driving body 17 configured as described above is formed in substantially the shape of an L laid sideways as a whole. A part of the driving body 17 which part extends in the forward-rearward direction includes a narrow width portion 48 having a small vertical width and a wide width portion 49 having a larger vertical width than the narrow width portion 48.

The connecting shaft 35 is disposed inside the narrow width portion 48. The belt pulleys 29 and 30, the driving motor 33, and the like are arranged inside the wide width portion 49. The wide width portion 49 is formed in a shape of a large vertical width because the wide width portion 49 is a part in which the belt pulleys 29 and 30, the driving motor 33, and the like are arranged. The narrow width portion 48 is continuous with a part close to a lower end of the wide width portion 49. A first recess-shaped space 50 that opens upward is formed on the upper side of the narrow width portion 48. A second recess-shaped space 51 that opens downward is formed on the lower side of the narrow width portion 48.

(Configuration of Holding Body)

The holding body 18 is supported in a rotatable manner by the driving body 17, and functions as the sixth movable body. The holding body 18 is supported in a rotatable manner by the supporting portion 25*a* of the second supporting member 25 (see FIGS. 4 to 8).

The holding body 18 is formed in a substantially circular arc shape. The holding body 18 has a guided groove 18*a* in an outer circumferential portion thereof, the guided groove 18*a* opening outward and extending in a circumferential direction. The holding body 18 has at a central portion thereof an insertion hole 18*b* that penetrates the holding body 18 in the forward-rearward direction.

The holding body 18 has a substantially circular arc shape formed in a shape of approximately 270 degrees to 330 degrees, for example, in the circumferential direction. A space between both ends of the holding body 18 in the circumferential direction is formed as an insertion and extraction hole 18*c*. The insertion and extraction hole 18*c* communicates with the insertion hole 18*b*.

An inner circumferential portion of the holding body 18 is provided as a holding portion 52 that holds the surgical instrument via the separator 19 and the adapter 20. Insertion portions 53 that open in a direction of facing each other are formed at positions 180 degrees opposite each other in the holding portion 52. The insertion portions 53 are formed at positions separated from the insertion and extraction hole 18*c* by 90 degrees in the circumferential direction. The insertion portions 53 communicate with the insertion hole 18*b*.

Figure 11:
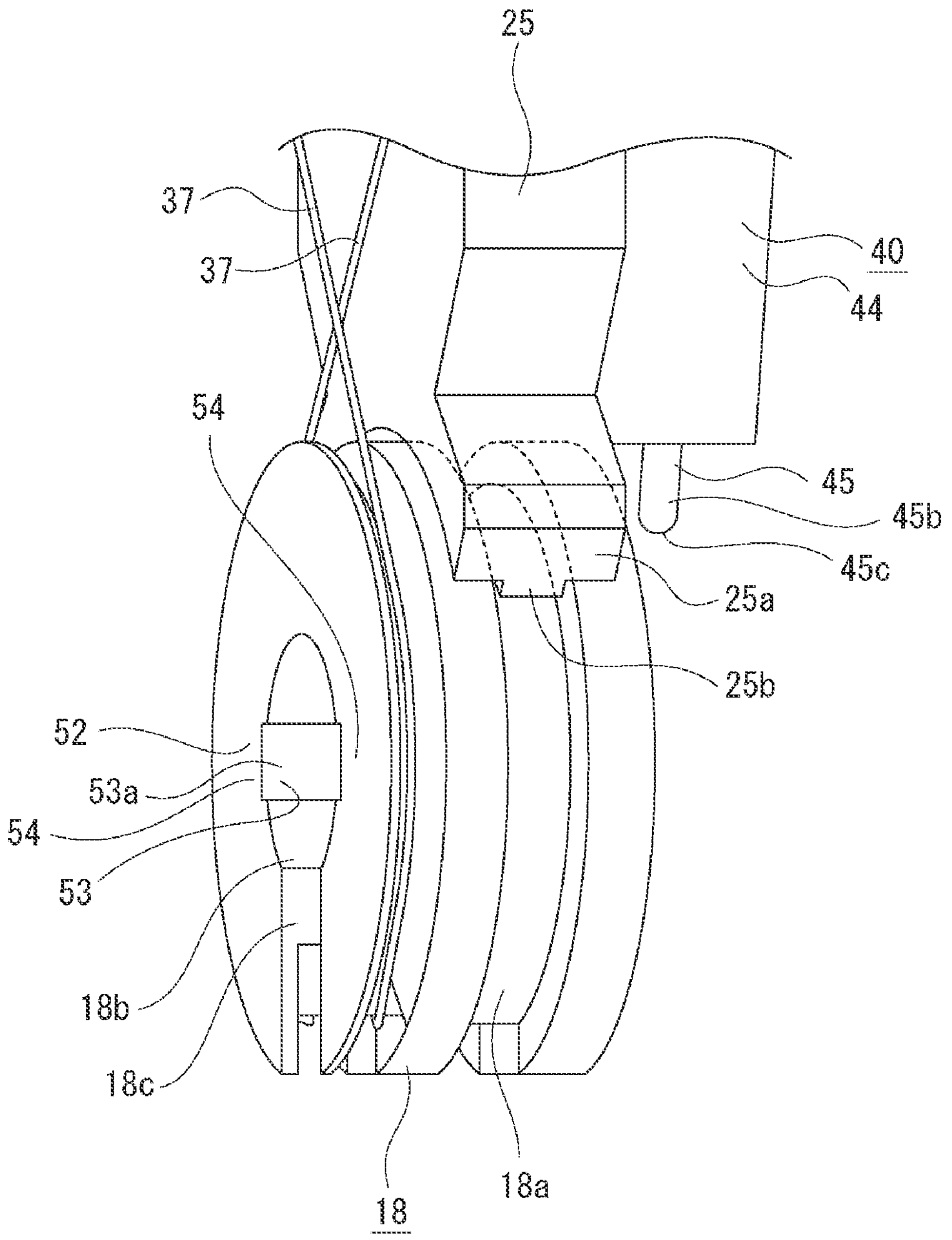
FIG. 11 is a perspective view of the holding body, according to some embodiments.
Figure 12:
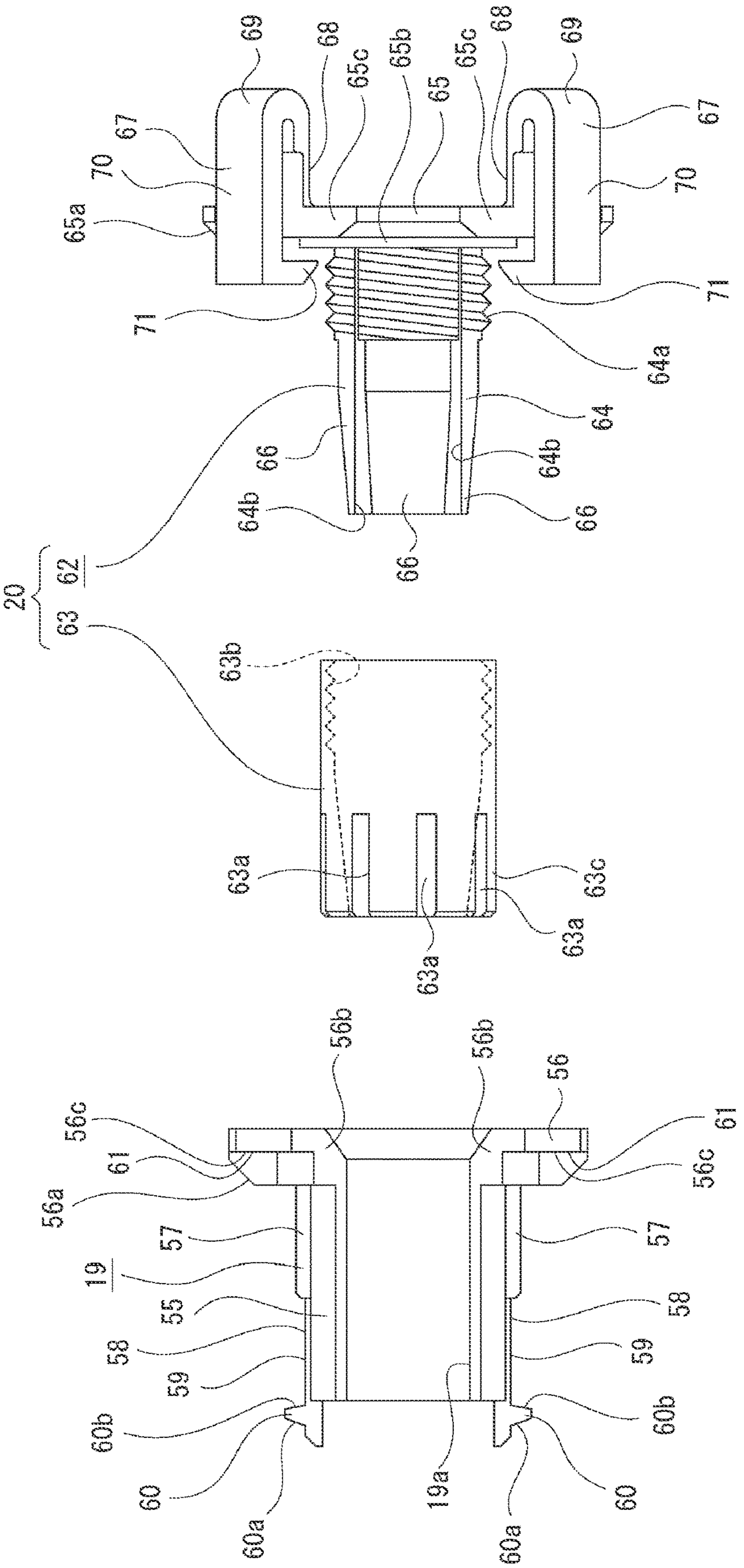
FIG. 12 is a bottom view illustrating a separator and an adapter in a disassembled state, according to some embodiments.
Figure 13:
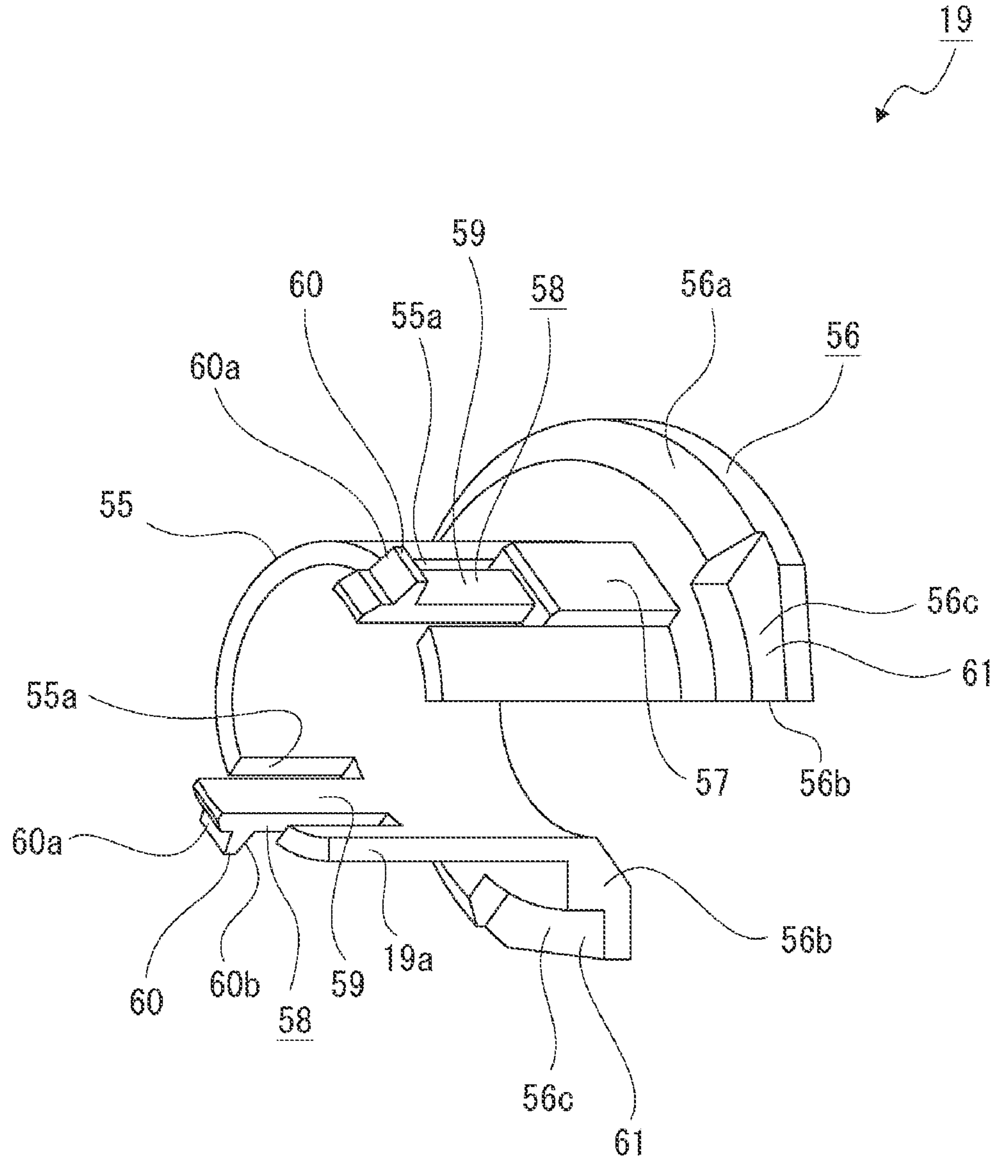
FIG. 13 is a perspective view of the separator, according to some embodiments.
Figure 14:
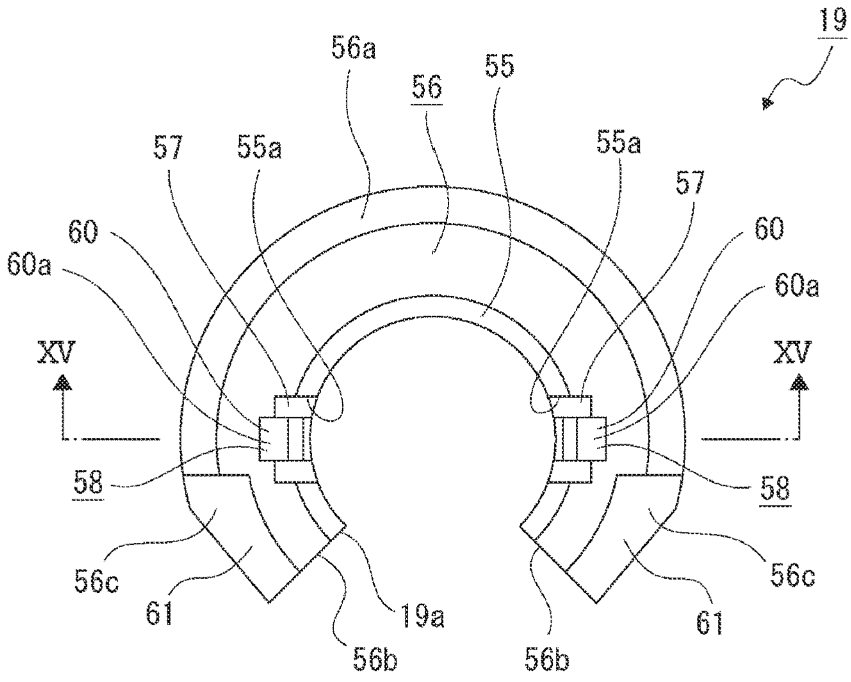
FIG. 14 is a front view of the separator, according to some embodiments.
Figure 15:
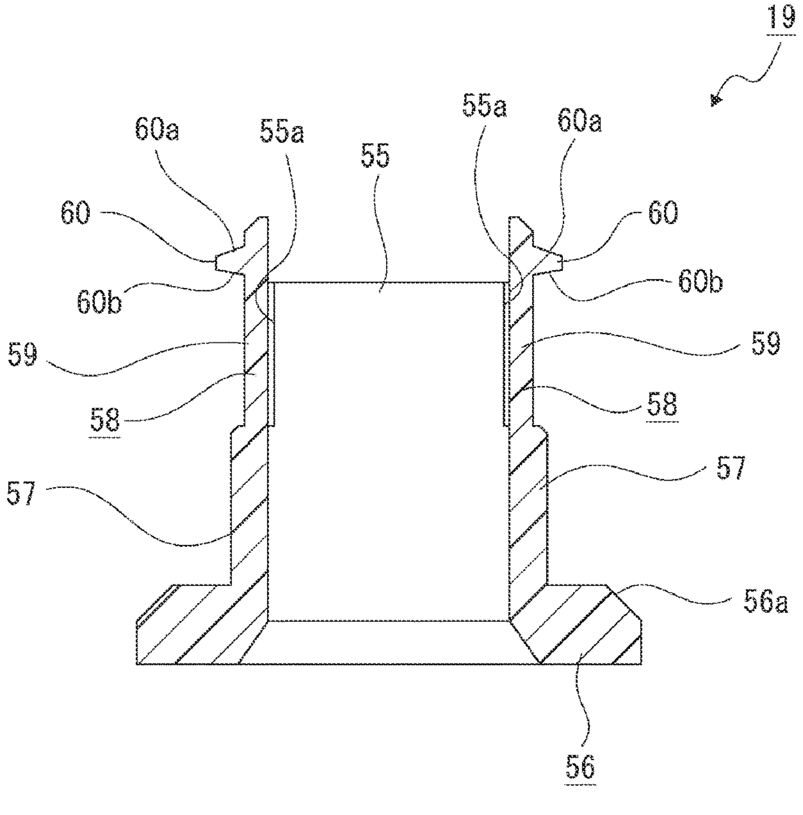
FIG. 15 is a sectional view taken along line XV-XV of FIG. 14.
Figure 16:
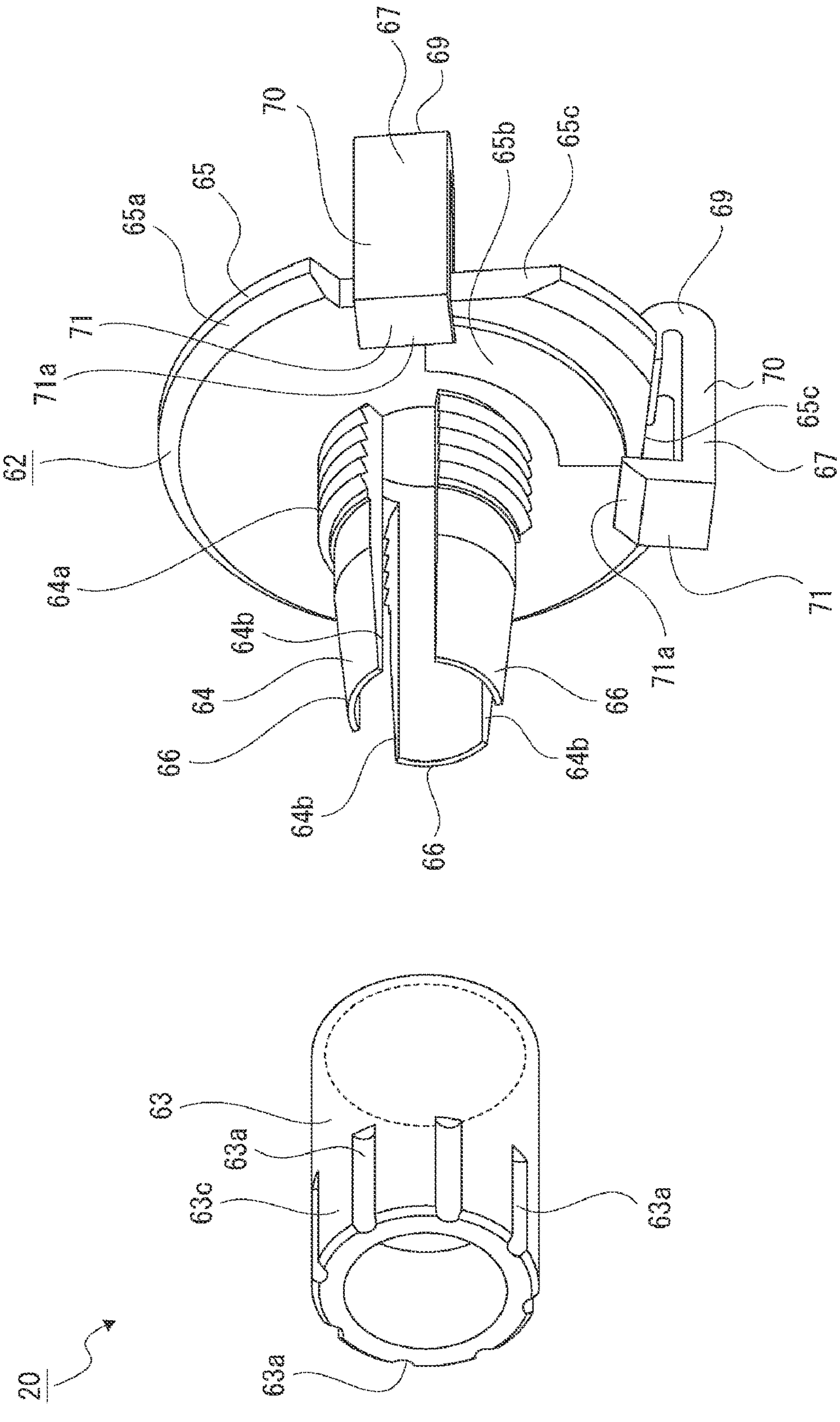
FIG. 16 is an exploded perspective view of the adapter, according to some embodiments.
Figure 17:
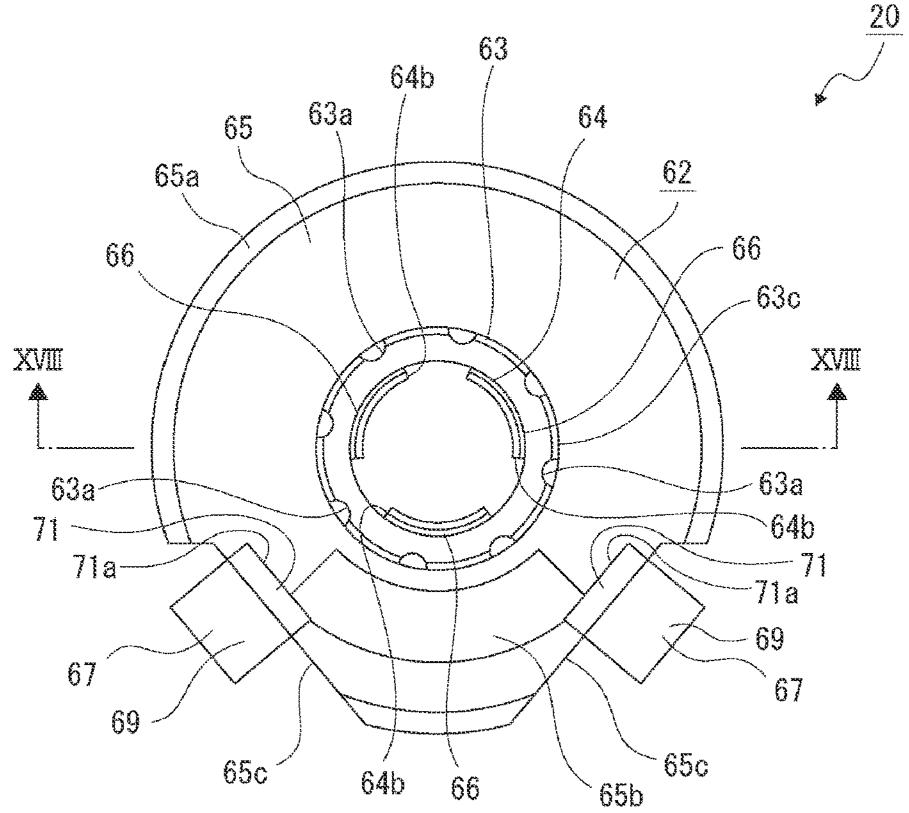
FIG. 17 is a front view of the adapter, according to some embodiments.
Figure 18:
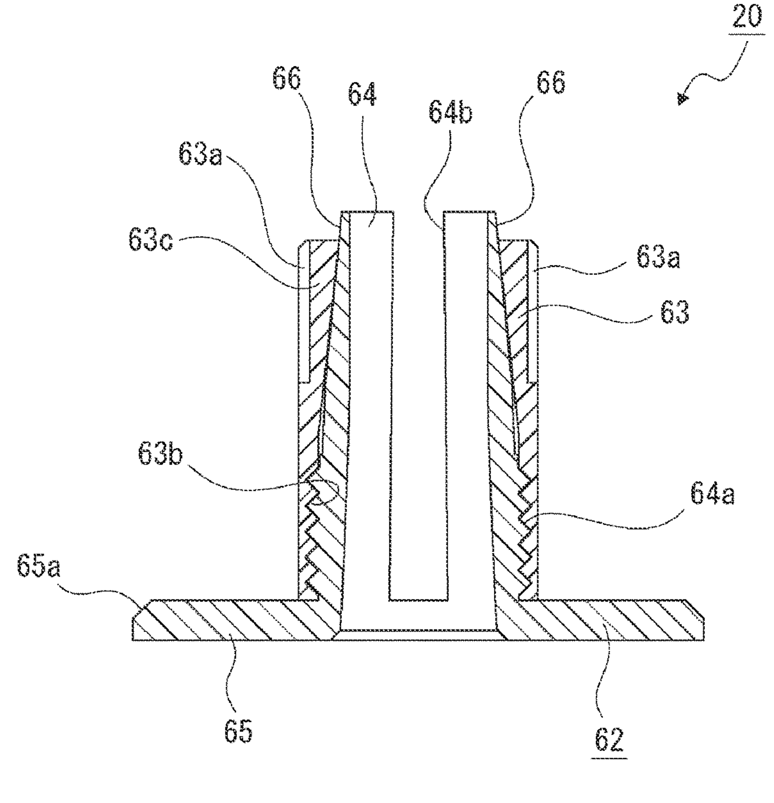
FIG. 18 is a sectional view taken along line XVIII-XVIII of FIG. 17.

Of surfaces forming the insertion portions 53, surfaces facing each other in the left-right direction are respectively formed as sliding portions 53*a* (see FIG. 8 and FIG. 11). In some embodiments, of the surfaces forming the insertion portions 53, surfaces continuous with the sliding portions 53*a* and facing each other in the upward-downward direction are formed as rotation restricting portions 53*b*.

Front side opening edges of the insertion portions 53 in the holding body 18 are respectively formed as first engagement receiving portions 54.

The guiding projecting portions 25*b* of the second supporting member 25 are inserted in the guided groove 18*a* of the holding body 18, and the holding body 18 is rotated with respect to the driving body 17 while being guided by the guiding projecting portions 25*b*. Although not illustrated, in some embodiments, the guiding projecting portions 25*b* may be formed in a shape of suspending the holding body 18, and thus also have a function of preventing the holding body 18 from falling off the driving body 17.

The holding body 18 is, for example, rotated with respect to the driving body 17 in an axial rotation direction about a reference axis extending in a direction orthogonal to the connecting direction in which the holding body 18 and the driving body 17 are connected to each other. Hence, because the holding body 18 functioning as the sixth movable body is rotated with respect to the driving body 17 functioning as the fifth movable body, the surgery assisting device 1 has one degree of freedom in an operating direction.

As described above, the surgery assisting device 1 has six degrees of freedom in operating directions because the first movable body 7 is rotated with respect to the second connecting arm 6, the second movable body 8 is rotated with respect to the first movable body 7, the third movable body 12 is rotated with respect to the intermediate connecting member 11, the fourth movable body 15 is rotated with respect to the third movable body 12, the driving body 17 is rotated with respect to the fourth movable body 15, and the holding body 18 is rotated with respect to the driving body 17.

The holding body 18 is rotated by the driving force of the driving motor 33. Specifically, when the driving motor 33 is rotated, the belt pulley 30 to which the motor shaft is fixed is rotated. As the belt pulley 30 is rotated, the belt pulley 29 is rotated via the transmission belt 31, and the pulley 34 is rotated via the connecting shaft 35. The driving wires 37 are fed by the rotation of the pulley 34 via the intermediate pulleys 36. The holding body 18 is consequently rotated in a direction corresponding to the feed direction of the driving wires 37. At this time, the rotational position of the belt pulley 29 is detected by the encoder 32, and the rotational angle (rotational position) of the holding body 18 with respect to the driving body 17 is calculated.

(Configuration of Separator)

A part of a drape for separating a clean region and an unclean region from each other is attached to the separator 19. The drape separates the clean region in which the patient 200 is present and the unclean region in which the surgery assisting device 1 is present.

The parts of the separator 19 are integrally formed by a resin material. The separator 19 includes an insertion portion 55 in which the forward-rearward direction is set as an axial direction thereof and a flange-shaped receiving portion 56 that projects outward from a rear edge of the insertion portion 55 (see FIGS. 12 to 15).

The insertion portion 55 is in substantially the shape of a circular arc surface formed in a shape of approximately 200 degrees to 300 degrees, for example, in the circumferential direction. Formation notches 55*a* that open forward are formed at positions 180 degrees opposite each other in the circumferential direction in a front half part of the insertion portion 55.

The separator 19 is provided with rotation restricted portions 57 that protrude from the outer circumferential surface of the insertion portion 55. The rotation restricted portions 57 are provided at positions 180 degrees opposite each other in the circumferential direction of the insertion portion 55, and protrude outward from a rear half part of the insertion portion 55. The rotation restricted portions 57 are parts inserted into the insertion portions 53 when the separator 19 is attached to the holding body 18. The rotation restricted portions 57 are formed in a substantially rectangular parallelepipedic shape.

The separator 19 is provided with first engaging portions 58 each continuous with the rotation restricted portions 57. The first engaging portions 58 are positioned in the formation notches 55*a* of the insertion portion 55, and are elastically deformable with respect to the rotation restricted portions 57 in the radial direction of the insertion portion 55.

Thus, in the separator 19, the rotation restricted portions 57 and the first engaging portions 58 are provided in such a manner as to be continuous with each other. Hence, because the rotation restricted portions 57 and the first engaging portions 58 both in a shape of protruding with respect to the insertion portion 55 are not provided at positions separated from each other in the separator 19, a die can be formed in a simple structure in a case where the separator 19 is formed by injection molding, and the separator 19 can thereby be formed easily.

The first engaging portions 58 include a deforming portion 59 projecting forward from the front surface of the rotation restricted portion 57 and a protruding portion 60 protruding outward from a front end portion of the deforming portion 59. The protruding portion 60 is formed in substantially the shape of a triangular prism tapered as the protruding portion 60 separates outward from the deforming portion 59. A front side surface of the protruding portion 60 is formed as a sliding inclined surface 60*a*. A rear side surface of the protruding portion 60 is formed as an engaging surface 60*b*. The sliding inclined surface 60*a* is formed as an inclined surface that approaches a front end of the deforming portion 59 toward the front. The engaging surface 60*b* is formed as a surface facing rearward. The protruding portion 60 of the first engaging portion 58 is positioned forward of a front end of the insertion portion 55.

The receiving portion 56 is in substantially the shape of a circular arc surface formed in a shape of approximately 200 degrees to 300 degrees, for example, in the circumferential direction in such a manner as to correspond to the insertion portion 55. An inclined surface 56*a* displaced to an inner circumferential side toward the front is formed on an outer circumferential portion of the receiving portion 56. Both end edges in the circumferential direction of the receiving portion 56 are formed as restricting portions 56*b*.

Both end portions in the circumferential direction of the receiving portion 56 are provided with second engagement receiving portions 61. The second engagement receiving portions 61 are formed in a shape having a smaller thickness than another part, with recessed portions 56*c* formed in portions of front side parts in the receiving portion 56.

As described above, the insertion portion 55 and the receiving portion 56 of the separator 19 are in substantially the shape of a circular arc formed in a shape of approximately 200 degrees to 300 degrees, for example, in the circumferential direction. A space between both ends of the separator 19 in the circumferential direction is formed as an insertion and extraction opening 19*a*.

(Configuration of Adapter)

In order to make the surgical instrument held by the holding body 18 via the separator 19, the adapter 20 is formed in sizes and shapes corresponding to various kinds of surgical instruments of different sizes and shapes, and are formed with a structure that is properly attached to the separator 19.

The adapter 20 includes an insertion member 62 and an attachment member 63 (see FIG. 12, FIG. 16, FIG. 17, and FIG. 18).

The parts of the insertion member 62 is integrally formed by a resin material. The insertion member 62 includes a tubular portion 64 in which the forward-rearward direction is an axial direction thereof and a flange-shaped pressing portion 65 that projects outward from a rear edge of the tubular portion 64.

The tubular portion 64 is formed in a substantially cylindrical shape. The tubular portion 64 has a spiral groove 64*a* in the outer circumferential surface of a rear half portion of the tubular portion 64. Slits 64*b* opening forward are formed in the tubular portion 64 in such a manner as to be separated from each other at equal intervals in the circumferential direction. The slits 64*b* are present also in parts in which the spiral groove 64*a* is formed. Parts between the slits 64*b* of the tubular portion 64 are respectively provided as fastening portions 66. The fastening portions 66 are elastically deformable in a direction of separating from or approaching the center of the tubular portion 64.

The pressing portion 65 is formed in a substantially annular shape. An inclined surface 65*a* displaced to an inner circumferential side toward the front is formed on an outer circumferential portion of the pressing portion 65.

A restricted portion 65*b* in a circular arc shape is provided to the front surface of the pressing portion 65. The restricted portion 65*b* is formed in a shape slightly protruding forward with respect to another part of the pressing portion 65. Notches 65*c* opening outward are formed in the pressing portion 65 in such a manner as to be separated from each other in the circumferential direction.

The adapter 20 is provided with second engaging portions 67 projecting from an outer circumferential portion of the pressing portion 65. The second engaging portions 67 project rearward from positions in the vicinity of the respective notches 65*c* in the rear surface of the pressing portion 65 (see FIG. 16, FIG. 17, and FIG. 19). A distance in the circumferential direction between the second engaging portions 67 is set to be the same as a distance in the circumferential direction between the second engagement receiving portions 61 of the separator 19. The second engaging portions 67 are positioned in such a manner as to be separated from each other by approximately 80 degrees to 120 degrees in the circumferential direction of the pressing portion 65.

The second engaging portions 67 include a proximal end portion 68 that is continuous with the pressing portion 65 and that extends in a direction of projecting from the pressing portion 65; a folded portion 69 continuous with the proximal end portion 68 and formed in a folded shape; an outside portion 70 continuous with the folded portion 69 and positioned such that a part of the outside portion is opposed to the proximal end portion 68; and an engaging pawl portion 71 continuous with the outside portion 70 and bent at a right angle with respect to the outside portion 70 in a direction of approaching the pressing portion 65.

A direction in which the proximal end portion 68, the folded portion 69, the outside portion 70, and the engaging pawl portion 71 of the second engaging portion 67 are continuous with each other is set as a length direction, and a direction that is orthogonal to the length direction and connects the inner circumferential surface and outer circumferential surface of each part to each other is set as a thickness direction. Hence, the width direction of the proximal end portion 68, the folded portion 69, the outside portion 70, and the engaging pawl portion 71 is a direction orthogonal to both the length direction and the thickness direction. The proximal end portion 68, the folded portion 69, the outside portion 70, and the engaging pawl portion 71 have the same width.

Figure 19:
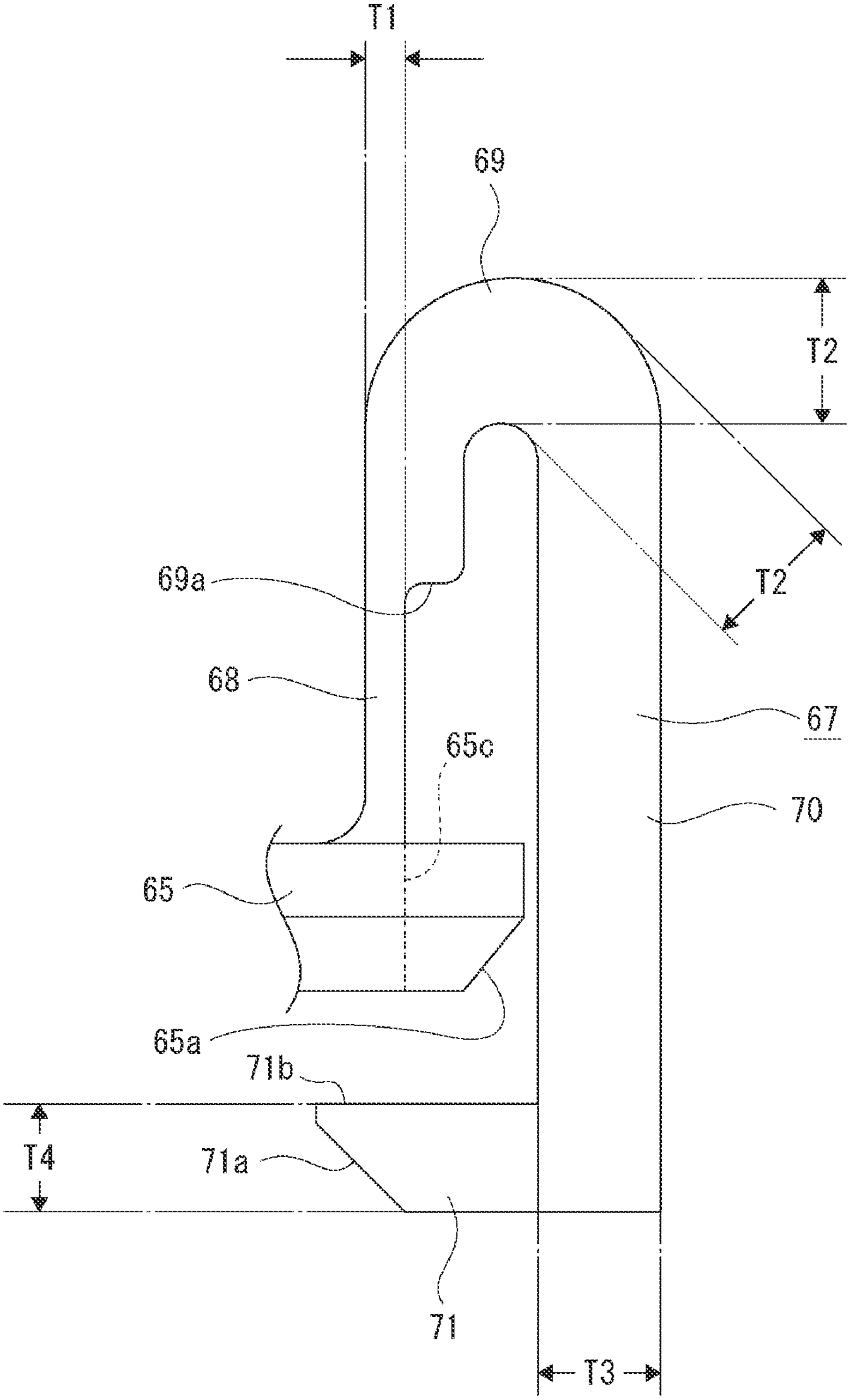
FIG. 19 is a plan view illustrating a second engaging portion, according to some embodiments.

The proximal end portion 68 has a thickness T1 smaller than the width, and is formed in a shape extending in the forward-rearward direction (see FIG. 19).

The folded portion 69 has a thickness T2 larger than the thickness T1 of the proximal end portion 68. The folded portion 69 is formed in a rearwardly protruding U-shape. A part of one front end surface of the folded portion 69 is continuous with the rear end surface of the proximal end portion 68. Because a part of the one front end face of the folded portion 69 is thus continuous with the rear end surface of the proximal end portion 68, a stepped surface 69*a* is formed at a boundary part between the folded portion 69 and the proximal end portion 68.

The outside portion 70 has a thickness T3 identical to the thickness T2 of the folded portion 69, and is formed in a shape extending in the forward-rearward direction. Hence, the thickness T3 of the outside portion 70 is larger than the thickness T1 of the proximal end portion 68. The outside portion 70 is positioned in a state of being parallel with the proximal end portion 68, and is formed in a shape extending in the forward-rearward direction.

The outside portion 70 has a length larger than that of the proximal end portion 68. The outside portion 70 is positioned from the rear side to the front side of the pressing portion 65 on the peripheral side of the pressing portion 65. A part of the outside portion 70 is positioned at the notch 65*c*.

Because the outside portions 70 are positioned on the peripheral side of the pressing portion 65, the external shape of the adapter 20 tends to be correspondingly large. However, the notches 65*c* are formed in the pressing portion 65, and the outside portions 70 are respectively positioned at the notches 65*c*. Hence, although the outside portions 70 are positioned on the peripheral side of the pressing portion 65, the notches 65*c* are formed, and the external shape of the adapter 20 is made correspondingly smaller, so that downsizing is achieved.

The engaging pawl portion 71 projects from a front end portion of the outside portion 70 to the tubular portion 64 side. The engaging pawl portion 71 has a thickness T4 identical to the thickness T3 of the outside portion 70. Hence, the thickness T4 of the engaging pawl portion 71 is larger than the thickness T1 of the proximal end portion 68. The engaging pawl portion 71 is positioned on the front side of the pressing portion 65, and is positioned in a state of having a certain distance from the front surface of the pressing portion 65.

A distal end portion of the engaging pawl portion 71 is formed in a shape that decreases in thickness toward a distal end. The engaging pawl portion 71 includes a sliding surface 71*a* inclined in such a manner as to be displaced rearward as the sliding surface 71*a* approaches the distal end and an engaging surface 71*b* facing rearward.

The second engaging portion 67 is configured as described above. The thickness T1 of the proximal end portion 68 is smaller than the thickness T2 of the folded portion 69, the thickness T3 of the outside portion 70, and the thickness T4 of the engaging pawl portion 71. The proximal end portion 68 is elastically deformable in the thickness direction.

The attachment member 63 is formed in a substantially cylindrical shape whose axial direction is the forward-rearward direction. Operation groove portions 63*a* are formed in the outer circumferential surface of a front half portion of the attachment member 63 in such a manner as to be separated from each other in the circumferential direction (see FIGS. 16 to 18). The operation groove portions 63*a* formed in the attachment member 63 facilitate rotation of the attachment member 63 at the time of gripping and rotational operation of the attachment member 63. An improvement in operability can therefore be achieved.

A screwing portion 63*b* is formed in the inner circumferential surface of a rear half portion of the attachment member 63. The screwing portion 63*b* is screwed onto the spiral groove 64*a* of the tubular portion 64. When the attachment member 63 is rotationally operated, the screwing position of the screwing portion 63*b* with respect to the spiral groove 64*a* is changed to move the attachment member 63 in the forward-rearward direction with respect to the tubular portion 64, and the fastening portions 66 are elastically deformed. The elastic deformation of the fastening portions 66 changes the diameter of the tubular portion 64.

The front half portion of the attachment member 63 is provided as a deformation restricting portion 63*c* that restricts deformation of the first engaging portions 58 in the separator 19 in a state in which the separator 19 is attached to the holding body 18.

<Configuration of Surgical Instrument>

A configuration of a surgical instrument 80 held by the holding body 18 will be described below (see FIGS. 4 to 6).

The surgical instrument 80 is, for example, provided as a scope unit including an endoscope. The surgical instrument 80 includes a shaft portion 81 extending in the forward-rearward direction, a camera head 82 coupled to a rear end portion of the shaft portion 81, and a light guide 83 coupled to an intermediate portion of the shaft portion 81.

An unillustrated plurality of lenses are arranged side by side in an axial direction inside the shaft portion 81. An unillustrated imaging element is disposed inside the camera head 82.

A cable 84 is connected to the camera head 82. Signals are transmitted and received between the imaging element and an unillustrated imaging circuit via the cable 84, and current is supplied to the imaging element via the cable 84.

The light guide 83 includes an annular coupling portion 83*a* coupled to the shaft portion 81, an intermediate portion 83*b* projecting from the coupling portion 83*a* and substantially orthogonal to the shaft portion 81, and a light entry portion 83*c* orthogonal to the intermediate portion 83*b*. The light entry portion 83*c* is positioned above the shaft portion 81 in a state in which the light entry portion 83*c* is substantially parallel with the shaft portion 81.

A light guide cable 85 is connected to the light entry portion 83*c* of the light guide 83. Light is guided from an unillustrated light source to the inside of the shaft portion 81 via the light guide cable 85. Illuminating light L is applied from a distal end portion of the shaft portion 81 (see FIG. 6).

The distal end portion of the shaft portion 81 of the surgical instrument 80 is inserted into the inside of the body cavity 201 from the port 202 formed in the patient 200. In a state in which the distal end portion of the shaft portion 81 is inserted in the body cavity 201, the illuminating light is applied from the distal end portion of the shaft portion 81, and the imaging element images a state inside the body cavity 201. The state inside the body cavity 201 which is imaged by the imaging element is sent out as an imaging signal via the cable 84 to an unillustrated operating device (control device) operated by the operator (surgeon), and the operator can thus remotely observe the state inside the body cavity 201.

<Attachment of Surgical Instrument to Adapter>

Work of attaching the surgical instrument 80 to the adapter 20 will next be described (see FIG. 20 and FIG. 21).

Figure 20:
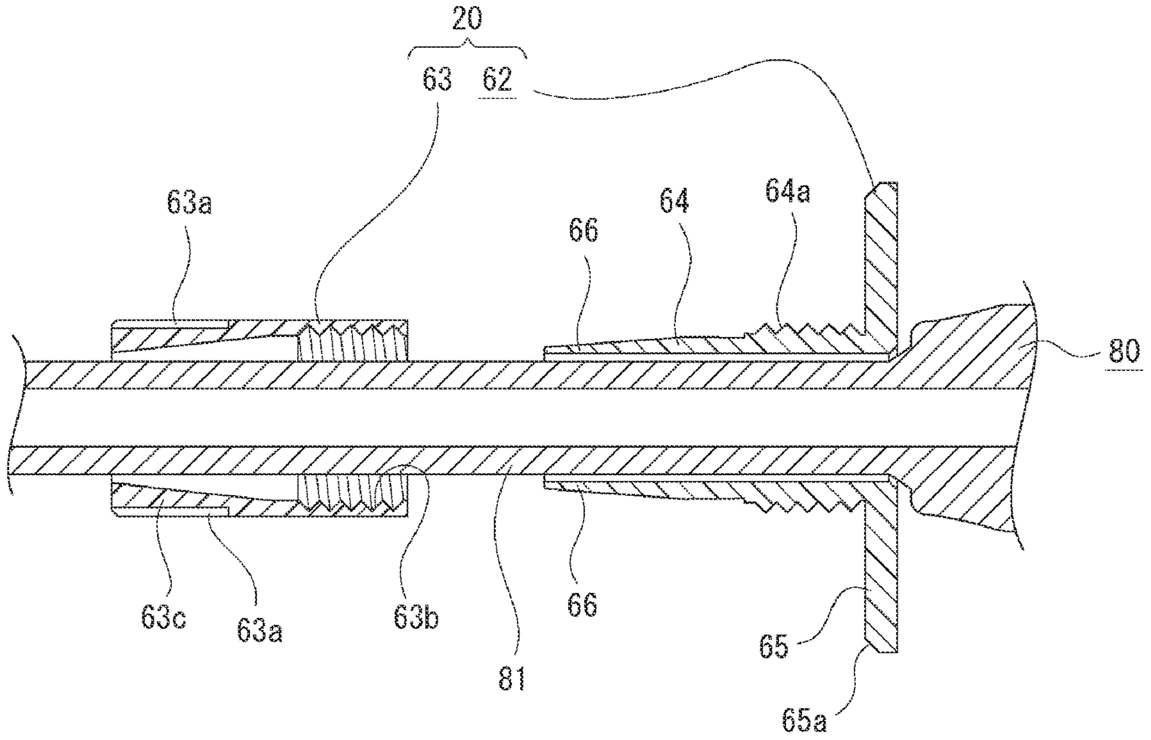
FIG. 20 is a sectional view illustrating a state prior to attachment of the surgical instrument to the adapter
Figure 21:
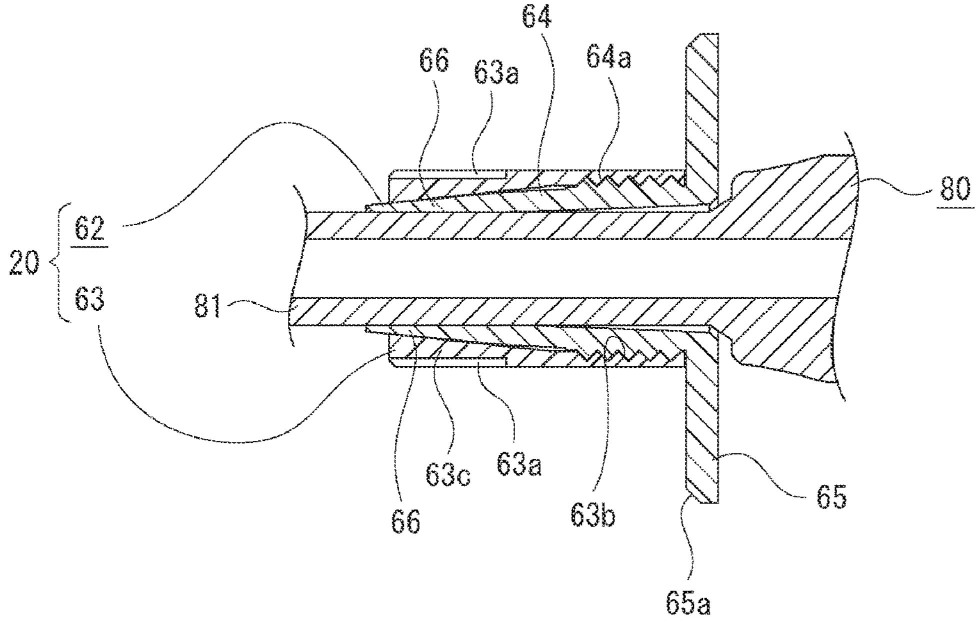
FIG. 21 is a sectional view illustrating a state in which the surgical instrument is attached to the adapter, according to some embodiments.

The shaft portion 81 of the surgical instrument 80 is inserted into the insertion member 62 and the attachment member 63 from the rear in a state in which the attachment member 63 is not attached to the tubular portion 64 of the insertion member 62 (see FIG. 20). At this time, the attachment member 63 is in a state in which the screwing portion 63*b* is not screwed onto the spiral groove 64*a* or a screwing range of the screwing portion 63*b* with respect to the spiral groove 64*a* is small. Hence, the diameter of the tubular portion 64 is enlarged, and the shaft portion 81 can thus be inserted into the tubular portion 64 easily.

In a state in which the shaft portion 81 is inserted in the insertion member 62 and the attachment member 63, the attachment member 63 is manually operated to rotate in a predetermined direction, and hence, the screwing range of the screwing portion 63*b* with respect to the spiral groove 64*a* is increased. The tubular portion 64 is thus fastened by the attachment member 63 (see FIG. 21).

When the attachment member 63 is rotated and the screwing range of the screwing portion 63*b* with respect to the spiral groove 64*a* is thus increased, the diameter of the tubular portion 64 is decreased, so that the shaft portion 81 is fastened by the fastening portions 66, and the surgical instrument 80 is attached to the adapter 20.

Conversely, when the attachment member 63 is rotated in a direction opposite from the foregoing direction and the screwing range of the screwing portion 63*b* with respect to the spiral groove 64*a* is decreased, the diameter of the tubular portion 64 is increased, so that the surgical instrument 80 can be extracted and detached from the adapter 20.

Thus, the attachment of the surgical instrument 80 to the adapter 20 can be performed by rotation of the attachment member 63 in a state in which the shaft portion 81 is inserted in the insertion member 62 and the attachment member 63. The detachment of the surgical instrument 80 from the adapter 20 can be performed by rotation of the attachment member 63 in an opposite direction.

Hence, the attachment and detachment of the surgical instrument 80 to and from the adapter 20 are facilitated, and an improvement in workability can be achieved in the work of attaching and detaching the surgical instrument 80 to and from the adapter 20.

<Attachment of Separator to Holding Body>

Work of attaching the separator 19 to the holding body 18 will next be described (see FIGS. 22 to 25).

Figure 22:
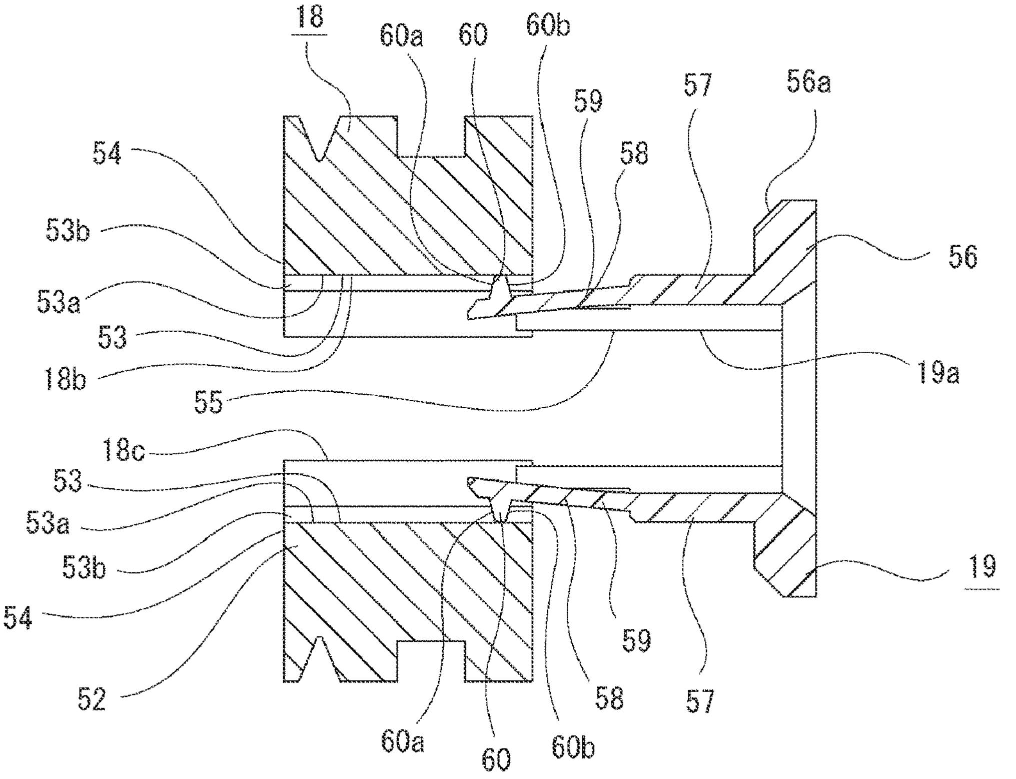
FIG. 22 is a sectional view illustrating a state in which first engaging portions of the separator are inserted in the holding body and the first engaging portions are elastically deformed, according to some embodiments.

The insertion portion 55 of the separator 19 is inserted into the insertion hole 18*b* of the holding body 18 from the rear, and the first engaging portions 58 are respectively inserted into the insertion portions 53 of the holding body 18 from the rear (see FIG. 22). At this time, the separator 19 is inserted into the holding body 18 in an orientation in which the insertion and extraction opening 19*a* is located on the lower side.

When the separator 19 is inserted into the holding body 18 toward the front, the sliding inclined surfaces 60*a* of the protruding portions 60 in the first engaging portions 58 are each slid on end edges of the sliding portions 53*a* in the holding body 18, the deforming portions 59 of the first engaging portions 58 are elastically deformed in directions of approaching each other, and the protruding portions 60 are each slid on the sliding portions 53*a*.

Figure 23:
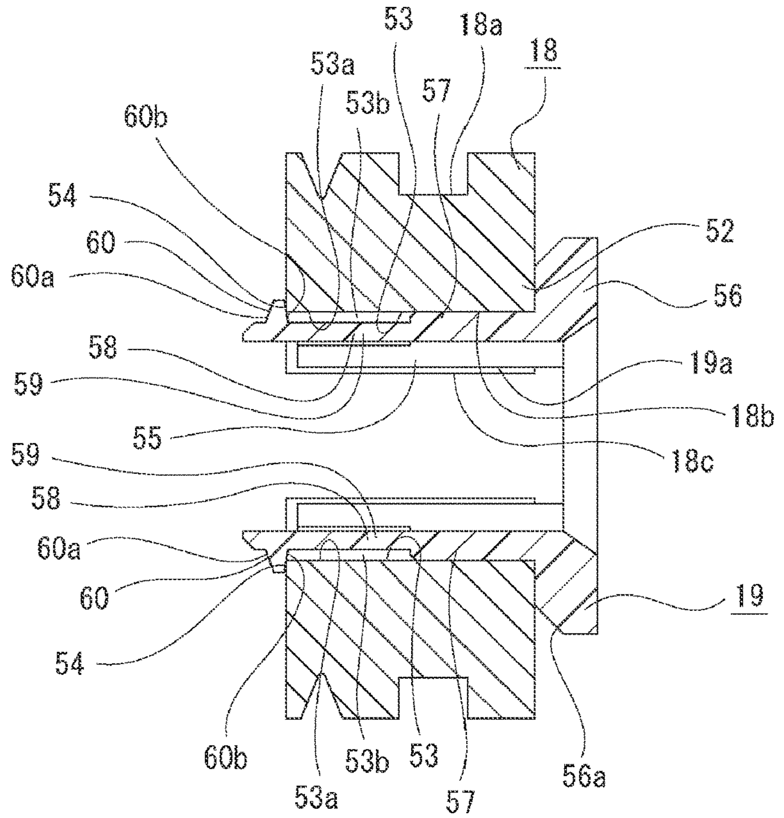
FIG. 23 is a sectional view illustrating a state in which the first engaging portions are elastically restored, the first engaging portions are engaged with first engagement receiving portions, and the separator is thereby attached to the holding body, according to some embodiments.

When the separator 19 is further inserted into the holding body 18 toward the front, the protruding portions 60 of the first engaging portions 58 go over the sliding portions 53*a* (see FIG. 23). When the protruding portions 60 go over the sliding portions 53*a* and project rearward from the holding body 18, the first engaging portions 58 are elastically restored in directions of separating from each other, and the engaging surfaces 60*b* of the protruding portions 60 are each engaged with the first engagement receiving portions 54 of the holding body 18.

In some embodiments, the elastically restored state of the first engaging portions 58 when the engaging surfaces 60*b* are engaged with the first engagement receiving portions 54 not only includes an original state prior to the elastic deformation of the first engaging portions 58 but also includes a state of a reduced degree of deformation with respect to an elastically deformed state in which the sliding inclined surfaces 60*a* of the protruding portions 60 are slid on the sliding portions 53*a* of the holding body 18. Hence, the state of the first engaging portions 58 when the engaging surfaces 60*b* are engaged with the first engagement receiving portions 54 may be a state of a reduced degree of elastic deformation with respect to the elastically deformed state in which the sliding inclined surfaces 60*a* are slid on the sliding portions 53*a*.

When the engaging surfaces 60*b* of the protruding portions 60 are each engaged with the first engagement receiving portions 54 of the holding body 18, the receiving portion 56 of the separator 19 is set in a state of being in contact with the rear surface of the holding body 18, and the separator 19 is attached to the holding body 18 in a state in which the protruding portions 60 and the receiving portion 56 sandwich the holding body 18 in the forward-rearward direction.

Figure 24:
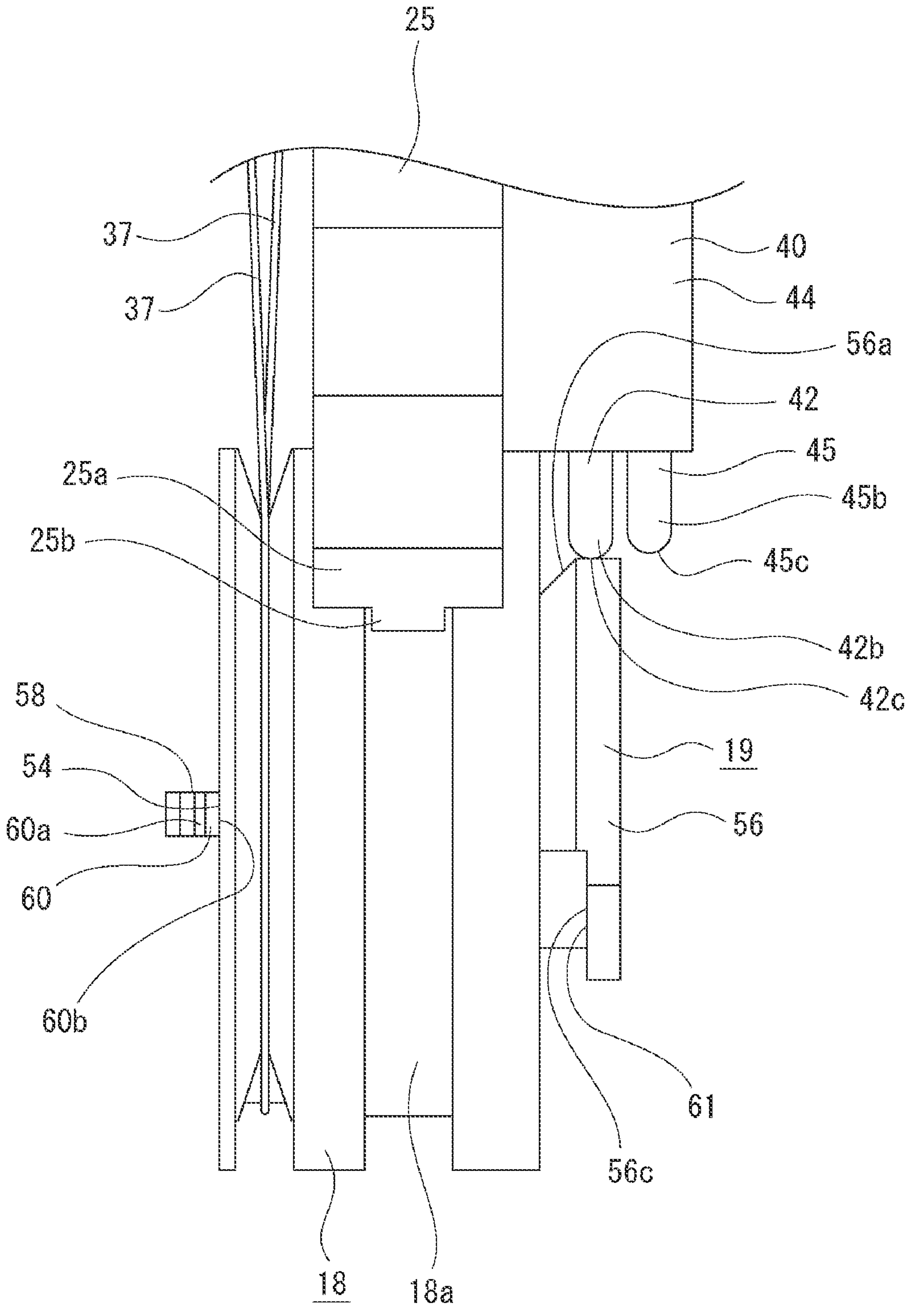
FIG. 24 is a side view illustrating a state in which the attachment of the separator to the holding body is detected by a first detecting unit, according to some embodiments.

When the receiving portion 56 is in contact with the rear surface of the holding body 18, the inclined surface 56*a* formed on the receiving portion 56 is slid on the spherical surface portion 42*c* of the action target portion 42*b* provided to the detecting pin 42 in the first detecting unit 39, and the detecting pin 42 is thus moved upward (see FIG. 24). When the detecting pin 42 is moved upward, the detecting switch 43 is operated and set in an on state by the operating portion 42*a*, and a detection signal is sent out to the detecting circuit. Accordingly, it is detected that the separator 19 is properly attached to the holding body 18.

Figure 25:
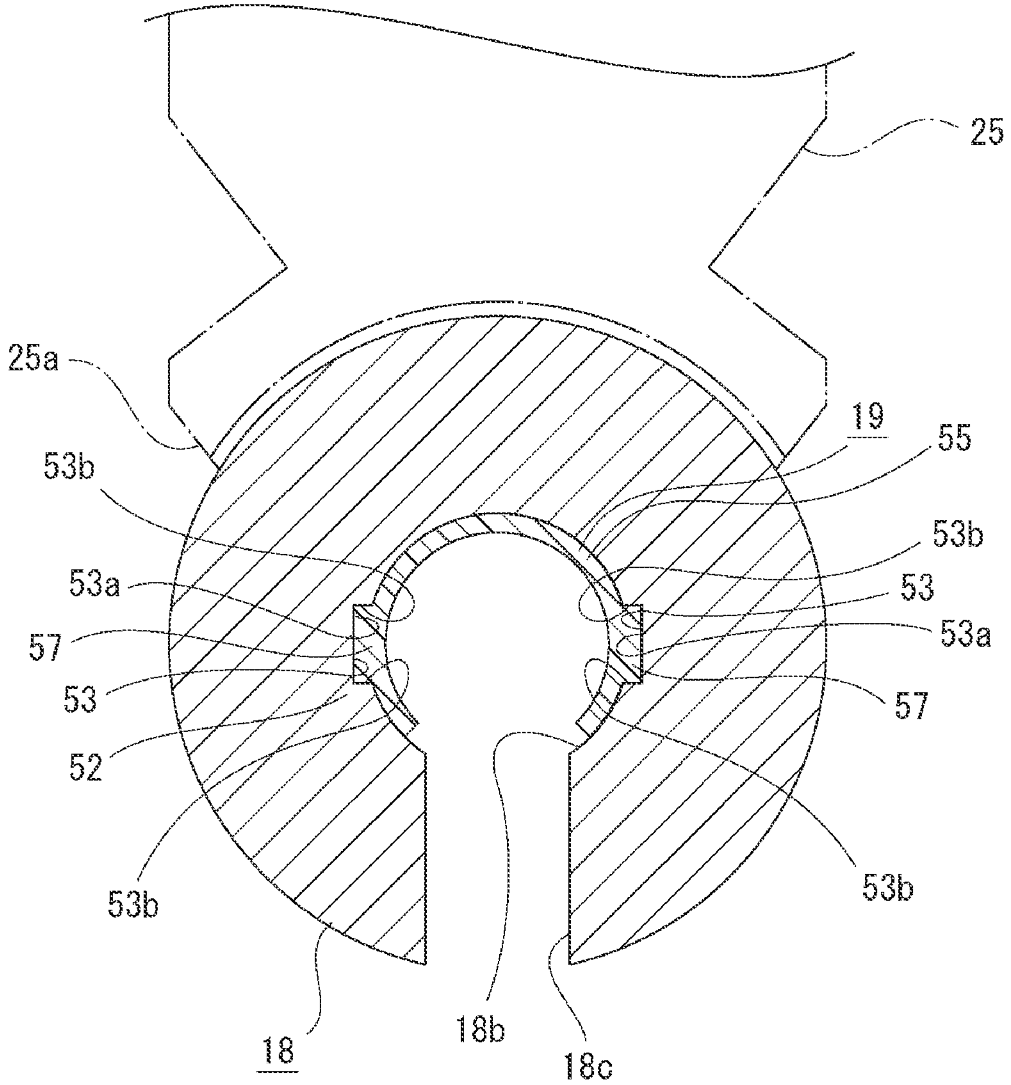
FIG. 25 is a sectional view illustrating a state in which the separator is attached to the holding body, according to some embodiments.

In a state in which the separator 19 is attached to the holding body 18 as described above, the rotation restricted portions 57 of the separator 19 are respectively inserted into the insertion portions 53 of the holding body 18, and the rotation restricted portions 57 are set in a state of being in contact with the rotation restricting portions 53*b* of the insertion portions 53 (see FIG. 23 and FIG. 25). Hence, rotation of the separator 19 with respect to the holding body 18 is restricted by the rotation restricting portions 53*b*.

Detachment of the separator 19 from the holding body 18 can be performed by displacement of the protruding portions 60 projecting rearward from the holding body 18 in directions of approaching each other, elastic deformation of the deforming portions 59 of the first engaging portions 58, and extraction of the separator 19 rearward from the holding body 18.

<Attachment of Adapter to Separator>

Work of attaching the adapter 20 to the separator 19 will next be described (see FIGS. 26 to 33).

Figure 26:
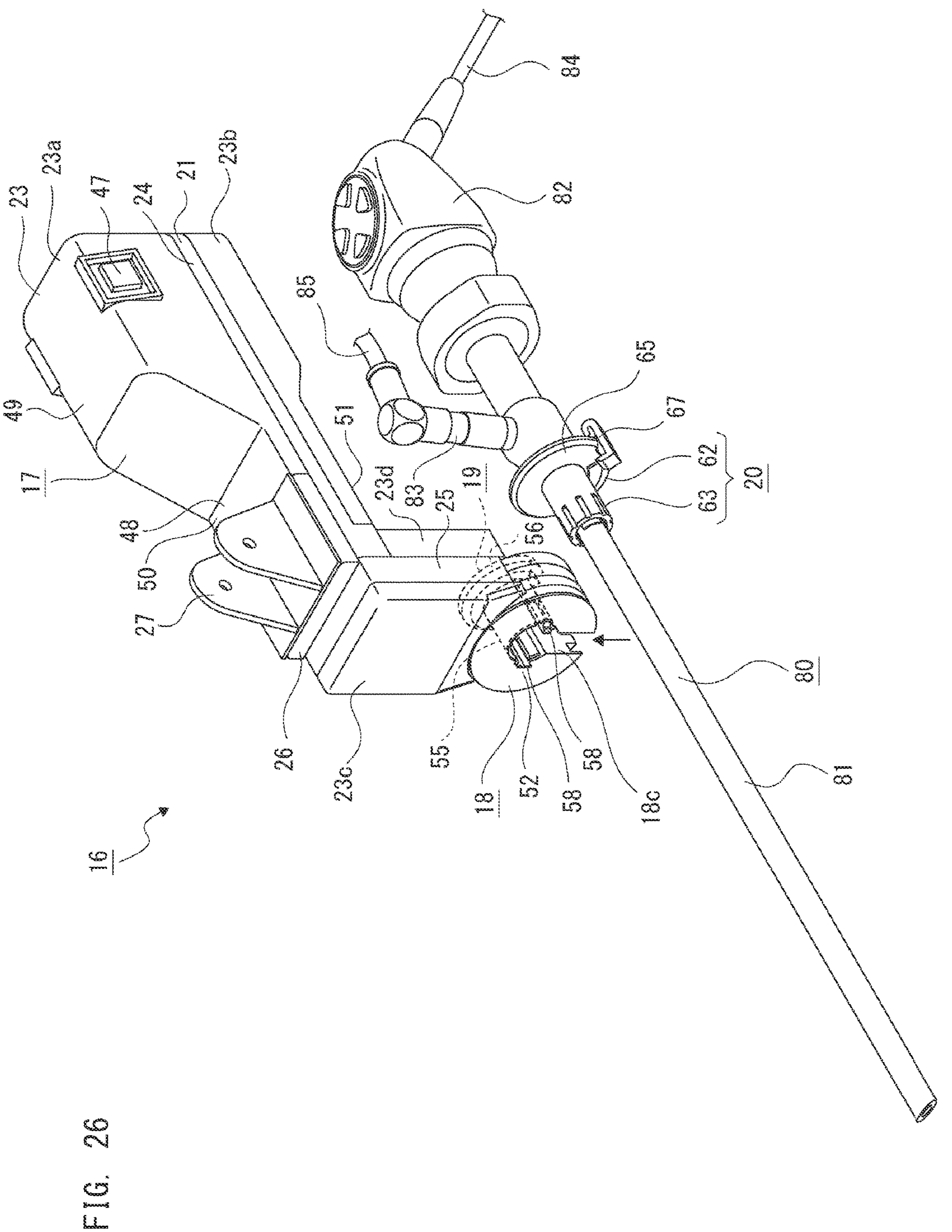
FIG. 26 is a perspective view illustrating a state prior to insertion of the surgical instrument attached to the adapter into the separator in a state in which the separator is attached to the holding body, according to some embodiments.
Figure 27:
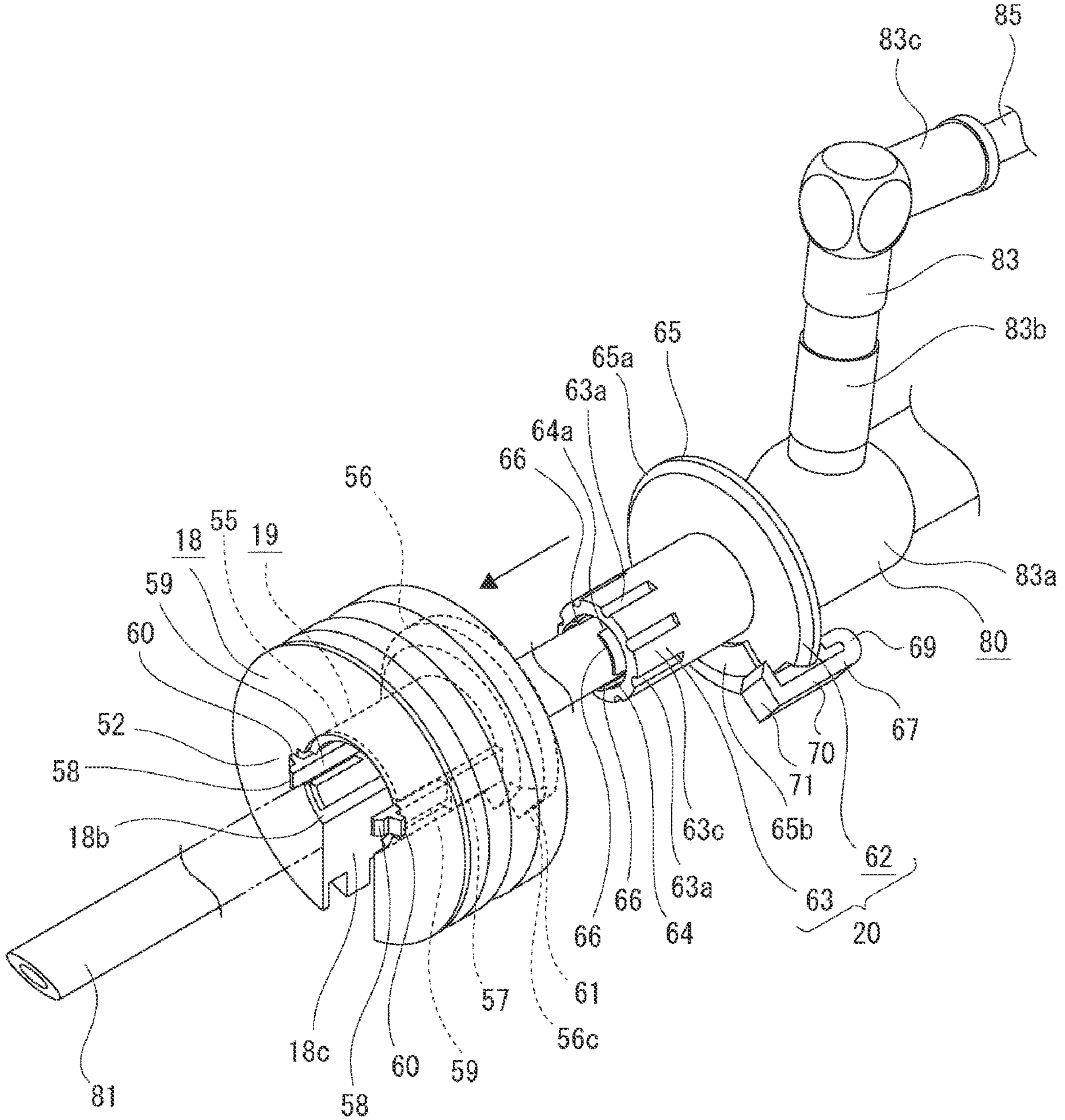
FIG. 27 is a perspective view illustrating a state in which the surgical instrument attached to the adapter is inserted in the separator in the state in which the separator is attached to the holding body, according to some embodiments.

The attachment of the adapter 20 to the separator 19 is performed in a state in which the surgical instrument 80 is attached to the adapter 20 and the separator 19 is attached to the holding body 18 (see FIG. 26). At a time of the attachment of the adapter 20 to the separator 19, first, a part on the front side of a part attached to the adapter 20 in the shaft portion 81 of the surgical instrument 80 is inserted into the inside of the separator 19 from a lower side via the insertion and extraction hole 18*c* of the holding body 18 and the insertion and extraction opening 19*a* of the separator 19 (see FIG. 27).

Figure 28:
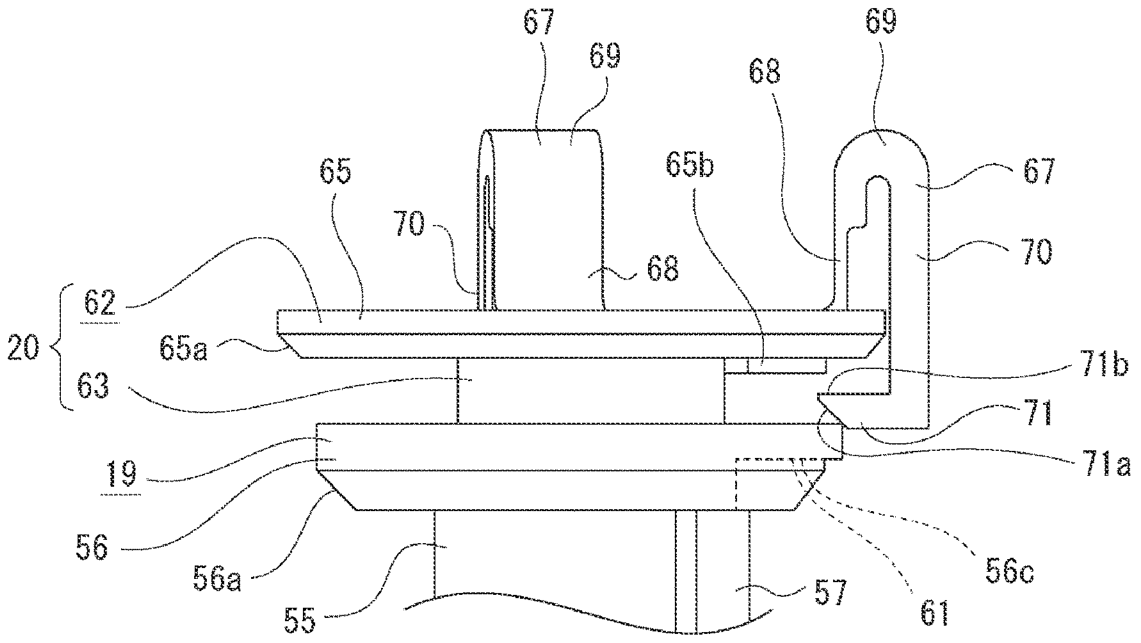
FIG. 28 is a side view illustrating a state in which a tubular portion of the adapter is inserted in an insertion portion of the separator and sliding surfaces of engaging pawl portions are in contact with a receiving portion of the separator, according to some embodiments.

Next, the attachment member 63 and the tubular portion 64 of the adapter 20 are inserted into the insertion portion 55 of the separator 19 from the rear (see FIG. 28). When the attachment member 63 and the tubular portion 64 are inserted into the insertion portion 55 toward the front, the sliding surfaces 71*a* of the engaging pawl portions 71 in the second engaging portions 67 each come into contact with a peripheral edge of the rear surface of the receiving portion 56 of the separator 19.

Figure 29:
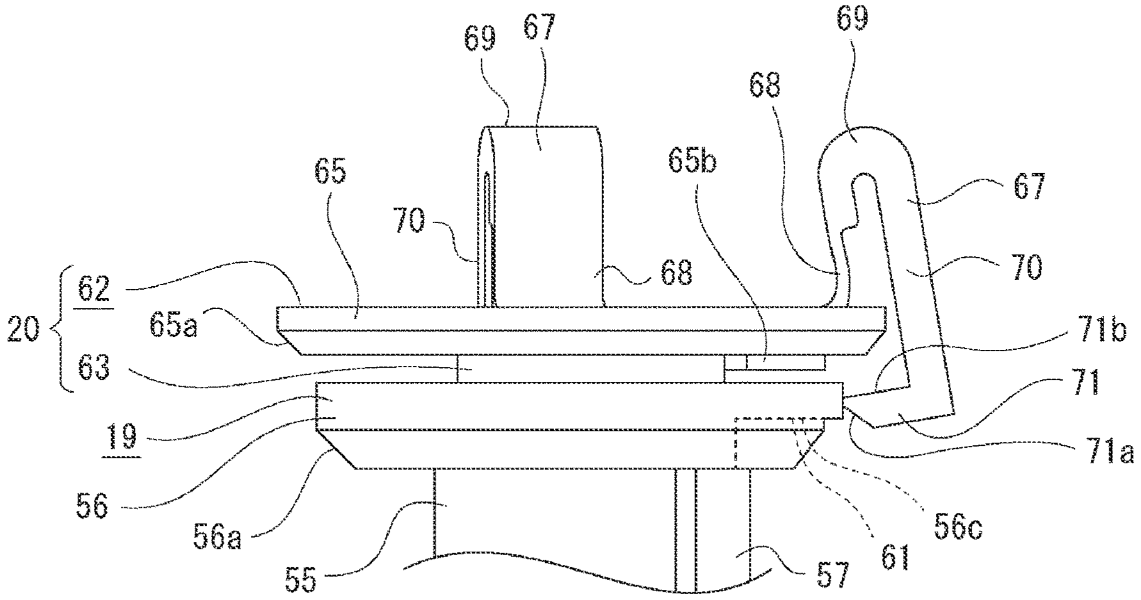
FIG. 29 is a side view illustrating a state in which the tubular portion of the adapter is inserted in the insertion portion of the separator and the second engaging portions are elastically deformed, according to some embodiments.

When the attachment member 63 and the tubular portion 64 continue to be inserted into the insertion portion 55 toward the front, the sliding surfaces 71*a* of the engaging pawl portions 71 are slid on the peripheral edge of the rear surface of the receiving portion 56, the second engaging portions 67 are elastically deformed in directions of separating from each other, and the engaging pawl portions 71 move onto the outer circumferential surface of the receiving portion 56 (see FIG. 29). At this time, mainly the proximal end portions 68 are elastically deformed because the thickness of the proximal end portions 68 of the second engaging portions 67 is smaller than the thickness of the other parts.

Figure 30:
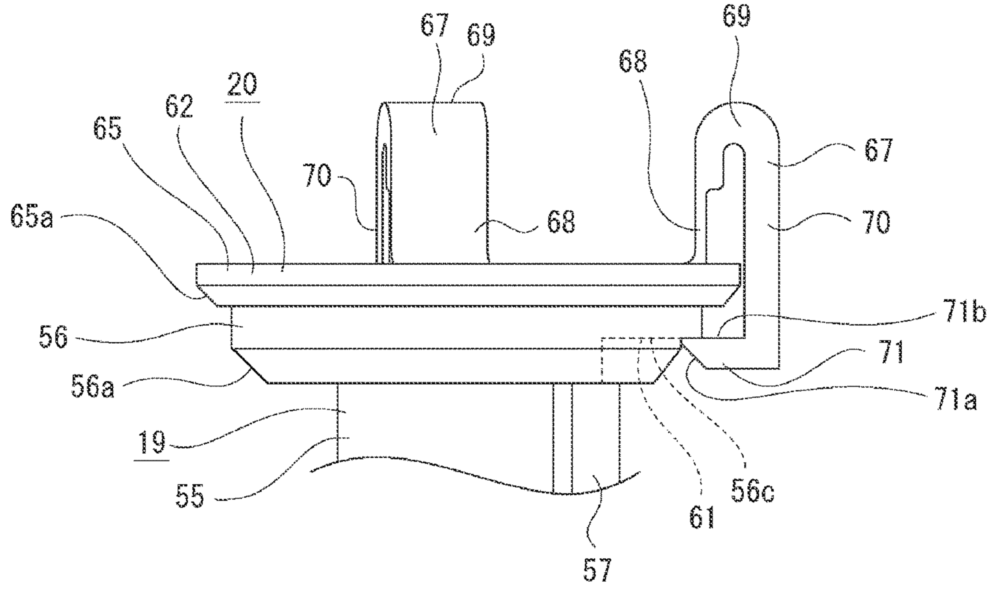
FIG. 30 is a side view illustrating a state in which the second engaging portions are elastically restored, the engaging pawl portions are engaged with second engagement receiving portions, and the adapter is thereby attached to the separator, according to some embodiments.

When the attachment member 63 and the tubular portion 64 are further inserted into the insertion portion 55 toward the front, the sliding surfaces 71*a* of the engaging pawl portions 71 are slid on the outer circumferential surface of the receiving portion 56, and go over the receiving portion 56 (see FIG. 30). When the engaging pawl portions 71 go over the receiving portion 56, the second engaging portions 67 are elastically restored in directions in which the engaging pawl portions 71 approach each other, and the engaging surfaces 71*b* of the engaging pawl portions 71 are each engaged with the second engagement receiving portions 61 of the separator 19 (see FIG. 31).

In some embodiments, the elastically restored state of the second engaging portions 67 when the engaging surfaces 71*b* are engaged with the second engagement receiving portions 61 not only includes an original state prior to the elastic deformation of the second engaging portions 67 but also includes a state of a reduced degree of deformation with respect to an elastically deformed state in which the sliding surfaces 71*a* of the engaging pawl portions 71 are slid on the outer circumferential surface of the receiving portion 56. Hence, the state of the second engaging portions 67 when the engaging surfaces 71*b* are engaged with the second engagement receiving portions 61 may be a state of a reduced degree of elastic deformation with respect to the elastically deformed state in which the sliding surfaces 71*a* are slid on the outer circumferential surface of the receiving portion 56.

When the engaging surfaces 71*b* of the engaging pawl portions 71 are each engaged with the second engagement receiving portions 61 of the separator 19, the pressing portion 65 of the adapter 20 is set in a state of being in contact with the rear surface of the receiving portion 56 in the separator 19, and the adapter 20 is attached to the separator 19 in a state in which the engaging pawl portions 71 and the pressing portion 65 sandwich the separator 19 in the forward-rearward direction.

Figure 32:
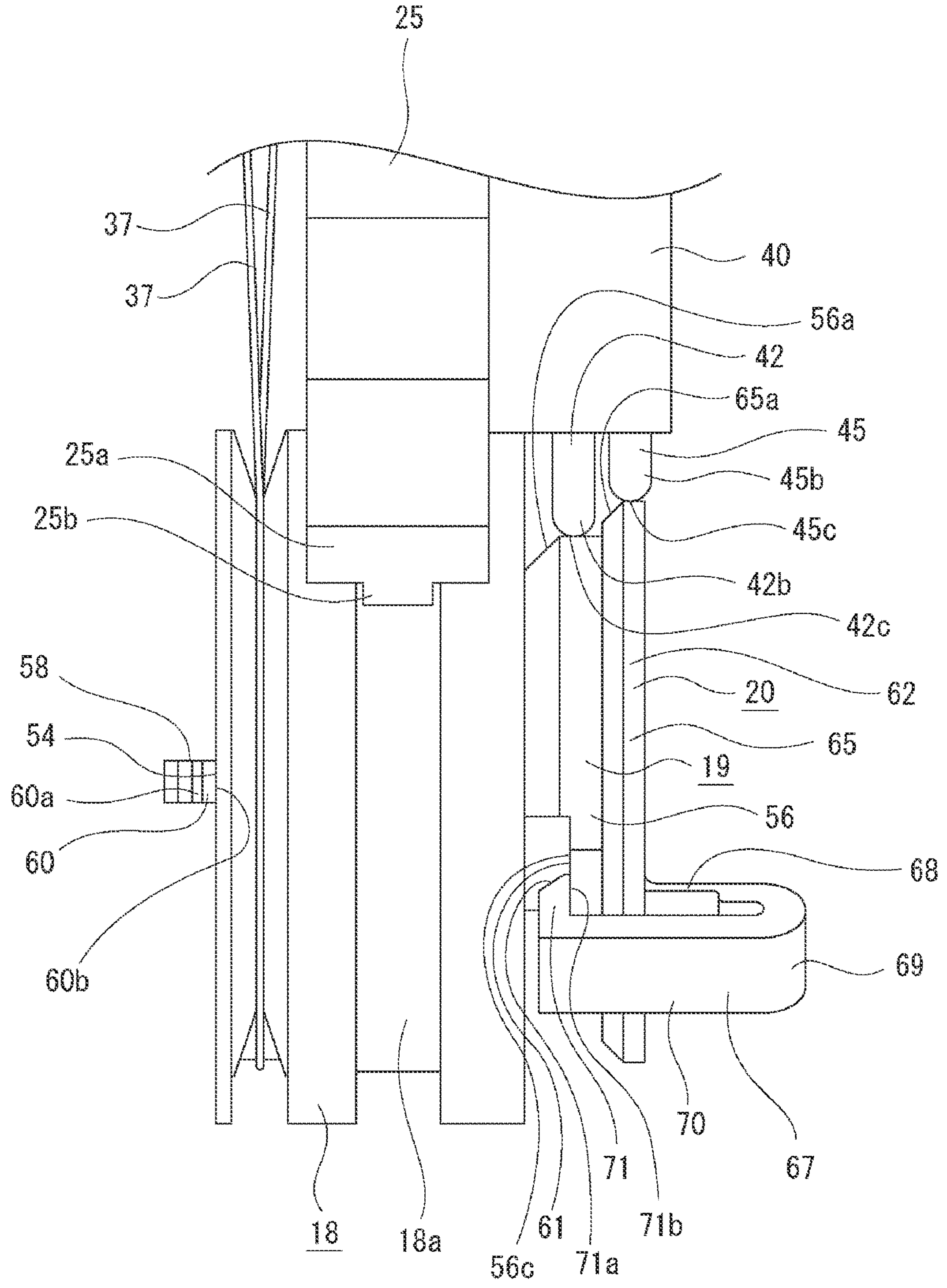
FIG. 32 is a side view illustrating a state in which the attachment of the adapter to the separator is detected by a second detecting unit, according to some embodiments.

When the pressing portion 65 is in contact with the rear surface of the receiving portion 56, the inclined surface 65*a* formed on the pressing portion 65 is slid on the spherical surface portion 45*c* of the action target portion 45*b* provided to the detecting pin 45 in the second detecting unit 40, and the detecting pin 45 is thus moved upward (see FIG. 32). When the detecting pin 45 is moved upward, the detecting switch 46 is operated and set in an on state by the operating portion 45*a*, and a detection signal is sent out to the detecting circuit. Accordingly, it is detected that the adapter 20 is properly attached to the separator 19.

Figure 31:
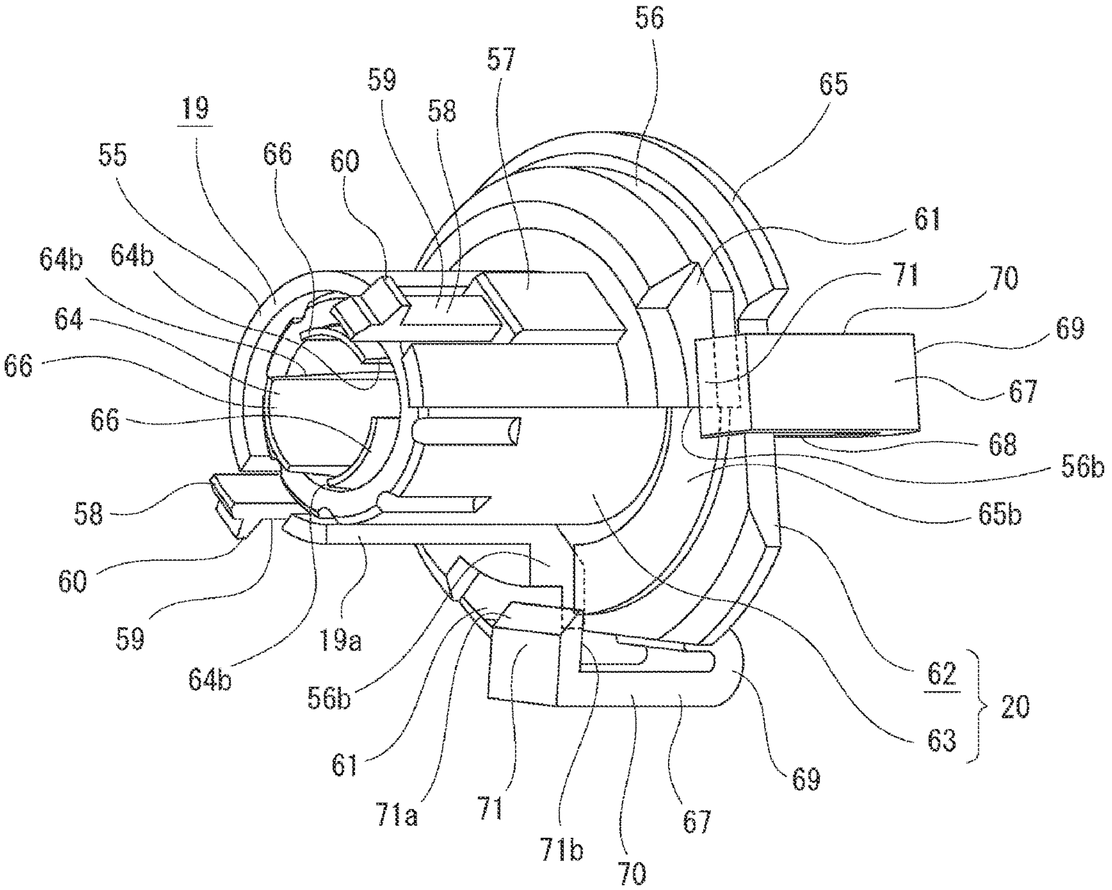
FIG. 31 is a perspective view illustrating a state in which the adapter is attached to the separator, according to some embodiments.

In a state in which the adapter 20 is attached to the separator 19 as described above, the restricted portion 65*b* of the adapter 20 is inserted to a space between the restricting portions 56*b* of the separator 19, and both ends in the circumferential direction of the restricted portion 65*b* are each set in a state of being in contact with the restricting portions 56*b* (see FIG. 31). Hence, rotation of the adapter 20 with respect to the separator 19 is restricted by the restricting portions 56*b*.

Figure 33:
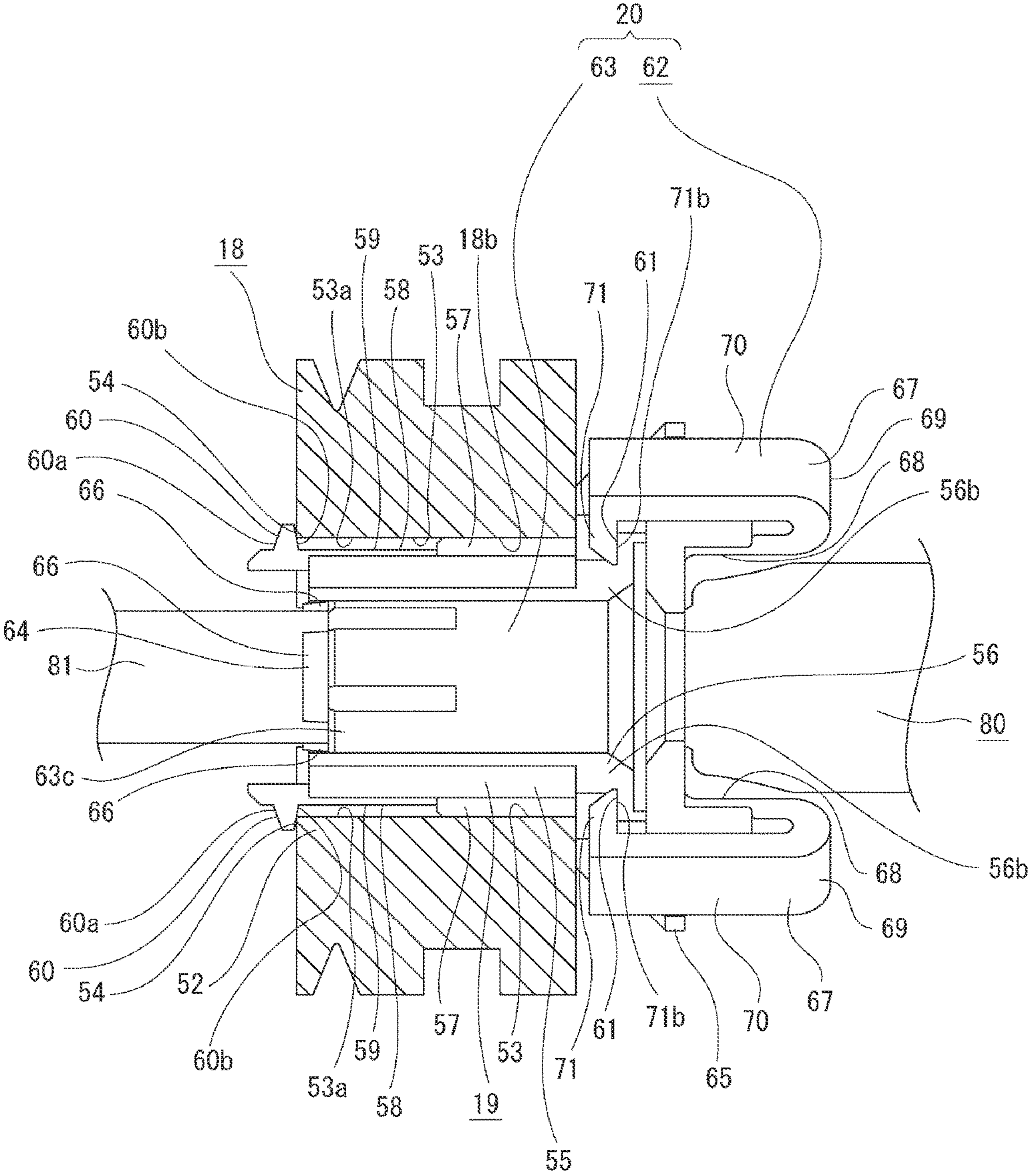
FIG. 33 is a bottom view illustrating, partly in section, a state in which the adapter is attached to the separator and the surgical instrument is held by the holding body via the separator and the adapter, according to some embodiments.

As described above, in a state in which the adapter 20 is attached to the separator 19, the attachment member 63 and the tubular portion 64 of the adapter 20 are inserted into the insertion portion 55 of the separator 19, and the deformation restricting portion 63*c* of the attachment member 63 is positioned in a state of being in contact with or in proximity to the first engaging portions 58 of the separator 19 (see FIG. 33).

Thus, the adapter 20 is provided with the deformation restricting portion 63*c* that restricts deformation of the first engaging portions 58 in a state in which the adapter 20 is attached to the separator 19. In a state in which the separator 19 is attached to the holding body 18, the deformation restricting portion 63*c* restricts deformation of the first engaging portions 58 in a direction in which engagement of the first engaging portions 58 with the first engagement receiving portions 54 is cancelled.

Hence, because the deformation restricting portion 63*c* restricts deformation of the first engaging portions 58 in a state in which the separator 19 is attached to the holding body 18 and the adapter 20 is attached to the separator 19, the separator 19 does not unexpectedly fall off the holding body 18 in a state in which the adapter 20 is attached to the separator 19. A stable state of attachment of the separator 19 to the holding body 18 can thus be ensured by a simple structure.

In addition, the adapter 20 includes the insertion member 62 through which the surgical instrument 80 is inserted and the attachment member 63 that is rotated with respect to the insertion member 62 and that attaches the surgical instrument 80 to the insertion member 62. The attachment member 63 is provided with the deformation restricting portion 63*c*.

Hence, because the attachment member 63 for attaching the surgical instrument 80 to the insertion member 62 is provided with the deformation restricting portion 63*c*, it is not necessary to provide the adapter 20 with another dedicated member having a deformation restricting portion, and it is thus possible to ensure a stable state of attachment of the separator 19 to the holding body 18 without causing an increase in the number of parts.

Detachment of the adapter 20 from the separator 19 can be performed by displacement of the engaging pawl portions 71 in directions of separating from each other, elastic deformation of the second engaging portions 67, and separation of the adapter 20 rearward from the separator 19. In some embodiments, in a state in which the adapter 20 is separated rearward and detached from the separator 19, the surgical instrument 80 can be extracted from the holding body 18 and the separator 19 by pulling out the shaft portion 81 of the surgical instrument 80 downward through the insertion and extraction hole 18*c* of the holding body 18 and the insertion and extraction opening 19*a* of the separator 19.

As described above, the insertion and extraction hole 18*c* and the insertion and extraction opening 19*a* opening in a radial direction are respectively formed in the holding body 18 and the separator 19, and the surgical instrument 80 attached to the adapter 20 is inserted or extracted through the insertion and extraction hole 18*c* and the insertion and extraction opening 19*a*.

Hence, the insertion and extraction of the surgical instrument 80 can be performed in the radial direction of the insertion portion 55. The shaft-shaped shaft portion 81 in the surgical instrument 80 does not need to be moved in an axial direction of the insertion portion 55 to attach or detach the surgical instrument 80 to or from the separator 19 via the adapter 20. The work of attaching and detaching the surgical instrument 80 to and from the separator 19 via the adapter 20 can therefore be performed swiftly.

As described above, in the surgical instrument holding device 16, the adapter 20 is attached to the separator 19 by the pressing portion 65 being pressed against the receiving portion 56 and the second engaging portions 67 being engaged with the receiving portion 56 in a state in which the second engaging portions 67 are elastically restored.

Hence, the pressing portion 65 of the adapter 20 is pressed against the receiving portion 56 of the separator 19, and the second engaging portions 67 that have been elastically deformed are engaged with the receiving portion 56 in an elastically restored state. The receiving portion 56 is held at two different positions by the respective parts of the adapter 20. Thus, the adapter 20 is attached to the separator 19 in a stable state, and displacement of the surgical instrument 80 with respect to the holding body 18 is prevented, so that accuracy and safety of surgery can be reserved.

In some embodiments, the adapter 20 is formed in a shape in which the second engaging portions 67 project from the pressing portion 65. The second engaging portions 67 are provided with the proximal end portion 68 that is continuous with the pressing portion 65 and that extends in a direction of projecting from the pressing portion 65; the folded portion 69 continuous with the proximal end portion 68 and formed in a folded shape; the outside portion 70 continuous with the folded portion 69 and positioned on the peripheral side of the pressing portion 65, at least a part of the outside portion 70 being opposed to the proximal end portion 68; and the engaging pawl portion 71 continuous with the outside portion 70 and bent with respect to the outside portion 70 in a direction of approaching the pressing portion 65. The engaging pawl portion 71 is engaged with the receiving portion 56.

Hence, the adapter 20 is attached to the separator 19 by the pressing portion 65 being pressed against the receiving portion 56 and the second engaging portions 67 being engaged with the receiving portion 56 in a state in which the second engaging portions 67 are elastically restored. The attachment of the adapter 20 to the separator 19 can thus be performed easily.

Further, the receiving portion 56 is provided with the second engagement receiving portions 61, and the engaging pawl portions 71 are engaged with the second engagement receiving portions 61 on an opposite side of the receiving portion 56 from the pressing portion 65.

Hence, because the adapter 20 is attached to the separator 19 by the receiving portion 56 being sandwiched from opposite sides by the pressing portion 65 and the engaging pawl portions 71, a stable state of attachment of the adapter 20 to the separator 19 can be ensured.

In the surgical instrument holding device 16, as described above, the driving body 17 is provided with the driving force transmitting mechanism 22 that transmits a driving force to the holding body 18 and the bracket 21 by which the driving force transmitting mechanism 22 is supported, and the detecting mechanism 38 is disposed on the bracket 21.

Hence, because the detecting mechanism 38 is disposed on the bracket 21 of the driving body 17 that supports the holding body 18 in a rotatable manner, the detecting mechanism 38 does not rotate in association with the holding body 18, and the detecting mechanism 38 is disposed on the non-operating part that is not operated in association with the holding body 18. It is therefore possible to achieve an improvement in accuracy of detection of the positions of the separator 19 and the adapter 20 by the detecting mechanism 38.

In some embodiments, because the detecting mechanism 38 is disposed on the non-operating part that is not operated in association with the holding body 18, a load is not easily generated on a cable that connects the detecting apparatus 38 to the detecting circuit and a power supply circuit, and degradation of the cable can thus be suppressed.

Further, in the surgical instrument holding device 16, at a time of attachment of the separator 19 to the holding body 18 and at a time of attachment of the adapter 20 to the separator 19, detection is performed by the detecting mechanism 38. The detecting mechanism 38 is provided with the main body sections 41 and 44 attached to the bracket 21 and the detecting pins 42 and 45 moved with respect to the main body sections 41 and 44. The detection is performed according to movement of the detecting pins 42 and 45 by the action of the separator 19 and the adapter 20 on the detecting pins 42 and 45.

Hence, a state of attachment of the separator 19 to the holding body 18 is detected with the detecting pin 42 or 45 moved by the action of the separator 19, and a state of attachment of the adapter 20 to the separator 19 is detected with the detecting pin 42 or 45 moved by the action of the adapter 20. The respective detection for the separator 19 and the adapter 20 can thus be performed in an easy and reliable manner.

Further, the separator 19 is attached to the holding body 18 in a state in which the insertion portion 55 is inserted into the holding body 18. The adapter 20 is attached to the separator 19 in a state in which the separator 19 is attached to the holding body 18 and the tubular portion 64 is inserted into the insertion portion 55. The state of attachment of the separator 19 to the holding body 18 is detected according to the action of the receiving portion 56 on the detecting pin 42 or 45 at a time of insertion of the insertion portion 55 into the holding body 18. The state of attachment of the adapter 20 to the separator 19 is detected according to the action of the pressing portion 65 on the detecting pin 42 or 45 at a time of insertion of the tubular portion 64 into the insertion portion 55.

Hence, the state of attachment of the separator 19 to the holding body 18 is detected according to the action of the receiving portion 56 projecting outward from the outer circumferential edge of the insertion portion 55 on the detecting pin 42 or 45. The state of attachment of the adapter 20 to the separator 19 is detected according to the action of the pressing portion 65 projecting outward from the outer circumferential edge of the tubular portion 64 on the detecting pin 42 or 45. It is thus possible to shorten the length of the detecting pins 42 and 45, and thereby achieve downsizing of the detecting mechanism 38.

In some embodiments, the inclined surface 56*a* that approaches the insertion portion 55 in a direction of insertion of the insertion portion 55 into the holding body 18 is formed on the outer circumferential portion of the receiving portion 56. The inclined surface 65*a* that approaches the tubular portion 64 in a direction of insertion of the tubular portion 64 into the insertion portion 55 is formed on the outer circumferential portion of the pressing portion 65. The detecting pins 42 and 45 are moved with respect to the main body sections 41 and 44 by the inclined surfaces 56*a* and 65*a* respectively being slid on distal end portions of the detecting pins 42 and 45.

Hence, the inclined surface 56*a* of the receiving portion 56 is slid on the detecting pin 42 at a time of attachment of the separator 19 to the holding body 18, and the inclined surface 65*a* of the pressing portion 65 is slid on the detecting pin 45 at a time of attachment of the adapter 20 to the separator 19. It is thereby possible to smoothly perform the attachment of the separator 19 to the holding body 18 and the attachment of the adapter 20 to the separator 19, and ensure a proper operation state of the detecting mechanism 38 by movement of the detecting pins 42 and 45 without fail.

In some embodiments, the distal end surfaces of the detecting pins 42 and 45 are formed as the spherical surface portions 42*c* and 45*c* protruding to the distal end sides. Thus, the receiving portion 56 is slid on the spherical surface portion 42*c* at the time of attachment of the separator 19 to the holding body 18, and the pressing portion 65 is slid on the spherical surface portion 45*c* at the time of attachment of the adapter 20 to the separator 19.

Hence, it is possible to smoothly perform the attachment of the separator 19 to the holding body 18 and the attachment of the adapter 20 to the separator 19, and ensure a proper operation state of the detecting mechanism 38 by movement of the detecting pins 42 and 45 without fail.

<State of Holding of Surgical Instrument by Holding Body>

As described above, the surgical instrument 80 is held by the holding body 18 via the separator 19 and the adapter 20 by the adapter 20 being attached to the separator 19 in a state in which the separator 19 is attached to the holding body 18 and the surgical instrument 80 is attached to the adapter 20.

In a state in which the adapter 20 is attached to the separator 19 as described above, the first engaging portions 58 of the separator 19 and the second engaging portions 67 of the adapter 20 are positioned on opposite sides of the holding body 18 in the axial direction (forward-rearward direction) of the tubular portion 64 (see FIG. 32 and FIG. 33).

Hence, because the first engaging portions 58 and the second engaging portions 67 are positioned in a manner separated from each other in the axial direction of the tubular portion 64, it is difficult for a finger to accidentally come into contact with the first engaging portions 58 when the work of detaching the adapter 20 from the separator 19 is performed by elastic deformation of the second engaging portions 67. The separator 19 can thereby be prevented from unexpectedly falling off the holding body 18.

In particular, the separator 19 is a member to which a part of the drape is attached, and the drape may be damaged by contact of the drape with the surgery assisting device 1 or the like when the separator 19 unexpectedly falls off the holding body 18. Thus, preventing the separator 19 from unexpectedly falling off the holding body 18 can also prevent damage to the drape.

Figure 34:
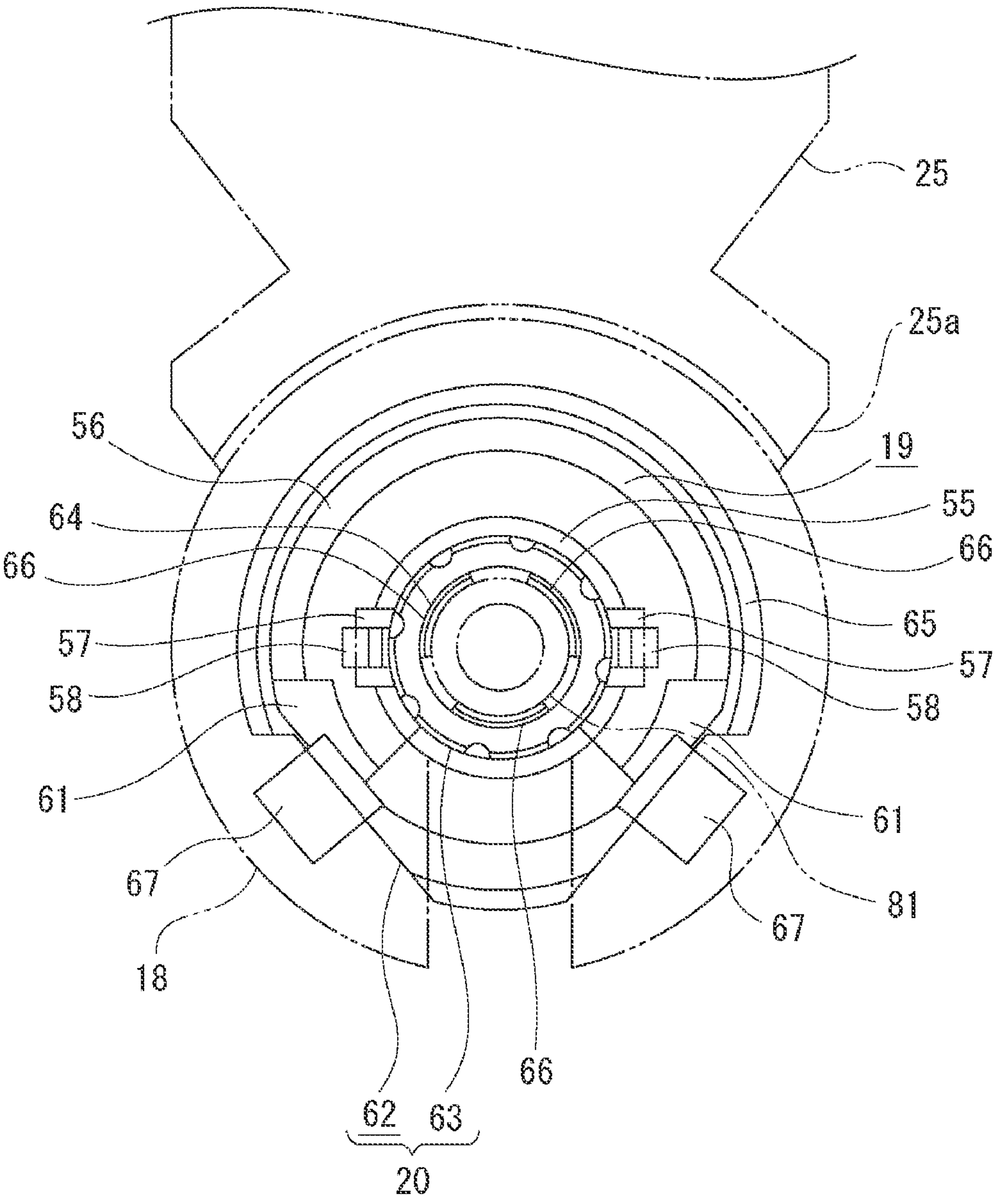
FIG. 34 is a rear view illustrating the state in which the adapter is attached to the separator and the surgical instrument is held by the holding body via the separator and the adapter, according to some embodiments.

In some embodiments, in a state in which the adapter 20 is attached to the separator 19, the first engaging portions 58 of the separator 19 and the second engaging portions 67 of the adapter 20 are located at different positions in the circumferential direction of the tubular portion 64 (see FIG. 34).

Hence, because the first engaging portions 58 and the second engaging portions 67 are positioned in a manner separated from each other in the circumferential direction of the tubular portion 64, it is difficult for a finger to accidentally come into contact with the first engaging portions 58 when the work of detaching the adapter 20 from the separator 19 is performed by elastic deformation of the second engaging portions 67. The separator 19 can thereby be prevented from unexpectedly falling off the holding body 18.

Figure 35:
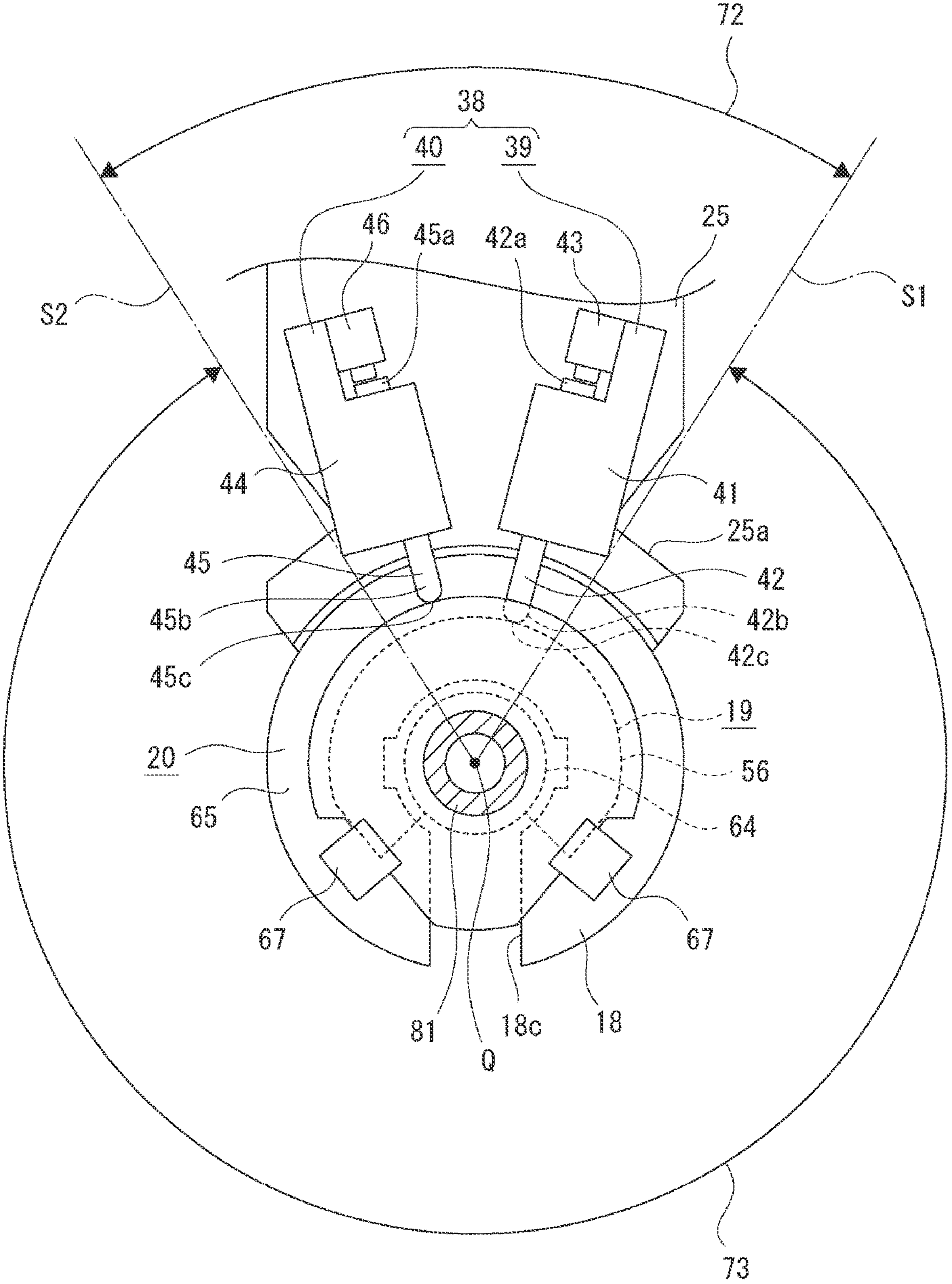
FIG. 35 is a rear view illustrating a positional relation between the detecting mechanism and the second engaging portions of the adapter, according to some embodiments.

Further, suppose that, in a state in which the adapter 20 is attached to the separator 19, two planes passing respective ends of the detecting mechanism 38 in the circumferential direction of the tubular portion 64 and a center Q of the tubular portion 64 are a plane S1 and a plane S2 (see FIG. 35). At this time, supposing that, of regions divided by the plane S1 and the plane S2, a region in which the detecting mechanism 38 is present is a first region 72 and another region is a second region 73, the second engaging portions 67 are positioned in the second region 73.

Hence, the plurality of second engaging portions 67 are respectively engaged with the second engagement receiving portions 61 and the detecting mechanism 38 and the plurality of second engaging portions 67 are positioned in the different regions It is thus possible to ensure a proper operation state of the detecting mechanism 38 by ensuring a stable state of attachment of the adapter 20 to the separator 19 and preventing interference between the second engaging portions 67 and the detecting mechanism 38.

In some embodiments, a most stable state of attachment of the adapter 20 to the separator 19 can be ensured with the second engaging portions 67 projecting 180 degrees opposite each other in the circumferential direction of the pressing portion 65 in the adapter 20.

However, in a case where the second engaging portions 67 project 180 degrees opposite each other in the circumferential direction of the pressing portion 65, distances between the second engaging portions 67 and the detecting mechanism 38 are reduced, and a finger may accidentally come into contact with the detecting mechanism 38 when the adapter 20 is attached to the separator 19. Hence, in order to prevent such contact of a finger with the detecting mechanism 38, the second engaging portions 67 are preferably positioned below a horizontal plane passing through the center Q of the tubular portion 64.

In some embodiments, in the surgical instrument holding device 16, the separator 19 is attached to the holding body 18 by engagement of the first engaging portions 58 with the first engagement receiving portions 54 in a state in which the first engaging portions 58 are elastically restored, and the adapter 20 is attached to the separator 19 by engagement of the second engaging portions 67 with the second engagement receiving portions 61 in a state in which the second engaging portions 67 are elastically restored.

Hence, the surgical instrument 80 is held by the holding body 18 via the separator 19 and the adapter 20 by engagement of the first engaging portions 58 that have been elastically deformed with the first engagement receiving portions 54 in a state in which the first engaging portions 58 are elastically restored, and engagement of the second engaging portions 67 that have been elastically deformed with the second engagement receiving portions 61 in a state in which the second engaging portions 67 are elastically restored. The attachment and detachment of the surgical instrument 80 to and from the holding body 18 can thus be performed in an easy and prompt manner.

Further, the adapter 20 is provided with the tubular portion 64 through which the surgical instrument 80 penetrates, and the separator 19 is provided with the insertion portion 55 into which the tubular portion 64 is inserted. In a state in which the tubular portion 64 is inserted in the insertion portion 55, the separator 19 is attached to the holding body 18, and the adapter 20 is attached to the separator 19.

Hence, because the separator 19 is attached to the holding body 18 in a state in which the tubular portion 64 through which the surgical instrument 80 has penetrated is inserted in the insertion portion 55, the separator 19 and the adapter 20 are arranged in a small space with respect to the holding body 18, and downsizing of the surgical instrument holding device 16 can thereby be achieved.

<Operation of Surgery Assisting Device>

Operation of the surgery assisting device 1 will next be described (see FIGS. 36 to 42).

In the surgery assisting device 1 configured as described above, when a surgical operation is performed, the first movable body 7, the second movable body 8, the third movable body 12, the fourth movable body 15, the driving body 17 functioning as the fifth movable body, and the holding body 18 functioning as the sixth movable body are rotationally (revolvingly) operated in such a manner as to change the position and pose of the surgical instrument 80 held by the holding body 18 to a desired state.

At this time, when the first movable body 7 is rotated, the second movable body 8, the third movable body 12, the fourth movable body 15, the driving body 17, and the holding body 18 are operated to change the position or pose of the surgical instrument 80 in association with the rotational operation of the first movable body 7. When the second movable body 8 is rotated, the third movable body 12, the fourth movable body 15, the driving body 17, and the holding body 18 are operated to change the position or pose of the surgical instrument 80 in association with the rotational operation of the second movable body 8. In some embodiments, when the third movable body 12 is rotated, the fourth movable body 15, the driving body 17, and the holding body 18 are operated to change the position or pose of the surgical instrument 80 in association with the rotational operation of the third movable body 12. When the fourth movable body 15 is rotated, the driving body 17 and the holding body 18 are operated to change the position or pose of the surgical instrument 80 in association with the rotational operation of the fourth movable body 15. Further, when the driving body 17 is rotated, the holding body 18 is operated to change the position or pose of the surgical instrument 80 in association with the rotational operation of the driving body 17. When the holding body 18 is rotated, the surgical instrument 80 is rotated in association with the rotational operation of the holding body 18.

The surgical operation is, for example, performed by an operator (surgeon) who remotely operates the surgery assisting device 1 installed in the operating room according to a master-slave system. The master-slave system is a system in which when a plurality of apparatuses are operated in cooperation with each other, roles are divided for a master machine in charge of control and operation of the plurality of apparatuses and a slave machine operated under the control of the master machine. In this surgical operation, an unillustrated operating device (control device) which is operated by the operator is the master machine, and the surgery assisting device 1 is the slave machine.

When the surgery assisting device 1 is to be used in the surgical operation, first, the position in the upward-downward direction of the main unit 4 is set by moving the first connecting arm 5 in the upward-downward direction with respect to the pole 3 according to the position of the patient 200. Next, the position of the surgical instrument 80 is set by rotating the first connecting arm 5 with respect to the pole 3 and rotating the second connecting arm 6 with respect to the first connecting arm 5 according to a surgical operation position.

Figure 36:
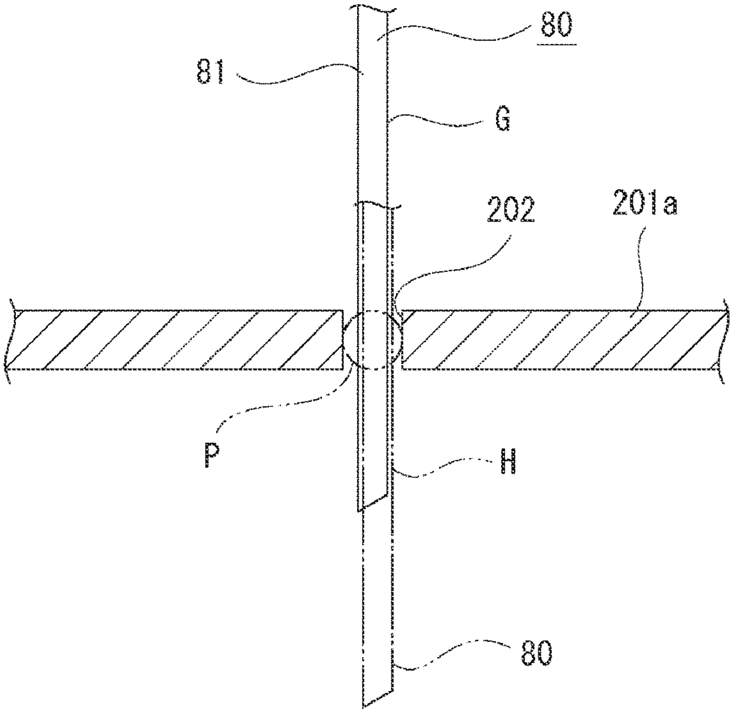
FIG. 36 is a conceptual diagram illustrating a state in which the surgical instrument inserted in a port is moved with respect to a body cavity, according to some embodiments.
Figure 37:
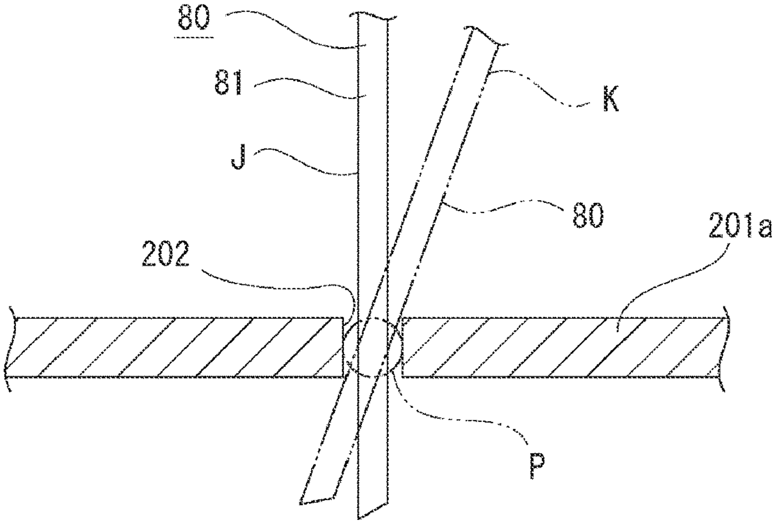
FIG. 37 is a conceptual diagram illustrating a state in which the surgical instrument inserted in the port is inclined with respect to the body cavity, according to some embodiments.

When the surgical operation is performed, a pivot point P is set to serve as a reference point for movement of the surgical instrument 80 (see FIG. 36 and FIG. 37).

The pivot point P is a position substantially coinciding with the port 202 through which the surgical instrument 80 is inserted. In a case where a trocar 90 is used, the pivot point P substantially coincides with the position of the trocar 90 (see FIG. 2). Hence, when the position is controlled and appropriate pivot operation is performed such that a part of the surgical instrument 80 always passes through the pivot point P in a state in which the surgical instrument 80 is inserted in the body cavity 201 of the patient 200, the generation of a load on a tissue in the vicinity of the body surface of the patient 200 is prevented and thus safety is reserved even when the position of the surgical instrument 80 is changed (position H in FIG. 36) with respect to an original position (position G in FIG. 36).

Incidentally, in FIG. 36, for the surgical instrument 80 moved in the axial direction of the shaft portion 81, in order to facilitate understanding, the surgical instrument 80 prior to the movement and the surgical instrument 80 after the movement are intentionally shifted from each other slightly in a direction orthogonal to the axial direction, and are illustrated such that a solid line representing the surgical instrument 80 at the position G and a broken line representing the surgical instrument 80 at the position H do not coincide with each other.

In some embodiments, when the pose of the surgical instrument 80 is controlled and appropriate pivot operation is performed such that a part of the surgical instrument 80 always passes through the pivot point P in a state in which the surgical instrument 80 is inserted in the body cavity 201 of the patient 200, the generation of a load on a tissue in the vicinity of the body surface of the patient 200 is prevented and safety is thus reserved even when the pose of the surgical instrument 80 is changed (pose K in FIG. 37) with respect to an original pose (pose J in FIG. 37).

Meanwhile, in the surgical operation, there are an operator, assistants, and many appliances for surgery in the operating room. Hence, particularly in a case where the area of the operating room is limited, a person, an appliance, or the like present in the operating room may unexpectedly come into contact with parts of the surgery assisting device 1.

For example, during the surgery, a preparatory state for the surgery, or the like, when a person, an appliance, or the like present in the operating room unexpectedly comes into contact with the separator 19 and a force of the contact is applied as an external force, the applied external force may destabilize the state of attachment of the adapter 20 to the separator 19. Meanwhile, in order to achieve an improvement in workability of the attachment work, the attachment of the adapter 20 to the separator 19 is preferably performed in an easy manner.

Figure 38:
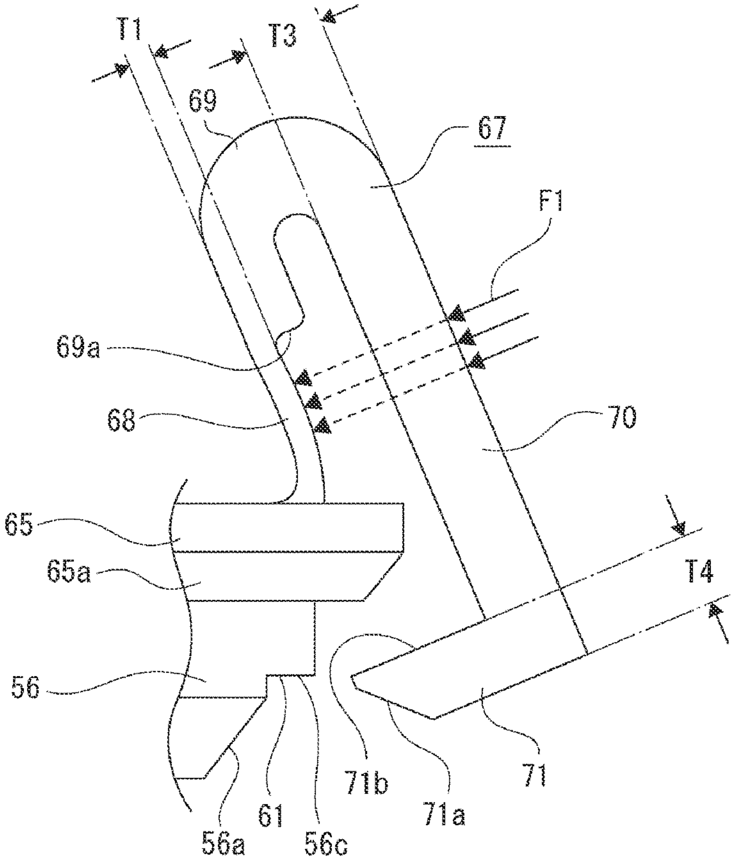
FIG. 38 is a conceptual diagram illustrating a state in which an external force is applied to a proximal end portion of the second engaging portion via an outside portion, according to some embodiments.
Figure 39:
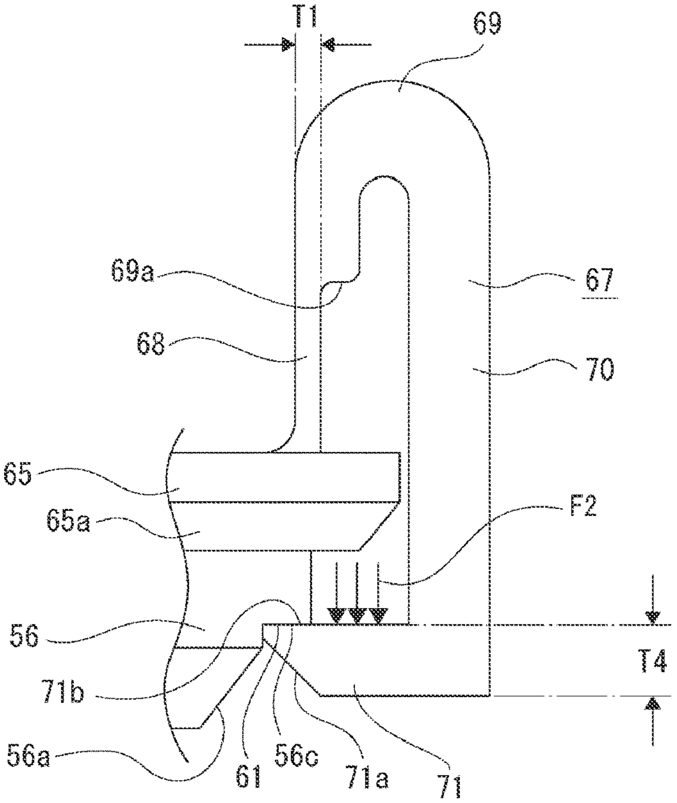
FIG. 39 is a conceptual diagram illustrating a state in which an external force is applied to the engaging pawl portion of the second engaging portion, according to some embodiments.

Accordingly, in order to prevent the occurrence of the problem due to the application of such an external force and ensure ease of attachment, the thickness T1 of the proximal end portion 68 in the second engaging portion 67 of the adapter 20 is smaller than the thickness T4 of the engaging pawl portion 71 (see FIG. 38 and FIG. 39).

Hence, the proximal end portion 68 bends easily when a force F1 (see FIG. 38) is applied to the proximal end portion 68 in the thickness direction via the outside portion 70, while the engaging pawl portion 71 does not bend easily when a force F2 (see FIG. 39) is applied to the engaging pawl portion 71 in the thickness direction. Thus, when the force F1 is applied to the proximal end portion 68, the engagement of the engaging pawl portion 71 with the receiving portion 56 is cancelled easily, and thus, the adapter 20 can be detached from the separator 19 easily, but when the force F2 is applied to the engaging pawl portion 71, the engagement of the engaging pawl portion 71 with the receiving portion 56 is not cancelled easily, and thus, the detachment of the adapter 20 from the separator 19 can be prevented.

Figure 40:
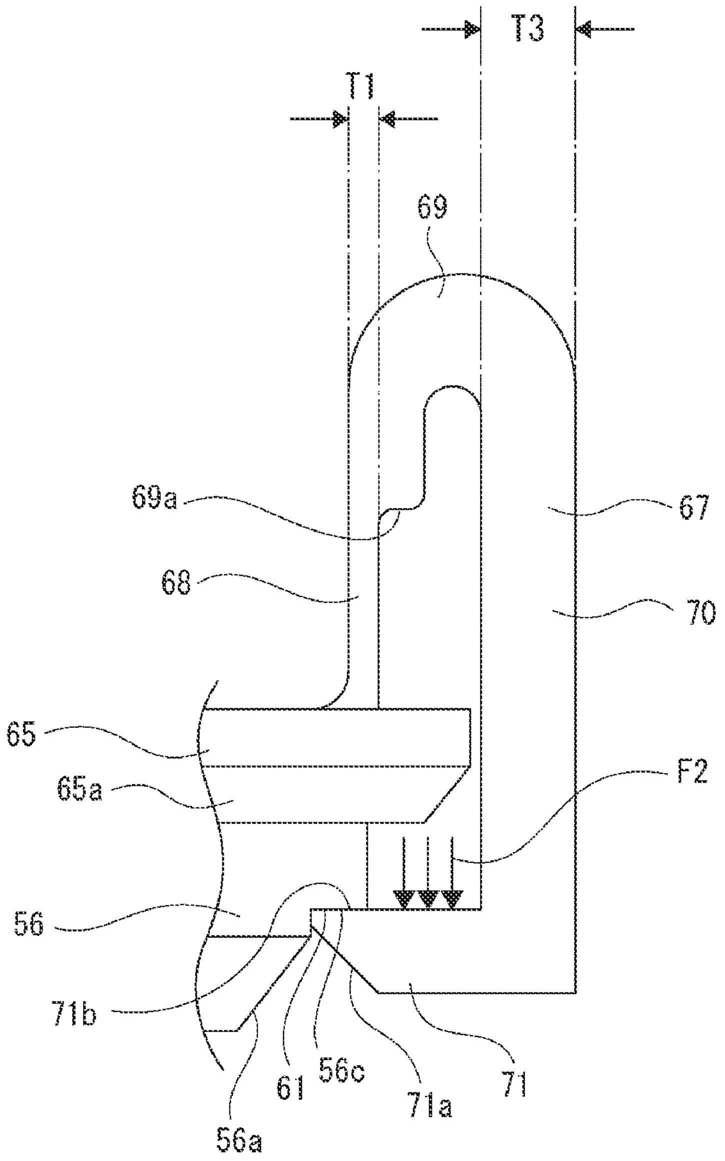
FIG. 40 is a conceptual diagram illustrating a state in which an external force is applied to a part of the outside portion in the second engaging portion which part is close to the engaging pawl portion, according to some embodiments.

In some embodiments, the thickness T3 of the outside portion 70 in the second engaging portion 67 of the adapter 20 is larger than the thickness T1 of the proximal end portion 68 (see FIG. 38 and FIG. 40).

Hence, the proximal end portion 68 bends easily when the force F1 (see FIG. 38) is applied to the proximal end portion 68 in the thickness direction, but the outside portion 70 does not bend easily when the force F2 (see FIG. 40) is applied to the engaging pawl portion 71 in the thickness direction. This also facilitates cancelling the engagement of the engaging pawl portion 71 with the receiving portion 56 and enables easy detachment of the adapter 20 from the separator 19 when the force F1 is applied to the proximal end portion 68, while making it difficult to cancel the engagement of the engaging pawl portion 71 with the receiving portion 56 and allowing prevention of the detachment of the adapter 20 from the separator 19 when the force F2 is applied to the engaging pawl portion 71.

In some embodiments, when a person, an appliance, or the like present in the operating room unexpectedly comes into contact with the separator 19 or the adapter 20 and an external force is applied, as described above, a state inside the body cavity 201 may not be accurately observed by an endoscope.

Further, because the surgical operation using the surgery assisting device 1 is performed by the operator who remotely operates the surgery assisting device 1 according to the master-slave system, when the position of each part in the surgical instrument 80 is unexpectedly changed with respect to the holding body 18, the position and pose of the surgical instrument 80 which are recognized by the operator in reference to information input to the operating device as the master machine are different from the actual position and pose of the surgical instrument 80, and accuracy and safety of the surgery may be decreased.

Accordingly, as described above, the surgical instrument holding device 16 has the restricting portions 56*b* formed in the separator 19. The restricting portions 56*b* engage with the restricted portion 65*b* and restrict rotation of the adapter 20 in the circumferential direction of the tubular portion 64.

Hence, in a state in which the adapter 20 is attached to the separator 19 and the separator 19 is attached to the holding body 18, rotation of the adapter 20, to which the surgical instrument 80 is attached, with respect to the separator 19 is restricted. Thus, unintended rotation of the surgical instrument 80 with respect to the holding body 18 is prevented, and accuracy and safety of the surgery can be reserved by prevention of displacement of the surgical instrument 80 with respect to the holding body 18.

In some embodiments, the separator 19 is provided with the rotation restricted portions 57, and the rotation restricting portions 53*b* are formed in the holding body 18. The rotation restricting portions 53*b* engage with the rotation restricted portions 57 and restrict rotation of the separator 19 in the circumferential direction of the insertion portion 55.

Hence, in a state in which the adapter 20 is attached to the separator 19 and the separator 19 is attached to the holding body 18, rotation of the adapter 20 with respect to the separator 19 is restricted, and rotation of the separator 19 with respect to the holding body 18 is restricted. Thus, unintended rotation of the surgical instrument 80 with respect to the holding body 18 is prevented, and accurate surgery can be performed while high positional accuracy of the surgical instrument 80 is ensured.

In the surgery assisting device 1, the surgical instrument holding device 16 may be rotated with respect to the fourth movable body 15 during the surgery and before and after the surgery. In this case, the driving body 17 of the surgical instrument holding device 16 is rotated with respect to the fourth movable body 15. The driving body 17 is rotatable between a first rotational position and a second rotational position with respect to the fourth movable body 15 (see FIG. 41 and FIG. 42).

Figure 41:
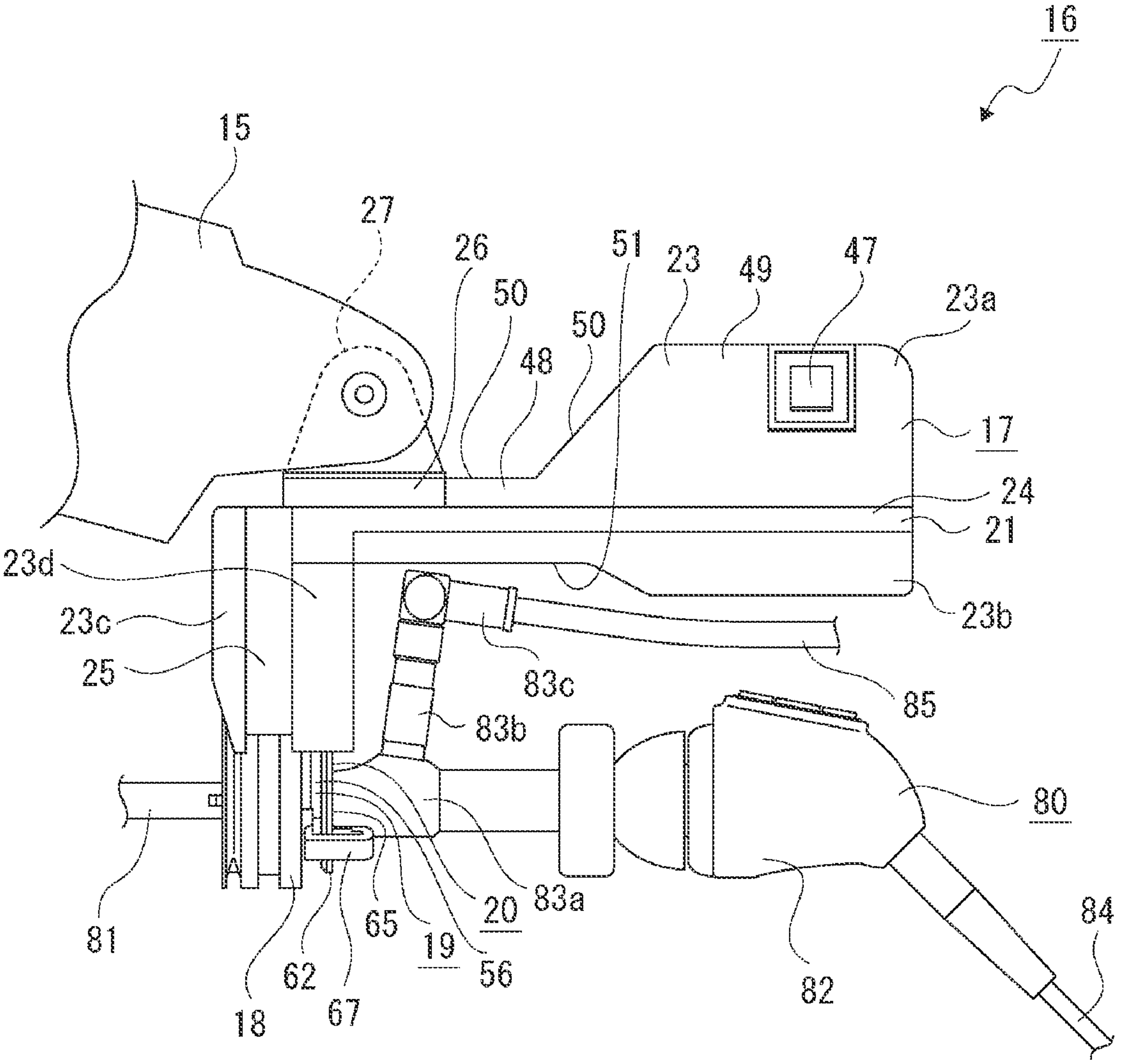
FIG. 41 is a side view illustrating a state in which the driving body is positioned at a first rotational position, according to some embodiments.
Figure 42:
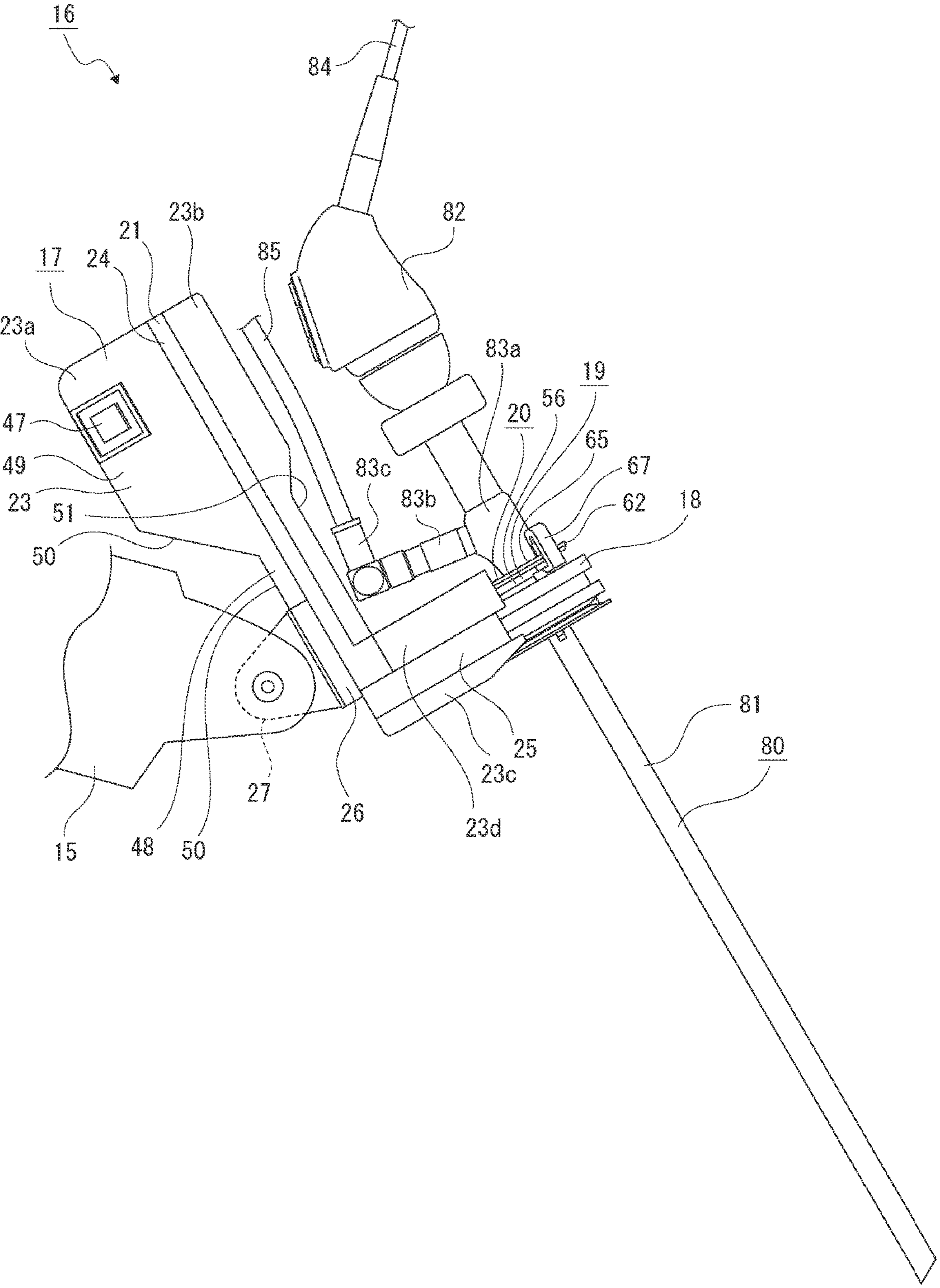
FIG. 42 is a side view illustrating a state in which the driving body is positioned at a second rotational position, according to some embodiments.

The first rotational position is, for example, a position at which the shaft portion 81 of the surgical instrument 80 is held in a substantially horizontal state (see FIG. 41). The second rotational position is, for example, a position at which the shaft portion 81 of the surgical instrument 80 is slightly inclined with respect to a vertical direction in a state in which the shaft portion 81 is located below the camera head 82 (see FIG. 42).

As described above, the surgical instrument holding device 16 is formed in substantially the shape of an L as a whole. A front side part in the part extending in the forward-rearward direction in the surgical instrument holding device 16 is provided as the narrow width portion 48 having a small vertical width. A rear side part in the part extending in the forward-rearward direction in the surgical instrument holding device 16 is provided as the wide width portion 49 having a larger vertical width than the narrow width portion 48.

The part extending in the forward-rearward direction in the driving body 17 is positioned to be close to the fourth movable body 15 at the second rotational position. However, the driving body 17 is formed in a shape constituted by the narrow width portion 48 and the wide width portion 49 as described above. Thus, at the second rotational position, the narrow width portion 48 is close to the fourth movable body 15, a part of the fourth movable body 15 is positioned in the first recess-shaped space 50, and the driving body 17 is not in contact with the fourth movable body 15 (see FIG. 42).

Hence, contact of the driving body 17 with the fourth movable body 15 is avoided, so that damage to the driving body 17 and the fourth movable body 15 can be prevented, and the driving body 17 can be rotated smoothly with respect to the fourth movable body 15.

In some embodiments, because the driving body 17 is formed in a shape constituted by the narrow width portion 48 and the wide width portion 49, the light guide 83 of the surgical instrument 80 is close to the narrow width portion 48, and the light entry portion 83*c* is positioned in the second recess-shaped space 51, and is positioned in such a manner as to be separated from the wide width portion 49.

Hence, damage to the driving body 17 and the light guide 83 can be prevented, and the surgical instrument 80 can be rotated smoothly with respect to the driving body 17 in an axial rotation direction about the shaft portion 81 without interfering with the driving body 17.

In particular, in the driving body 17, because a part close to the connecting member 27 as a part coupled to the fourth movable body 15 is provided as the narrow width portion 48 and a part separated from the connecting member 27 is provided as the wide width portion 49, a necessary configuration for rotating the holding body 18, such as the encoder 32 and the driving motor 33, can be disposed in the wide width portion 49 having a large arrangement space. Thus, an improvement in a degree of freedom of design can be achieved.

In some embodiments, because the shaft-shaped connecting shaft 35 for transmitting a driving force from the driving motor 33 to the holding body 18 is disposed in the narrow width portion 48, the external shape of the narrow width portion 48 can be reduced as much as possible, and interference between the driving body 17 and the fourth movable body 15 and interference between the driving body 17 and the light guide 83 can be avoided in an easy and efficient manner.

Other Embodiments

Figure 43:
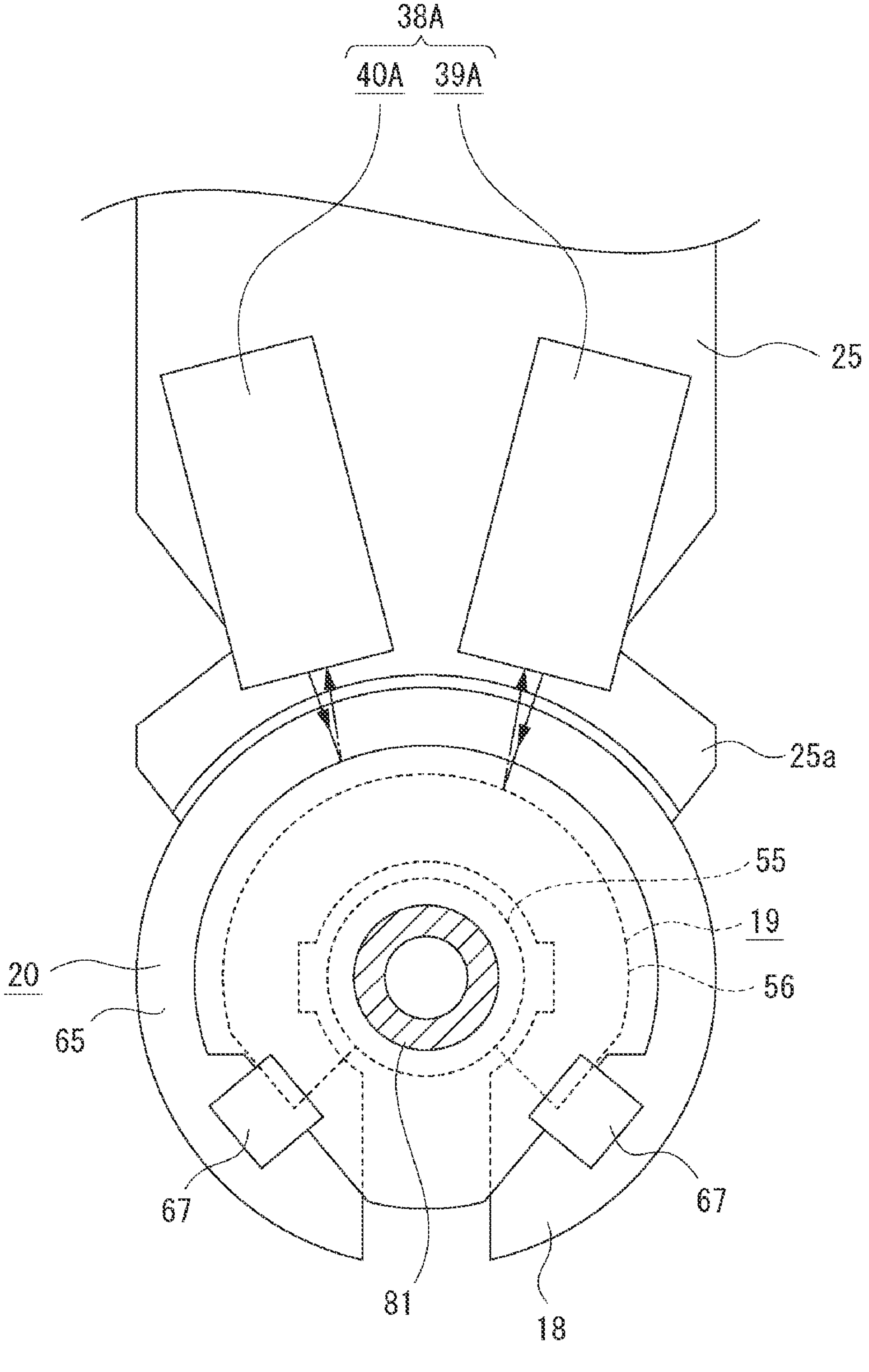
FIG. 43 is a rear view illustrating an example of a detecting mechanism that performs detection by detection light, according to some embodiments.

While the above description illustrates, as an example, the detecting mechanism 38 provided with the main body sections 41 and 44 and the detecting pins 42 and 45 moved with respect to the main body sections 41 and 44, the surgical instrument holding device 16 may use a detecting mechanism 38A that performs detection according to detection light, in place of the detecting mechanism 38 (see FIG. 43).

In a case where the detecting mechanism 38A is used, at least the receiving portion 56 of the separator 19 and at least the pressing portion 65 of the adapter 20 are formed by a material capable of reflecting light, or are subjected to surface treatment that enables reflection of light.

The detecting mechanism 38A includes a first detecting unit 39A and a second detecting unit 40A. The first detecting unit 39A and the second detecting unit 40A are each provided with a light emitting unit and a light receiving unit that are not illustrated. The light emitting units of the first detecting unit 39A and the second detecting unit 40A respectively emit laser light (detection light) to the receiving portion 56 of the separator 19 and the pressing portion 65 of the adapter 20.

When the laser light emitted from the light emitting unit of the first detecting unit 39A is reflected by the receiving portion 56 and is received by the light receiving unit of the first detecting unit 39A, light reception of the laser light by the light receiving unit is sent out as a detection signal to the detecting circuit, and accordingly, it is detected that the separator 19 is properly attached to the holding body 18.

In some embodiments, when the laser light emitted from the light emitting unit of the second detecting unit 40A is reflected by the pressing portion 65 and is received by the light receiving unit of the second detecting unit 40A, light reception of the laser light by the light receiving unit is sent out as a detection signal to the detecting circuit, and accordingly, it is thereby detected that the adapter 20 is properly attached to the separator 19.

The surgical instrument holding device 16 is thus provided with the detecting mechanism 38A including the light emitting units that emit the detection light to the separator 19 or the adapter 20 and the light receiving units that receive the detection light reflected by the separator 19 or the adapter 20. Thus, the state of attachment of the separator 19 to the holding body 18 is detected according to the detection light reflected by the separator 19, and the state of attachment of the adapter 20 to the separator 19 is detected according to the detection light reflected by the adapter 20.

Hence, the states of attachment of the separator 19 and the adapter 20 can be detected easily by a simple configuration.

In some embodiments, the rotational directions of the first movable body 7, the second movable body 8, the third movable body 12, the fourth movable body 15, the driving body 17, and the holding body 18 described above are not limited to the directions illustrated in the above description, and may be any directions as long as the surgical instrument 80 can be moved in three axial directions orthogonal to each other and can be set in any pose.

Further, while the above description illustrates the surgery assisting device 1 having six degrees of freedom as an example, the surgery assisting device 1 can be of any configuration as long as the surgery assisting device 1 is configured to be movable in three axial directions orthogonal to each other.

Figure 44:
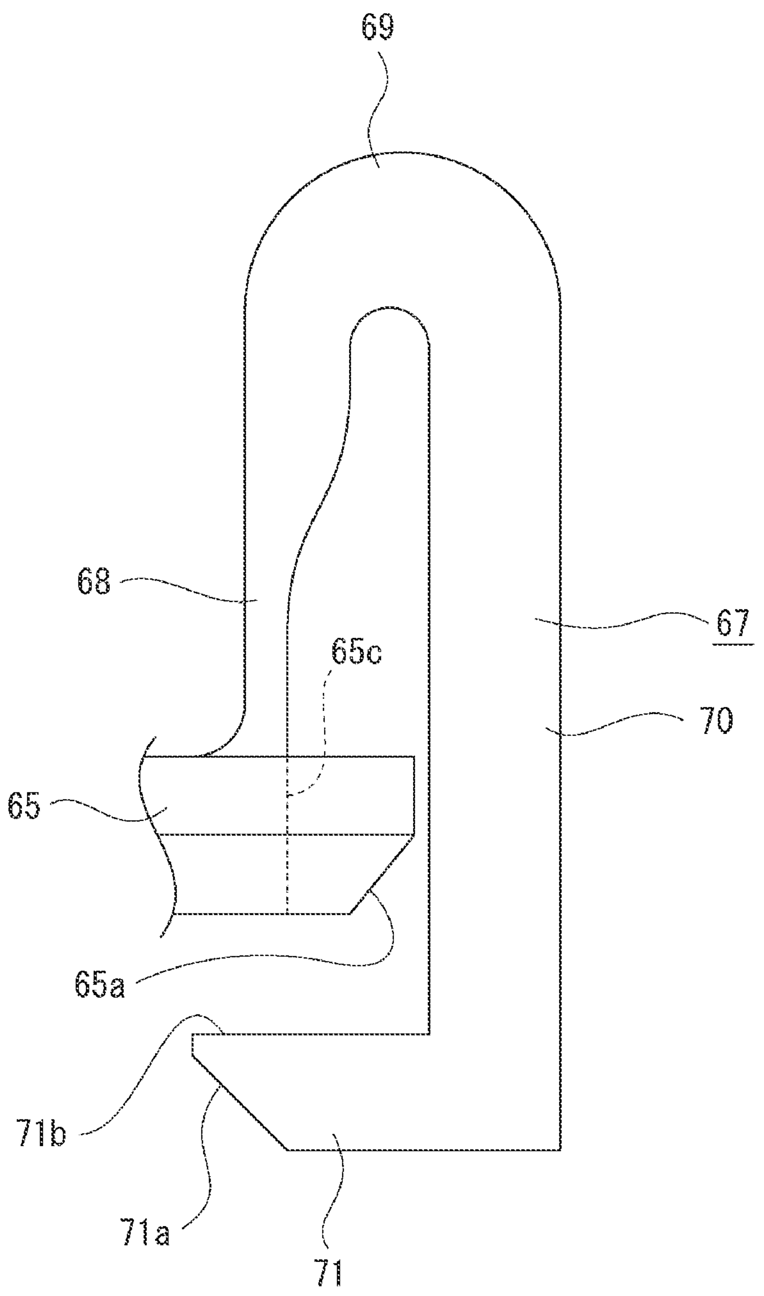
FIG. 44 is a plan view illustrating a second engaging portion formed in another shape, according to some embodiments.

Furthermore, while the above description illustrates an example in which the adapter 20 is provided with the second engaging portion 67 having the stepped surface 69*a* formed at a boundary part between the folded portion 69 and the proximal end portion 68, a surface in the thickness direction of the proximal end portion 68 may, for example, be formed as a curved surface or a flat surface, and the proximal end portion 68 may be continuous with the folded portion 69 (see FIG. 44).

The provision of the second engaging portion 67 in which the surface in the thickness direction of the proximal end portion 68 is thus formed in a curved surface or a flat surface and the proximal end portion 68 is continuous with the folded portion 69 makes it difficult for stress concentration to occur at the boundary part between the proximal end portion 68 and the folded portion 69, and can therefore achieve an improvement in strength of the second engaging portion 67.

It should be understood that the present disclosure is not limited to the above embodiments, but various other changes and modifications may be made therein without departing from the spirit and scope of the appended claims.

What is claimed is:

1. A surgical instrument holding device comprising:

an adapter from which a surgical instrument is detachable and that is provided with a restricted portion;

a separator from which the adapter is detachable;

a holding body from which the separator is detachable; and a driving body configured to support the holding body in a rotatable manner and apply a driving force to the holding body, wherein the adapter is provided with a tubular portion through which the surgical instrument penetrates, the separator is provided with an insertion portion into which the tubular portion is inserted, the surgical instrument is held by the holding body via the adapter and the separator, a restricting portion is formed in the separator, the restricting portion engages with the restricted portion of the adapter to restrict rotation of the adapter in a circumferential direction of the tubular portion, a rotation restricted portion is provided in the separator, a rotation restricting portion is formed in the holding body, the rotation restricting portion engages with the rotation restricted portion to restrict rotation of the separator in a circumferential direction of the insertion portion, a first engagement receiving portion is formed in the holding body, a second engagement receiving portion is formed in the separator, the separator is provided with a first engaging portion that is elastically deformed and engaged with the first engagement receiving portion at a time of attachment of the separator to the holding body, the adapter is provided with a second engaging portion that is elastically deformed and engaged with the second engagement receiving portion at a time of attachment of the adapter to the separator, and the separator is attached to the holding body by engagement of the first engaging portion with the first engagement receiving portion in a state in which the first engaging portion is elastically restored, and the adapter is attached to the separator by engagement of the second engaging portion with the second engagement receiving portion in a state in which the second engaging portion is elastically restored.

2. The surgical instrument holding device according to claim 1, wherein:

the rotation restricted portion and the first engaging portion are formed in a shape that protrudes with respect to the insertion portion, and the rotation restricted portion and the first engaging portion are continuous with each other.

3. The surgical instrument holding device according to claim 2, wherein:

an insertion and extraction opening that opens in a radial direction is formed in the insertion portion, and the surgical instrument that is attached to the adapter is inserted or extracted through the insertion and extraction opening.

4. The surgical instrument holding device according to claim 1, wherein:

an insertion and extraction opening that opens in a radial direction is formed in the insertion portion, and the surgical instrument that is attached to the adapter is inserted or extracted through the insertion and extraction opening.

5. A surgery assisting device comprising the surgical instrument holding device according to claim 1.

6. The surgical instrument holding device according to claim 1, wherein:

the separator is further provided with a flange portion that projects outward from a rear edge of the insertion portion, and the restricting portion is provided on the flange portion.

7. The surgical instrument holding device according to claim 1, further comprising:

an attachment portion that attaches to the tubular portion of the adaptor and fastens the tubular portion to the surgical instrument.

8. The surgical instrument holding device according to claim 7, wherein the tubular portion is provided with fastening portions that are elastically deformable.

* * * * *